United States Patent
Alt et al.

(10) Patent No.: US 9,518,293 B2
(45) Date of Patent: Dec. 13, 2016

(54) HIGH THROUGHPUT GENOME-WIDE TRANSLOCATION SEQUENCING

(75) Inventors: Frederick W. Alt, Cambridge, MA (US); Zhang Yu, West Roxbury, MA (US); Roberto Chiarle, Brookline, MA (US); Monica Gostissa, Jamaica Plain, MA (US)

(73) Assignee: Children's Medical Center Corporation, Boston, MA (US)

( * ) Notice: Subject to any disclaimer, the term of this patent is extended or adjusted under 35 U.S.C. 154(b) by 70 days.

(21) Appl. No.: 14/131,236

(22) PCT Filed: Jul. 6, 2012

(86) PCT No.: PCT/US2012/045648
§ 371 (c)(1),
(2), (4) Date: Apr. 14, 2014

(87) PCT Pub. No.: WO2013/006745
PCT Pub. Date: Jan. 10, 2013

(65) Prior Publication Data
US 2014/0234847 A1    Aug. 21, 2014

Related U.S. Application Data

(60) Provisional application No. 61/505,374, filed on Jul. 7, 2011.

(51) Int. Cl.
*C12Q 1/68* (2006.01)
*C12P 19/34* (2006.01)

(52) U.S. Cl.
CPC .......... *C12Q 1/6869* (2013.01); *C12Q 1/6855* (2013.01)

(58) Field of Classification Search
CPC ............... C12Q 1/6855; C12Q 1/6869; C12Q 2525/301; C12Q 2525/155; C12Q 2525/191; C12Q 2531/131; C12Q 2531/122; C12Q 2549/119
See application file for complete search history.

(56) References Cited

U.S. PATENT DOCUMENTS

2009/0047680 A1    2/2009    Lok

FOREIGN PATENT DOCUMENTS

WO    2011017596 A2    2/2011

OTHER PUBLICATIONS

Chiarle, Roberto et al, "Genome-Wide Translocation Sequencing Reveals Mechanisms of Chromosome Breaks and Rearrangements in B Cells", Cell, Sep. 2011, vol. 147, Issue 1, pp. 107-119.
Mahowald et al., "Aberrantly resolved RAG-mediated DNA breaks in Atm-deficient lymphocytes target chromosomal breakpoints in cis", PNAS 106(43):18339-18344 (2009).
Siebert et al., "An improved PCR method for walking in uncloned genomic DNA", Nucleic Acids Research 23(6):1087-1088 (1995).

*Primary Examiner* — Young J Kim
(74) *Attorney, Agent, or Firm* — Nixon Peabody LLP; David S. Resnick; Leena H. Karttunen Contarino

(57) ABSTRACT

Provided are methods for high-throughput screening to determine locations of double-stranded DNA breaks (DSBs) and translocations in genomes caused by different agents, such as enzymes.

11 Claims, 18 Drawing Sheets

| METHOD | ad-PCR | ad-PCR | ad-PCR | circ-PCR |
|---|---|---|---|---|
| MOUSE DNA | c-myc$^{25x}$ I-SceI WT | c-myc$^{25x}$ I-SceI AID-/- | $\Delta S\gamma 1^{2x}$ I-SceI WT | c-myc$^{25x}$ I-SceI WT |
| HUMAN DNA | K562 | K562 | K562 | K562 |
| MOUSE JUNC. | 2257 | 1957 | 1837 | 316 |
| HUMAN JUNC. | 12 | 11 | 4 | 2 |
| BACKGROUND | 0.53% | 0.56% | 0.33% | 0.63% |

| CHROMOSOME | SEQUENCE | POSITION | GENE | HITS | IN VITRO CUTTING |
|---|---|---|---|---|---|
| Canonical | ATTACCCTGTTATCCCTA | | | | |
| chr2 (C) | TCTGCCCTGGTATCCCTG | 155631477 | Mmp24 | 102 | +++ |
| chr15 (B) | TTTAGCCTGGTATCCCTA | 81735362 | Aco2 | 58 | +++ |
| chr14 | TCTGCCCTGGTATCCCTG | 46096826 | Fermt2 | 45 | +++ |
| chr7 | ACTGCCCTGTTATCCCAA | 112727865 | Apbb1 | 39 | +++ |
| chr1 (B) | ATTACCCCTGTTATCCCTA | 137751636 | NA | 35 | ++ |
| chr9 | GCTGCCCTGGTATCCCTA | 34715224 | Kirrel3 | 28 | +++ |
| chr1 (A) | ACTGCCCTGGCATCCCTA | 31667702 | NA | 25 | nd |
| chr11 | TTTGCCCTGTCATCCCTA | 69472600 | Mpdu1 | 14 | nd |
| chrX | ATTGGCCCTGTTATCCCTA | 11377980 | NA | 14 | ++ |
| chr2 (B) | TGAGCCCTGTTATCCCTA | 46569867 | NA | 12 | + |
| chr19 (A) | ATAACCCTGTTATCCCTG | 25594543 | Dmrt1 | 11 | ++ |
| chr19 (B) | ATGACCCTGTTATCCCTA | 44375497 | Scd2 | 10 | ++ |
| chr15 (A) | AATACCCTGTGATCCCTA | 62305495 | NA | 6 | - |
| chr2 (A) | ATTACCCTGGTATCCCAA | 72097840 | NA | 6 | +++ |
| chr4 | ATGCCCCTGTTATCCCTA | 149646778 | NA | 6 | + |
| chr8 | ATGACCCTGGTATCCCTA | 64212875 | Pa11d | 5 | +++ |
| chr6 | TAAGACCTGGTATCCCTA | 62671395 | NA | 4 | nd |
| chr13 | ATTACCCTGTTATCCCTT | 5934759 | NA | 1 | ++ |

FIG. 3A

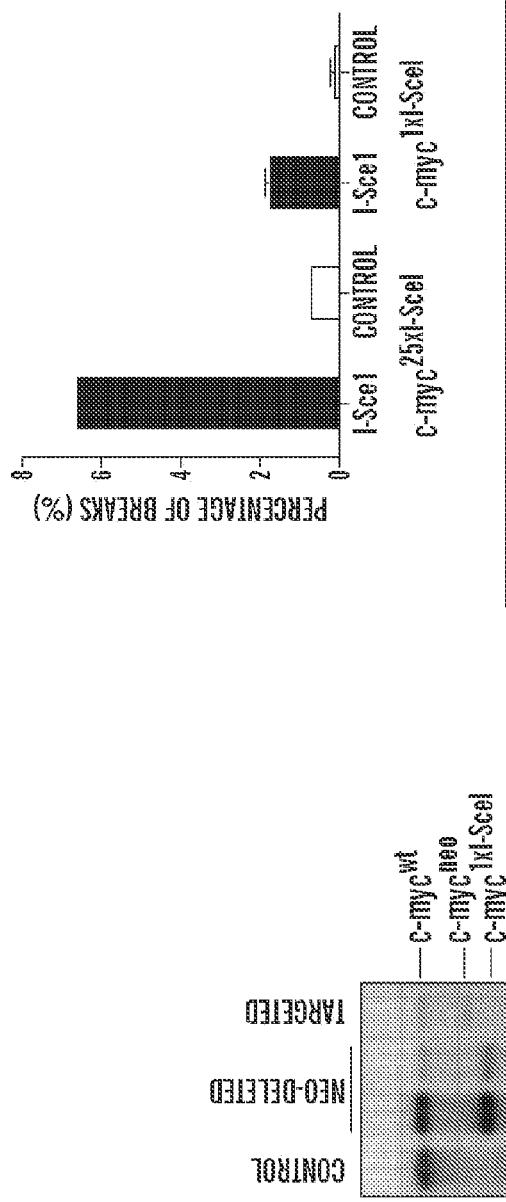
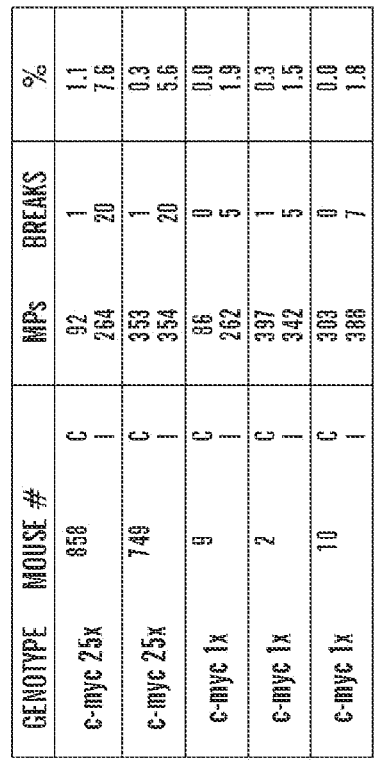
FIG. 4C
FIG. 4B

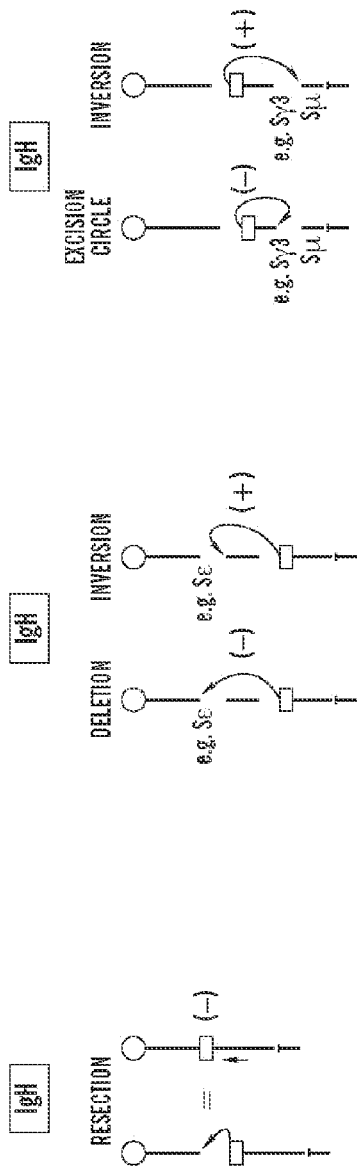
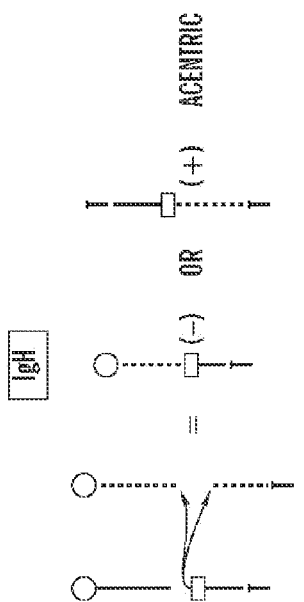
FIG. 6E
FIG. 6F
FIG. 6G
FIG. 6H

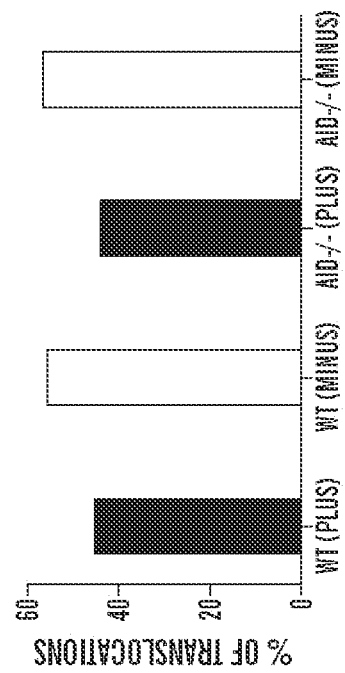
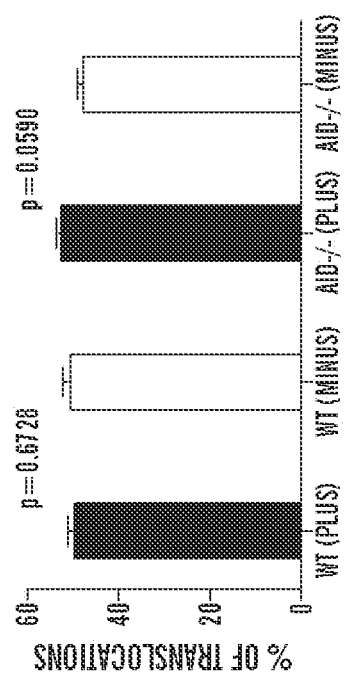
FIG. 6I
FIG. 6J

HIGH THROUGHPUT GENOME-WIDE TRANSLOCATION SEQUENCING

CROSS-REFERENCE TO RELATED APPLICATIONS

This application is a 35 U.S.C. §371 National Phase Entry Application of International Application No. PCT/US2012/045648 filed Jul. 6, 2012, which designates the U.S., and which claims benefit under 35 U.S.C. §119(e) of a U.S. provisional patent application Serial No. 61/505,374, filed Jul. 7, 2011, the contents of which are incorporated herein by reference in their entireties.

GOVERNMENT SUPPORT

This application was supported in part by Grant numbers 5P01CA92625; KO8 grant AI070837; and 5T32CA070083-13 awarded by the National Institutes of Healt. The U.S. Government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 28, 2012, is named 071181PCT.txt and is 15,832 bytes in size.

FIELD OF THE INVENTION

Disclosed methods relate analysis of genomes for specific genetic events, such as DNA breaks and translocations caused by such breaks.

BACKGROUND

Methods for assessing whole genomes have become ever more important not only in research of genomes, but also in view of methods that aim at whole-genome manipulation to improve conditions, such as diseases. The methods for manipulating whole genomes by silencing a gene, inserting a new gene and editing or correcting genes are gaining significant importance.

However, to ensure that the methods aimed at improving the genome do not harm it, one must be aware of how the tools, such as double stranded DNA break causing agents, including enzymes, affect the genomes to be manipulated.

Methods for such large scale analysis have been lacking in the field of genomic analyses.

Mechanistic factors that influence translocations include DSB frequency at translocating loci and factors that influence such DSBs (Robbiani et al., 2008; Wang et al., 2009), factors that contribute to two translocating loci lying in close enough proximity in the interphase nucleus to be joined (Meaburn et al., 2007; Wang et al., 2009), and mechanisms that circumvent functions of the cellular DSB response and repair pathways that promote joining of DSBs within a chromosome and suppress joining of DSBs between chromosomes (Franco et al., 2006b; Ramiro et al., 2006).

For example, the mammalian nucleus is occupied by non-randomly positioned genes and chromosomes (Meaburn et al., 2007). DNA double-strand breaks (DSBs) fuse to generate translocations which requires physical proximity; thus, spatial disposition of chromosomes might impact translocation patterns. Cytogenetic studies have revealed that certain loci involved in oncogenic translocations are spatially proximal (Meaburn et al., 2007; Misteli and Soutoglou, 2009). Studies of recurrent translocations in mouse B cell lymphomas suggested that aspects of particular chromosomal regions, as opposed to broader territories, might promote spatial proximity and influence translocation frequency (Wang et al., 2009). Non-random position of genes and chromosomes in the nucleus led to two general models for translocation initiation. "Contact-first" poses translocations are restricted to proximally-positioned chromosomal regions; while "breakage-first" poses that distant DSBs can be juxtaposed (Meaburn et al., 2007).

In depth evaluation of how chromosomal organization influences translocations requires a genome-wide approach. Such genome-wide approaches could also be applied in evaluating agents that create DSBs for their cutting specificity and genome wide effects for recombination events throughout any given genome.

SUMMARY

We now provide novel methods for analyzing whole genomes for translocation events that are a result of DNA double-strand breaks. We also provide methods for screening agents, such as enzymes for cutting specificity and risk for unwanted recombination events or locations. These methods can be used to optimize DNA cutting agents such as enzymes used in various areas of genetic and genomic engineering.

We have developed a method that can be used to identify the universe of translocations (the "translocatome") arising from a specific cellular DNA double-strand break (DSB) and that can detect the location of the DSBs created by agents causing them. The method, which we call "High Throughput Genome-wide Translocation Sequencing" or "HTGTS", which allows isolation of junctions between a DSBs introduced at a fixed sites and DSBs induced or naturally occurring at other chromosomal locations genome-wide.

To illustrate how this method works, we have used the method to isolate large number of translocations from an exemplary cell type, namely, primary B cells activated for CSR, to provide a genome-wide analysis of the relationship between translocations and particular classes of DSBs, transcription, chromosome domains, and other factors. Other cells and genomes may be analyzed using the same general methods.

The novel method is widely applicable to any cell one wishes to identify a "translocatome" in, i.e., the universe of translocations arising from any specific DSB, and to application with any agent that can cause a DSB, such as meganucleases, zinc-finger nucleases, TALEns and even chemical agents designed for and used in, e.g., genome engineering. The cells may be e.g., mammalian cells or plant cells.

The method is therefore useful, for example, for anyone wishing to scan for possible translocations arising from use of any specific agent, such as an enzyme used to create a DSB for, e.g., genetic or genome engineering. The same method can also be used to screen the specificity of DSB causing agents, such as enzymes. For example, one can screen enzymes for risk of unwanted breaks or recombinations to be used in applications such as inserting a gene to a genome. Optimizing the specificity and recombination risks, one can avoid using enzymes that pose a high risk of unwanted recombination events, such as those that disrupt genes or other DNA sequences that are important for the integrity of the normal cellular functions. The agent may also be a therapeutic agent, such as a chemotherapy agent.

In such a case, one can use the method to screen for potential DSBs and/or translocation events that may occur as a result of exposing a cell to the chemotherapeutic agent. The present method allows for mapping or screening for potential off-target recombinations that may result from using a specific enzyme, such as rare cutting enzymes, e.g., a meganuclease. Thus, the method allows optimizing the types of enzymes or agents used in genome engineering applications.

Accordingly, in one embodiment, the invention provides a method for high throughput, genome-wide translocation sequencing (HTGTS) and detection of double-stranded DNA break (DSB) locations, the method comprising the steps of: (a) exposing a cell to an agent known or suspected of being capable of producing at least one DSB; (b) optionally allowing the cell to divide for at least 12 hours and extracting genomic DNA; (c) producing a fragmented DNA sample by fragmenting the DNA of the cell with a frequently cutting restriction enzyme; (d) producing a ligated DNA product by ligating an asymmetric adapter to the fragmented DNA sample, wherein the asymmetric adapter comprises a sequence that is designed to anneal to the DNA end generated by the frequently cutting restriction enzyme and contains a stretch of known DNA sequence that can be used to design a PCR primer for a nested PCR amplification; (e) digesting the ligated DNA products with an enzyme to block amplification of germline or unrearranged targeted alleles; (f) producing nested PCR products by performing nested-PCR with adapter- and locus-specific primers using the digested ligated DNA product thereby amplifying the nucleic acid sequences surrounding the junctions around the DSBs; (g) producing sequenced nested PCR products by sequencing the nested PCR products; and (h) aligning the sequenced nested PCR products against a reference sequence to identify chromosomal locations of the translocations and the chromosomal locations of the DSBs.

The invention also provides a method for high throughput, genome-wide translocation sequencing (HTGTS) and identification of double-stranded DNA break (DSB) locations comprising the steps of: (a) exposing a cell to an agent known or suspected to be capable of producing a DSB; (b) allowing the cell to divide for at least 12 hours; (c) producing a fragmented DNA sample by fragmenting the DNA of the cell with a frequently cutting restriction enzyme; (d) producing a ligated DNA sample by ligating the fragmented DNA at a concentration favoring intra-molecular ligation; (e) digesting the ligated DNA sample with a blocking enzyme; (f) producing nested PCR products by performing a nested PCR with locus-specific primers; (g) sequencing the nested PCR products; (h) aligning the sequences against a reference sequence to identify chromosomal locations of the translocations and DSBs.

In some aspects of all the embodiments of the invention, the method further comprises a step of inserting into a cell to be analyzed at least one target sequence for the agent that is known to be absent in the genome of the cell to be analyzed prior to exposing the cell to an agent known or suspected of producing DSBs, and then exposing the cell to the agent that is known to target that sequence.

In some aspects of all the embodiments of the invention, the agent is a rare-cutting enzyme.

In some aspects of all the embodiments of the invention, the agent is a meganuclease, a TALEN or a zinc-finger nuclease.

In some aspects of all the embodiments of the invention, the cells are allowed to divide for 1-5 days.

In some aspects of all the embodiments of the invention, the cells are allowed to divide for 2-4 days.

In some aspects of all the embodiments of the invention, no cell division is required.

In some aspects of all the embodiments of the invention, the sequencing is performed using a next generation sequencing method.

In some aspects of all the embodiments of the invention, the step of aligning is performed by a non-human machine.

In some aspects of all the embodiments of the invention, the non-human machine comprises a computer executable software.

In some aspects of all the embodiments of the invention, the non-human machine further comprises a display module for displaying the results of the step of aligning.

In some aspects of all the embodiments of the invention, the cell is a mammalian cell.

In some aspects of all the embodiments of the invention, the cell is a plant cell.

BRIEF DESCRIPTION OF DRAWINGS

FIG. 1C top shows a cassette containing either 25 or one I-SceI recognition sequence(s) that was inserted into intron 1 of c-myc (see FIG. 4). FIG. 1C bottom shows a cassette composed of a 0.5 kb spacer flanked by I-SceI recognition sequences that was used to replace the IgH Sγ1region. Relative orientation of I-SceI sites is indicated by arrowheads. Position of the primers used for generation and sequencing of HTGTS libraries is shown. FIG. 1D shows an expression cassette for the I-SceI enzyme fused to a glucocorticoid receptor (I-SceI-GR) that was targeted into the murine Rosa26 locus. The red fluorescent protein Tomato (tdT) was co-expressed by means of an IRES. FIG. 1E is a schematic representation of the methods used for HTGTS. Circularization-PCR is shown on the left. Adapter-PCR is on the right. FIG. 1F shows background for the HTGTS approaches, calculated as percent of artifactual human:mouse hybrid junctions detected when human DNA was mixed 1:1 with mouse DNA from the indicated samples.

FIG. 2A shows a graph representing translocation numbers in frequently hit genes and non-annotated chromosomal regions. Only hotspots with more than 5 hits are shown and are ordered based on the frequency of translocations in the pooled c-myc25xI-SceI/WT HTGTS library (top bars). The respective frequencies of translocations in the pooled c-myc25xI-SceI/AID−/− HTGTS library are displayed underneath (bottom bars). Striped bars represent frequent hits involving cryptic I-SceI sites. The dotted and black portions of the top bars represent translocations found in c-myc1xI-SceI and c-myc25xI-SceI/ROSAI-SceI-GR libraries, respectively. Genes known to be translocated in human and mouse lymphoma or leukemia are in white. The dashed line represents the cutoff for significance over random occurrence for each of the two groups (See also Table S2). FIGS. 2B and 2C show genome-wide distribution of translocations relative to TSSs. Junctions from c-myc25x I-SceI/WT (FIG. 2B) or c-myc25x I-SceI/AID−/− (FIG. 2C)

libraries (excluding 2 Mb around the chr15 breaksite and IgH S regions) are assigned a distance to the nearest TSS and separated into "active" and "inactive" promoters as determined by GRO-seq. Translocation junctions were binned at 1 kb intervals. n represents the number of junctions within 20 kb of the TSS.

Figure 3C:
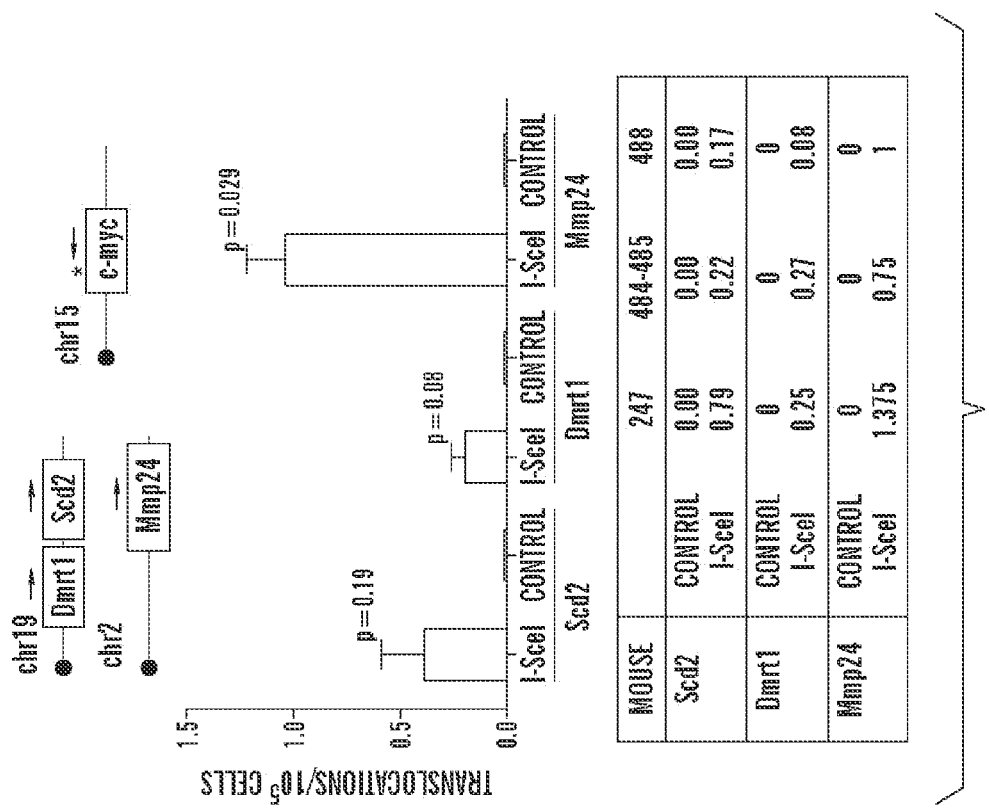
Figure 3B:
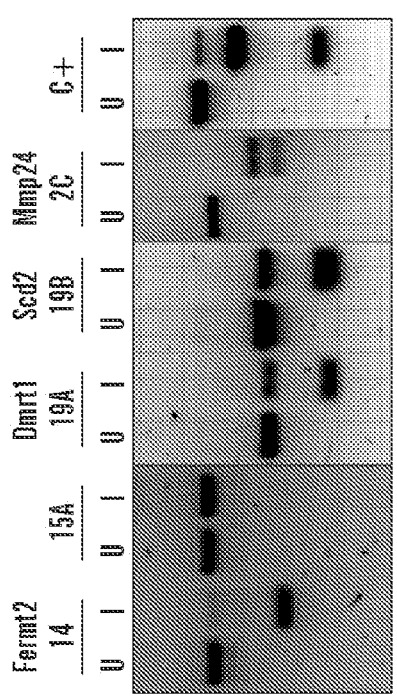
Figure 3D:
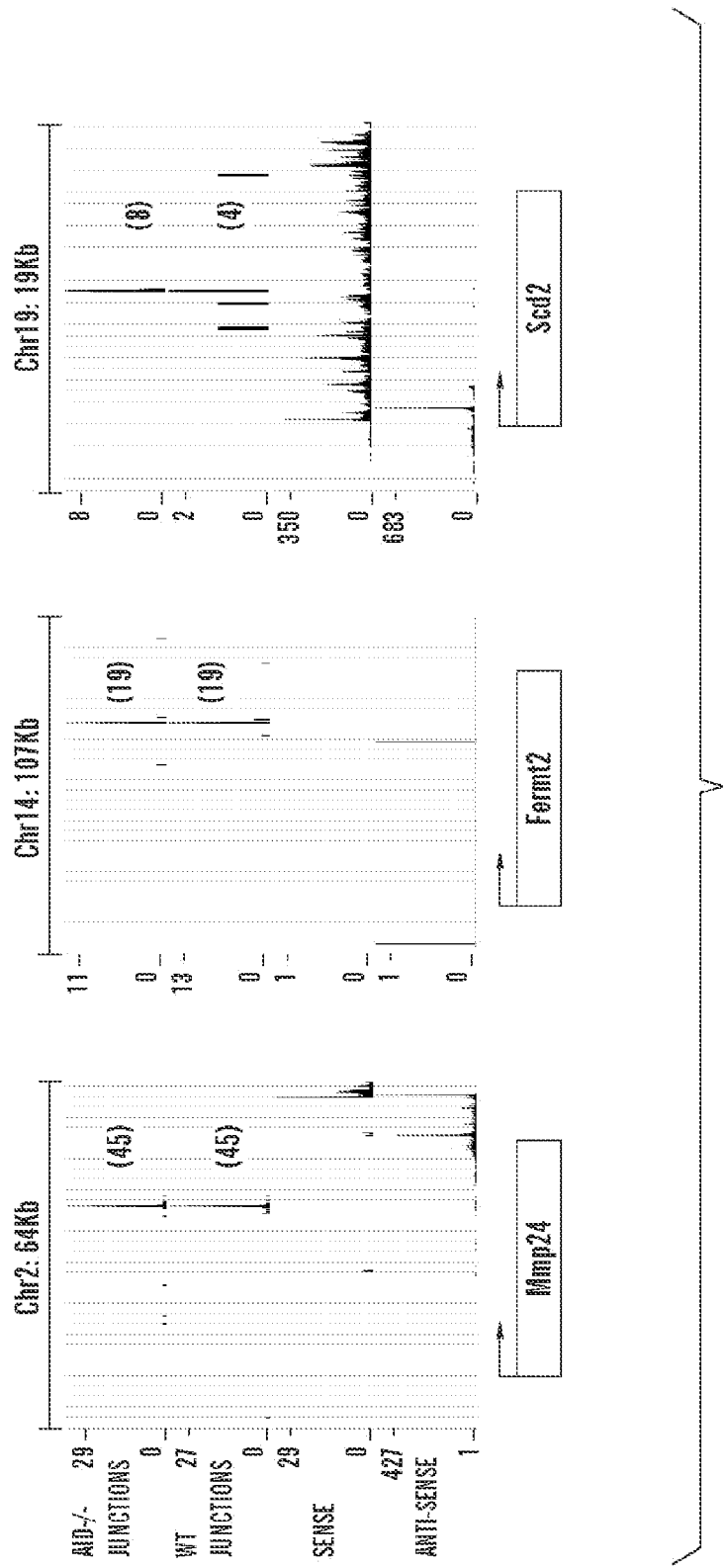

FIGS. 3A-3D show identification of cryptic I-SceI sites in the mouse genome by HTGTS. FIG. 3A shows cryptic I-SceI sites identified as frequent translocation targets. Sequences are identified as SEQ ID NOs: 57-75 in the order they appear in the Table from the top to the bottom. The canonical I-SceI recognition sequence is on top (SEQ ID NO: 57); nucleotides divergent from the consensus are boxed in the sequence. Chromosomal position and gene location of each cryptic site are indicated. "Hits" represent the total number of unique junctions identified in a 4 kb region centered around each site in the pool of all HTGTS libraries (see also Table S5). In vitro cutting efficiency, evaluated as described in the examples, is shown. NA, intergenic or not annotated; nd, not determined. FIG. 3B shows in vitro cutting of PCR products encompassing the indicated cryptic I-SceI sites. C+, positive control: PCR fragment containing a canonical I-SceI site. U, uncut; I, I-SceI-digested. FIG. 3C is a PCR analysis to detect translocations between c-myc25xI-SceI and cryptic I-SceI sites in Scd2, Dmrt1 and Mmp24 genes. (Top) Position of the primers used for PCR amplification. (Middle) Average frequency of translocations +SEM. (Bottom) Number of translocations/10' cells from three independent c-myc25xI-SceI WT mice. FIG. 3D shows transcription in genes containing I-SceI sites, as determined by GRO-seq. Translocation junctions are shown in the first (AID–/–) and second (WT) rows, sense and antisense nascent RNA signals in the third and fourth.

Figure 4A:
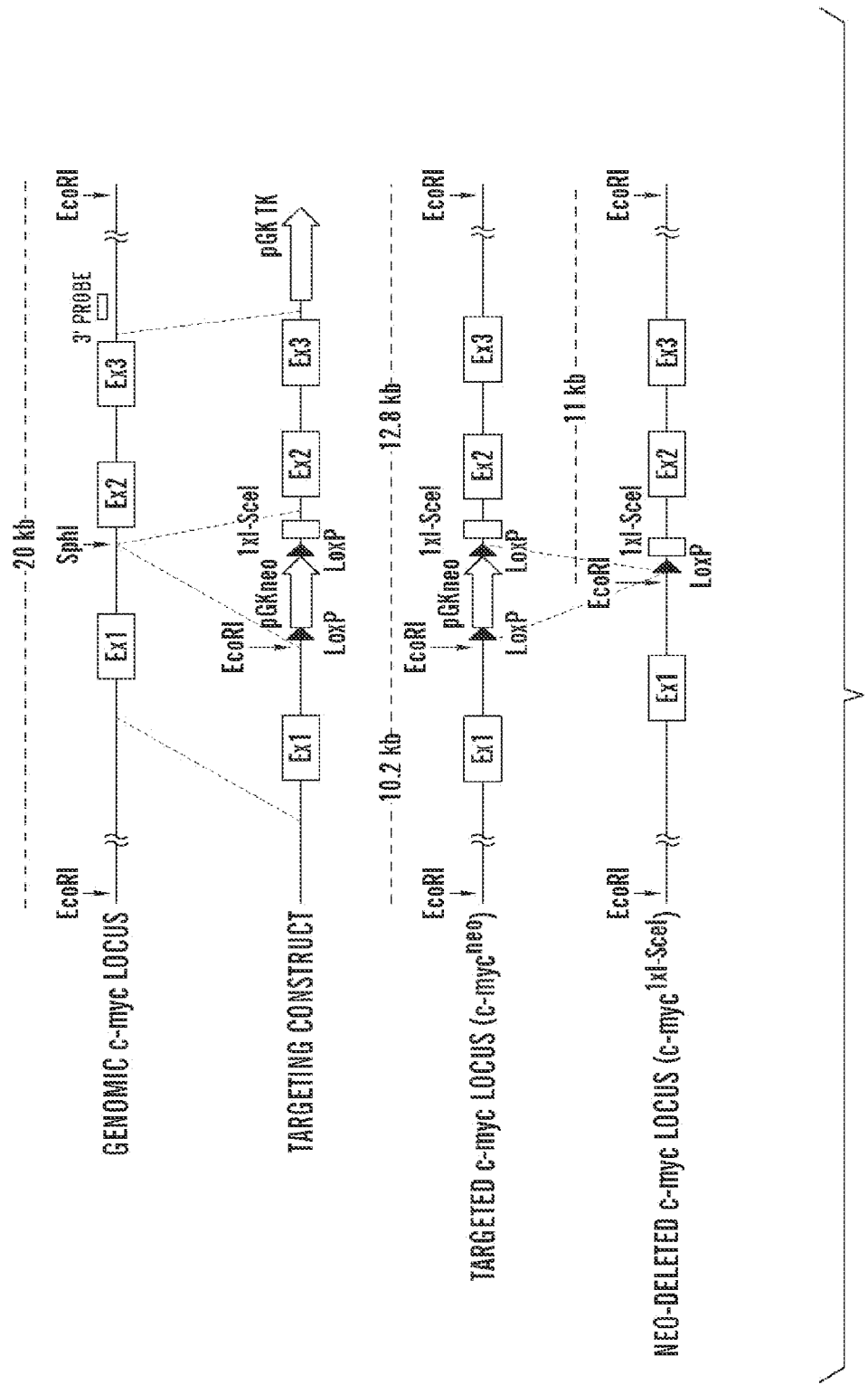

FIGS. 4A-4C show generation and characterization of c-myc1xI-SceI mice (refers to FIG. 1). FIG. 4A is a schematic map of the targeting strategy for insertion of a single I-SceI site into c-myc intron 1. The c-myc1xI-SceI allele was generated by homologous recombination into 129/Sv (TC1) ES cells of the indicated construct. Position of probe used for ES cell screening by Southern blotting is indicated. FIG. 4B shows a Southern blot analysis of DNA from a targeted clone before and after Neo-deletion. DNA was digested with EcoRI and probed with the 3' probe indicated in FIG. 4A. FIG. 4C shows efficiency of cutting of the c-myc1xI-SceI allele was tested by metaphase FISH. Splenic primary B cells were activated for CSR by αCD40/IL4 and infected with either control (FIG. 4C) or I-SceI (I) retrovirus. Metaphase spreads were prepared at day 4 and analyzed with probes flanking the c-myc locus (see Examples). Numbers of c-myc breaks are indicated for 3 independent c-myc1xI-SceI mice and two c-myc25xI-SceI mice as positive control.

Figure 5A:
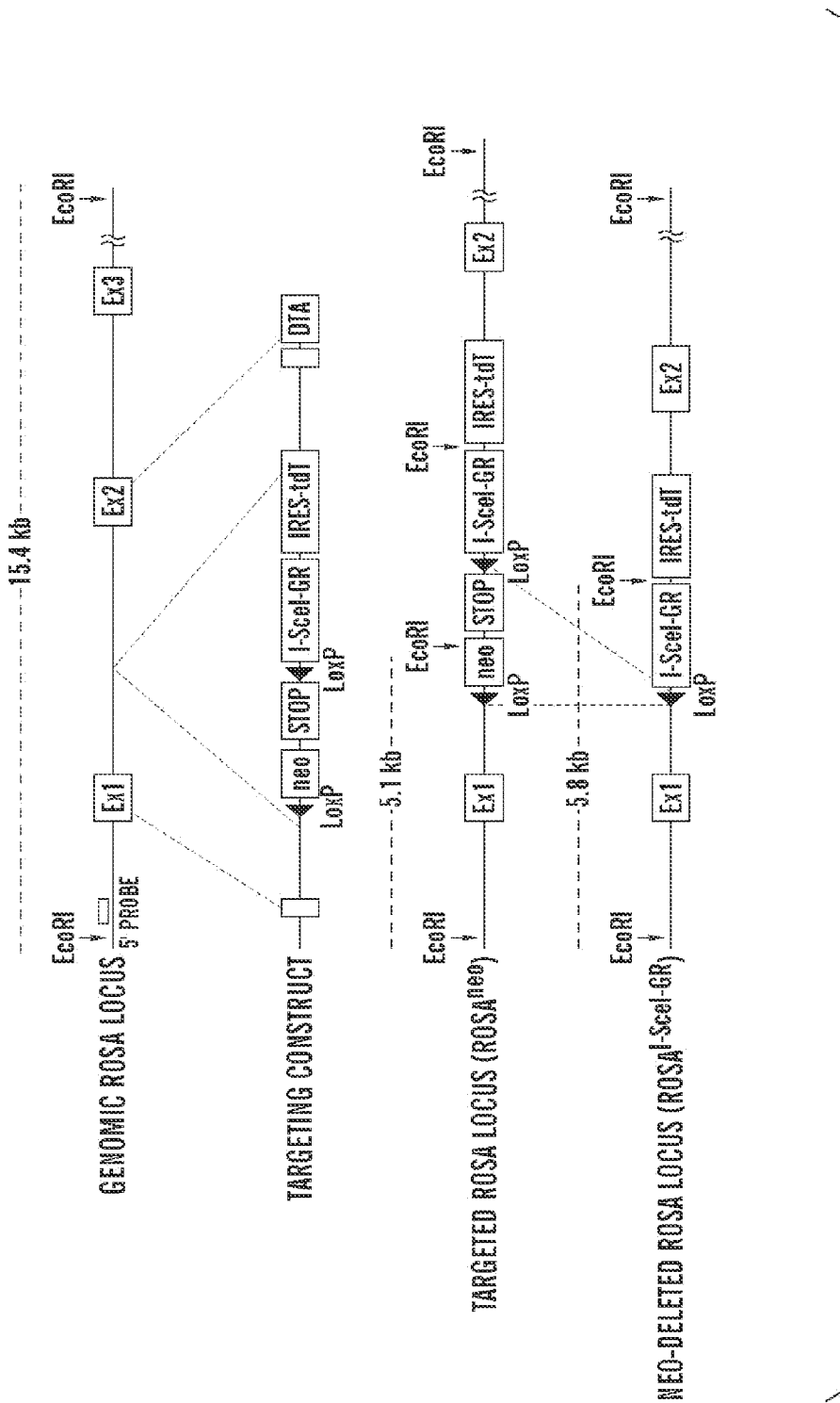
Figure 5C:
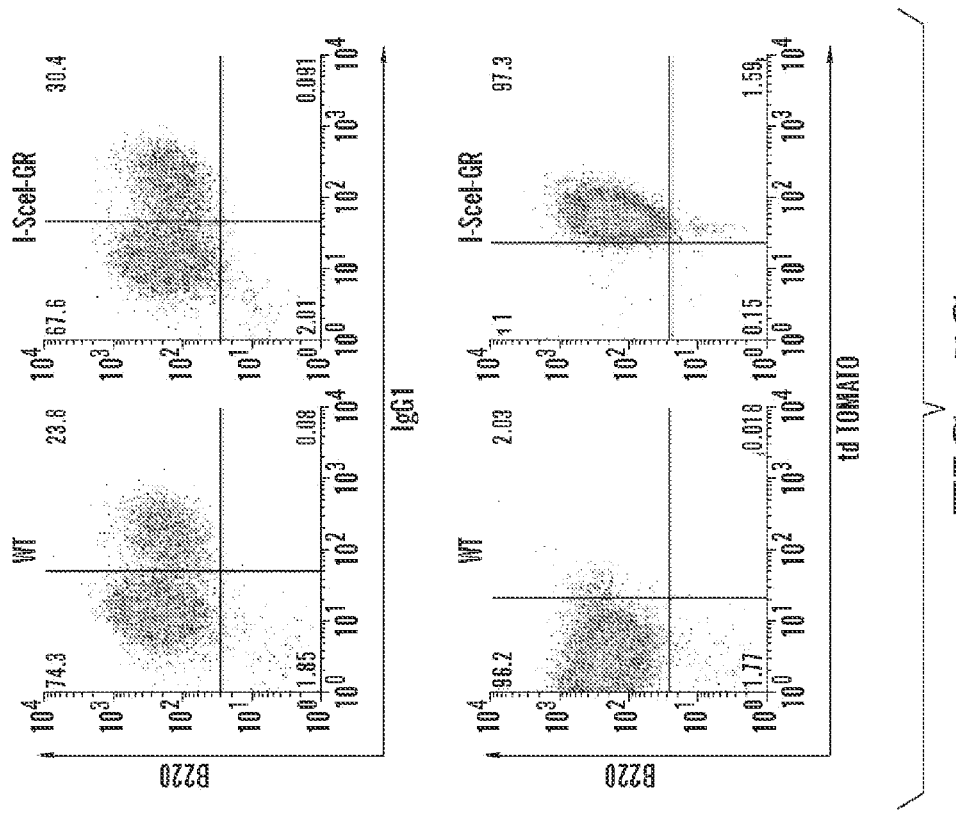
Figure 5B:
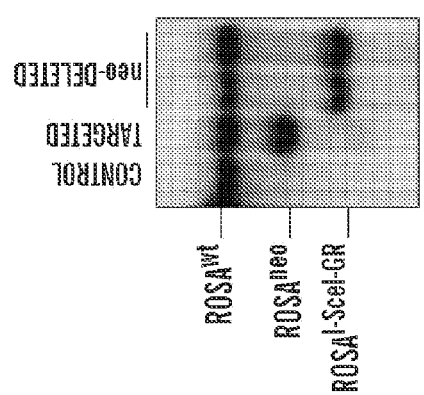
Figure 5D:
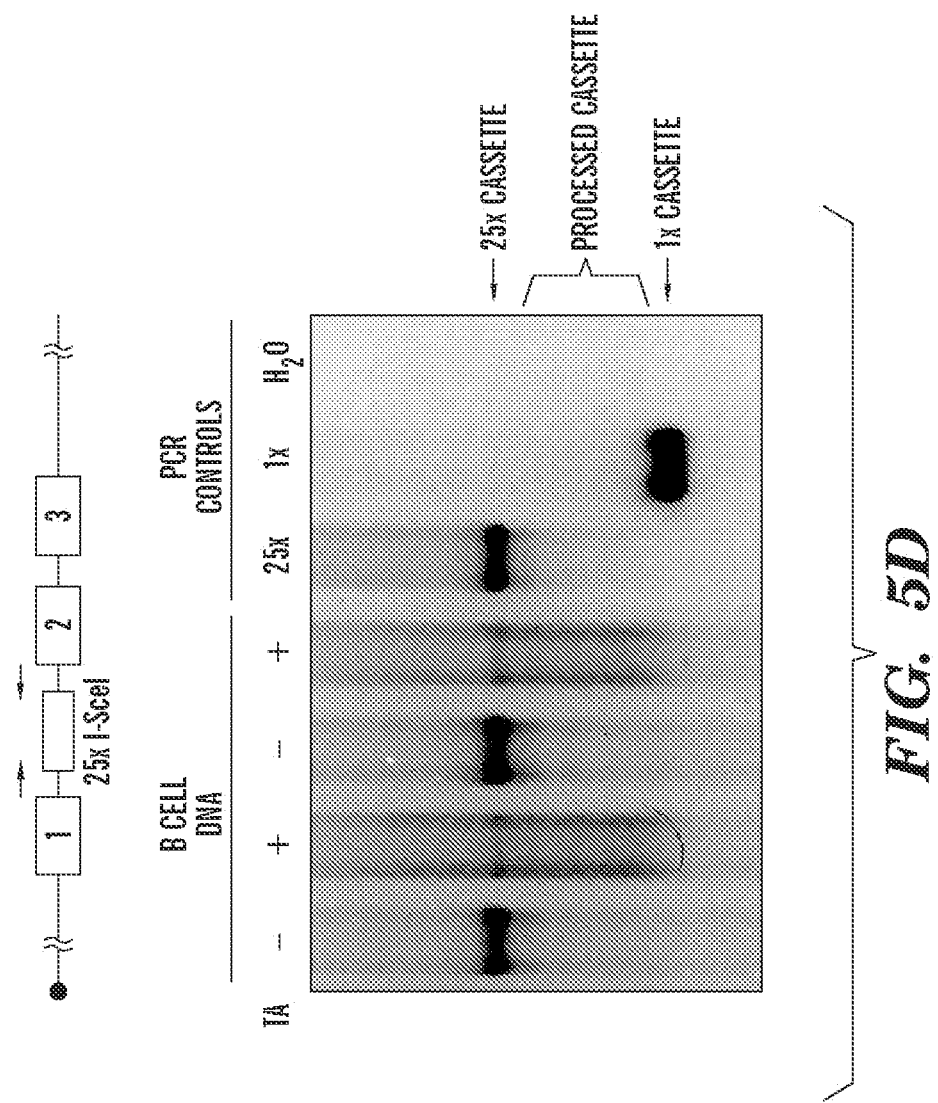
Figure 5E:
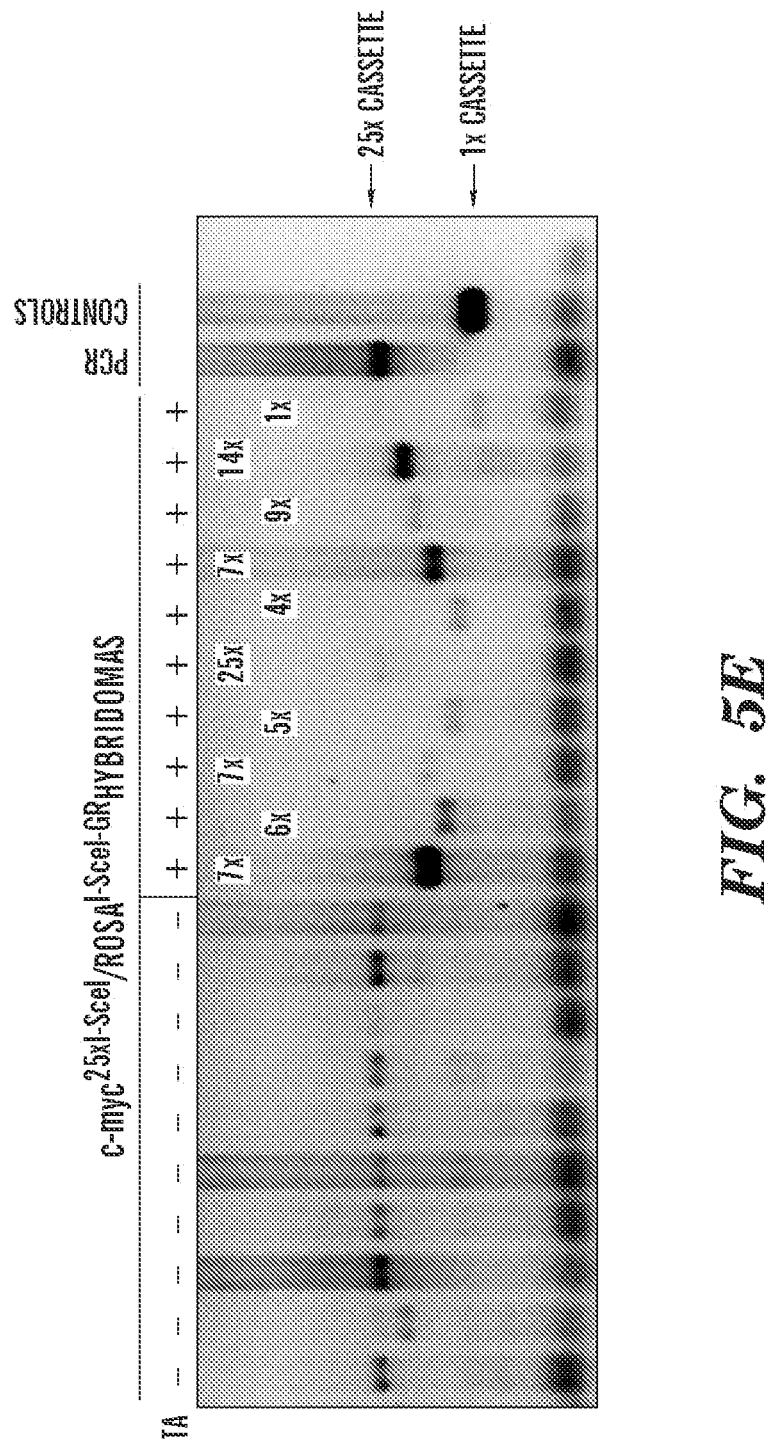

FIGS. 5A-5E show generation and characterization of ROSAI-SceI-GR mice (refers to FIG. 1). FIG. 5A shows that the ROSAI-SceI-GR allele was generated by homologous recombination into 129/Sv (TC1) ES cells of the indicated construct. The I-SceI-GR-IREStdT cassette was targeted into the intron 1 of the Rosa26 locus. Position of probe used for ES cell screening by Southern blotting is indicated. FIG. 5B shows a Southern blot analysis of DNA from a targeted clone before and after Neo-deletion. DNA was digested with EcoRI and probed with the 5' probe indicated in (FIG. 5A). FIG. 5C shows primary B cells from ROSAI-SceI-GR targeted mice express the Tomato red fluorescent protein as detected by cytofluorometry. B cells were activated for 4 days with αCD40/IL4. CSR was evaluated by staining with αB220 and αIgG1 antibodies. FIG. 5D) shows efficient I-SceI target sequence cutting by the I-SceI-GR protein. B cells from c-myc25xI-SceI/ROSAI-SceI-GR mice were activated for 4 days by αCD40/IL4. Addition of TA to the culture at day 1 induced cutting and rejoining in the 25x I-SceI cassette, as shown by disappearance of the full-length PCR product and presence of a smear of shorter fragments in day 4 DNA samples from treated cells. Control PCR amplification was conducted on plasmids containing either 25 or 1 I-SceI site(s). A diagram showing position of PCR primers is presented on top. FIG. 5E shows that the c-myc25x I-SceI cassette was PCR amplified as in FIG. 5D from hybridomas established from B cells stimulated as in (FIG. 5D). PCR products were cloned and sequenced. The residual numbers of I-SceI sites present in each clone is indicated.

Figures 6A, 6B, 6C, 6D:
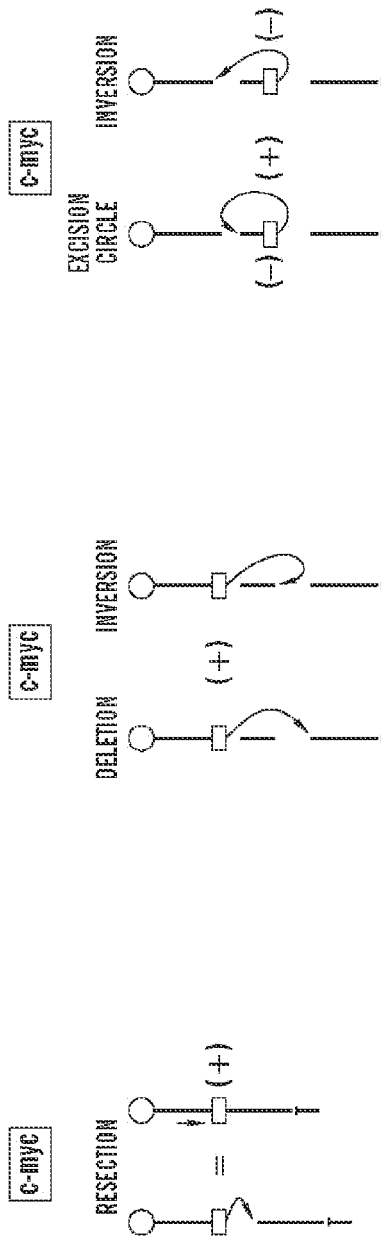

FIGS. 6A-6J show origin and distribution of (+) and (−) orientation junctions in HTGTS libraries. FIG. 6A-H show diagrams showing outcome of different types of joining events identified in HTGTS libraries following I-SceI-mediated DSBs in c-myc (FIGS. 6A-6D) and IgH (FIGS. 6E-6H) loci. FIG. 6A, FIG. 6E: single DSB and resection; FIG. 6B, FIG. 6F: intrachromosomal translocations to a second DSB 3' to the sequencing primers; FIG. 6C, FIG. 6G: intrachromosomal translocations to a second DSB 5' to the sequencing primers; FIG. 6D, FIG. 6H: interchromosomal translocations. I-SceI substrates are shown as yellow boxes. Sequencing primers are indicated. (FIG. 6I and FIG. 6J) Graphs showing the distribution of junctions in the chromosomal (+) (black bars) and (−) (white bars) orientation in c-myc25xI-SceI (FIG. 6J) and ΔSγ12xI-SceI HTGTS libraries. Data are presented as average of three HTGTS libraries ±SEM in FIG. 6J and of two HTGTS libraries.

DETAILED DESCRIPTION

We provide methods for analysis of whole genomes for all possible translocation events arising from a DNA double strand break (DSB).

The methods are based on our development of high throughput, genome-wide translocation sequencing (HTGTS) approach to elucidate translocation mechanisms in mammalian cells. The methods of the invention can be applied similarly to plant cells.

To exemplify the effectiveness of the HTGTS system, we employed the HTGTS to identify hundreds of thousands of independent translocation junctions ("the translocatome") emanating from fixed I-SceI meganuclease-generated DNA double strand breaks (DSBs) within the c-myc oncogene or IgH loci of B lymphocytes induced for Activation Induced-cytidine Deaminase (AID)-dependent IgH class-switching. DSBs translocated widely across the genome, but were preferentially targeted to transcribed chromosomal regions and also to numerous AID-dependent and AID-independent hotspots, with the latter being comprised mainly of cryptic genomic I-SceI targets.

We developed high throughput, genome-wide translocation sequencing (HTGTS) to isolate junctions between a chromosomal DSB introduced at a fixed site and other sequences genome-wide. Other than from resection at the fixed break (see below), such junctions are expected to result mostly from end-joining of introduced DSBs to other genomic DSBs. Thus, HTGTS also identifies DSBs throughout the genome capable of joining to any given fixed DSB.

Figure 1A:
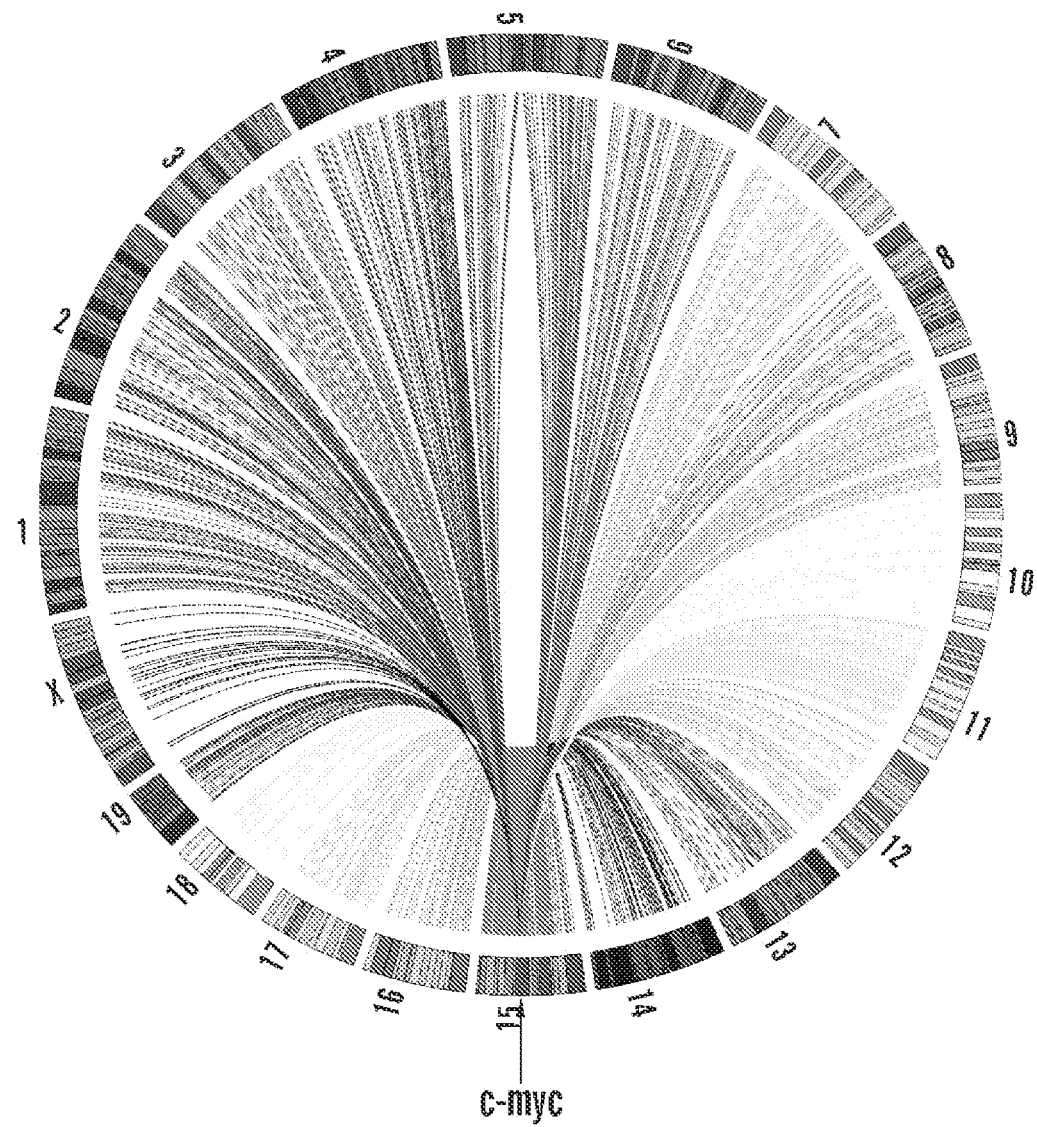
FIGS. 1A-1F show high throughput genomic translocation sequencing of primary mouse B cells. Circos plots showing the genome-wide landscape of rearrangements from representative c-myc (FIG. 1A) or IgH (FIG. 1B) HTGTS libraries were created. Chromosome ideograms comprise the circumference. Individual translocations were represented as arcs originating from specific I-SceI generated breaks and terminating at the partner site.
Figure 1B:
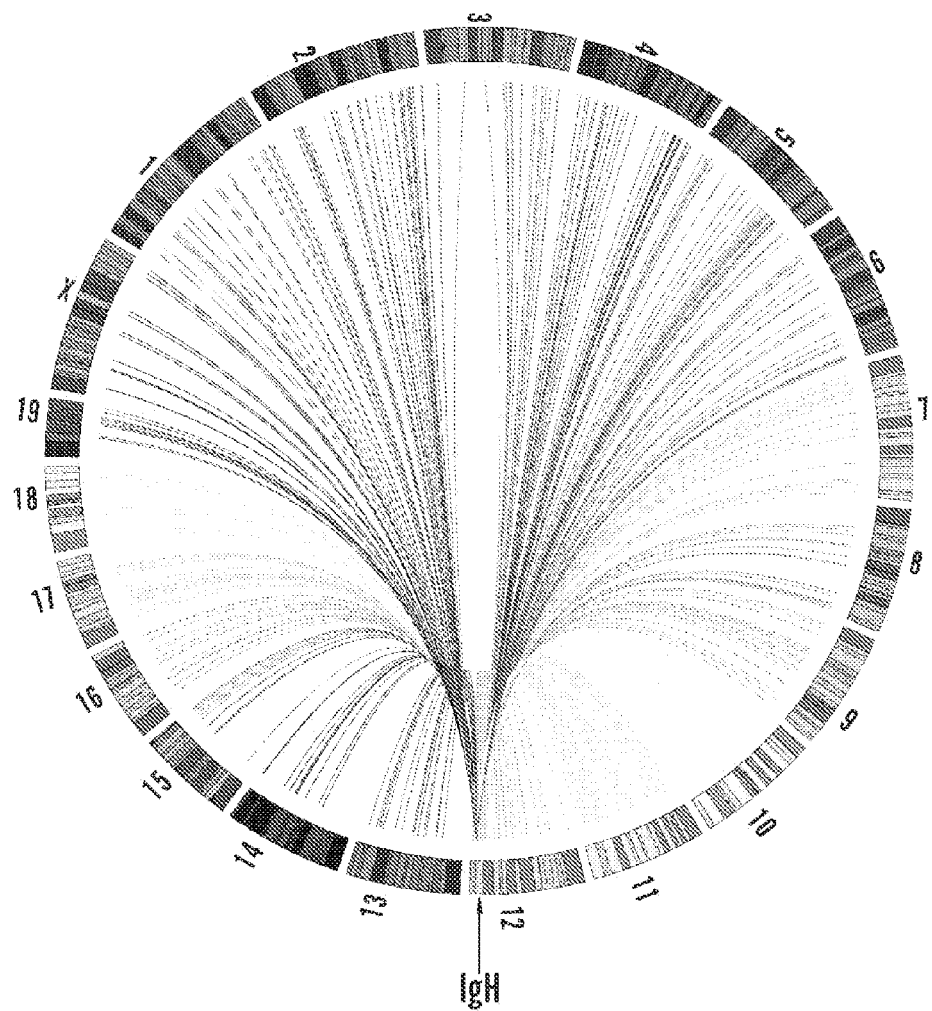

To show how the HTGTS works, we isolated from primary mouse B cells and analyzed more than 150,000 independent junctions resulting from fusion of DSBs in IgH or c-myc to sequences distributed widely across the genome (FIGS. 1A and B). The c-myc and IgH loci were chosen because they participate in recurrent oncogenic translocations in human and mouse B cell lymphomas. Any site of interest can be chosen using the same principles of the method, and any cell can be used to study the effects of agents causing or suspected of causing DSBs.

To target DSBs in our exemplary system, we employed an 18 bp canonical I-SceI meganuclease target sequence, which is absent in mouse genomes (Jasin, 1996). If one wishes to study another enzyme or break target sequence, such can be used instead of the I-SceI meganuclease as a target sequence. One can also perform the analysis with sequences that are suspected to be present only once or a few times in the genome, and without introduction of additional cassettes into the genome.

Figure 1C:
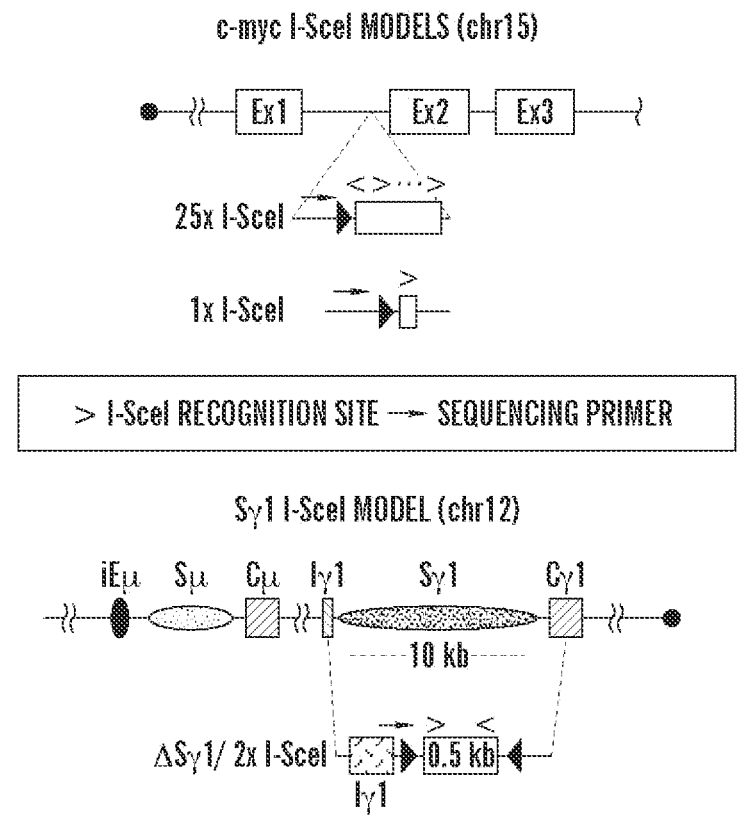

One c-myc target was a cassette with 25 tandem I-SceI sites within c-myc intron 1 on chromosome (chr) 15 (termed c-myc25xI-SceI; FIG. 1C). We employed 25 tandem I-SceI sites to increase cutting frequency (Wang et al., 2009). Retrovirally-expressed I-SceI enzyme in activated B cells harboring the c-myc25xI-SceI increased IgH/c-myc translocations 100-fold (Wang et al., 2009). For comparison, we employed an allele with a single I-SceI site in the same position (termed: c-myc1xI-SceI) that showed moderately less cutting (FIG. 1C; FIG. S1). For IgH, we employed an allele with two I-SceI sites in place of the 10-kb endogenous S71 (termed ΔSγ12xI-SceI) on chr12 (Zarrin et al., 2007). Thus, one can use any number of target sites raging from one, 2, 3, 4, 5, 6, 7, 8, 9, 10, 1-10, 2-10, 1-25, 2-25, 5-25, 5-30, 1-30 to 1-50 or at least 5, at least 10, at least 15, at least 20, at least 25 or at least 50. In some aspects of all the embodiments of the invention, the number of target sites is between 1 and 25, inclusive.

One can expose the nucleus of the cell to the DSB-causing agent, such as the enzyme we used in our experiments, using any method that provides delivery of the enzyme to the nucleus or activation of an enzyme present in an inactive state in the cell, such as enzymes fused to hormone regulatory subunits such as estrogen receptor (ER) or glucocorticoid receptor (GR) or other well known hormone receptors. One method is to use a retrovirus engineered to express the agent, such as an enzyme.

Retroviruses are an efficient means to deliver single DNA expression constructs to a wide range of mammalian cell types. They are by far the easiest and fastest means to deliver genes stably to mammalian cells. Examples of retroviruses that can be used in the methods of the invention include vectors based on Moloney Murine Leukemia Virus (MMLV) which typically allows for delivery of genes to most dividing mammalian cell types. If the cell to be studied is a non-dividing cell, vectors based on lentiviruses such a feline immunodeficiency virus or human immune deficiency virus may be used.

One can also use other viruses, such as adenoviruses and adeno-associate viruses as delivery vehicles. Small molecules, including chemical agents may also be used without a specific carrier as they will pass through the membranes and reach the nucleus without particular carriers. One can also use physical exposure to gamma or UV irradiation without particular carriers.

Figure 1D:

As a model cellular system, we employed primary splenic B cells activated in culture with αCD40 plus IL4, which induces AID expression, transcription, DSBs and CSR at Sγ1 (IgG1) and Sε (IgE), during days 2-4 of activation. At 24 hours, we infected B cells with I-SceI-expressing retrovirus to induce DSBs at I-SceI targets (Zarrin et al., 2007). Cells were processed at day 4 to minimize doublings and potential cellular selection. As high-titer retroviral infection can impair non homologous end-joining (NHEJ) (Wang et al., 2009), we also assayed B cells that express from their Rosa26 locus an I-SceI-glucocorticoid receptor fusion protein (I-SceI-GR) that can be activated via triamcinolone acetonide (TA) treatment (FIG. 1D). The c-myc25xI-SceI cassette was frequently cut in TA-treated c-myc25xI-SceI/ROSAI-SceI-GR B cells and hybridomas derived from them.

Similarly, one can use any eukaryotic target cell. In some aspects of all the embodiments of the invention, the target cell is a mammalian cell, such as human cell. Cell can be of any type, so long as it contains DNA, and can be maintained in culture. The cell can be a primary cell or an immortalized cell. One can also use differentiated cells as well as partially differentiated cells, pluripotent cells and stem cells, including embryonic stem cells.

Cell division is not strictly necessary to induce a DSB and translocations. However, if cells are T or B cells, activation of T and B cells helps to keep them alive in the culture for 4 days, to allow retroviral infection and to induce expression of DSB-generating enzymes (such as AID in B cells). Translocation per se can be obtained also in non-cycling G1 arrested cells. Accordingly, in some aspects of all the embodiments of the invention, the cells are non-dividing cells.

In some instances, if one uses cells, such as T or B cells or machrophages, such cells can be activated using respective activating conditions well known to one skilled in the art to induce cell division and recombination events.

In some aspects of all the embodiments of the invention, the target cell is a plant cell.

For example, one can use embryonic stem (ES) cells. ES cells are of relevance because they represent undifferentiated cells in which maintenance of genomic integrity relies substantially on homologous recombination (HR). Understanding the principles that govern translocations in this cell type also might be extended to induced pluripotent stem (iPS) cells, which share some characteristics with ES cells and are promising therapeutic tools for certain human diseases. For the HTGTS studies, we have generated ES cells expressing I-SceI-GR and which are targeted with either the I-SceI/Sγ1 or the I-SceI/c-myc cassette. We have shown that we can efficiently induce DSBs in these cells after TA treatment.

One can also use neuronal cells. Neuronal cells are of relevance because we have previously showed their survival during proliferative phases of CNS development relies on classical NHEJ (C-NHEJ), suggesting they undergo high levels of DSBs due to metabolic or other unknown factors (Gao et al., Cell, 1998; Frank et al., Nature, 2000). In addition, they have shown that inactivation of C-NHEJ factors, such as XRCC4, in neuronal progenitor cells in a p53-deficient background led to medulloblastomas with recurrent translocations (Yan et al., 2006). These cells can be analyzed, e.g., using neurosphere cultures from mouse models and either infect them with I-SceI retrovirus or induce I-SceI-GR activity for the HTGTS.

Another example of cell types included fibroblasts. Fibroblasts offer the opportunity to investigate effects of nuclear geometries on genome-wide positions of the chromosomes and on translocation patterns.

For genome-wide isolation of junctions between DSBs in targeted I-SceI sites and other DSBs, we employed two different approaches.

Figures 1E, 1F:
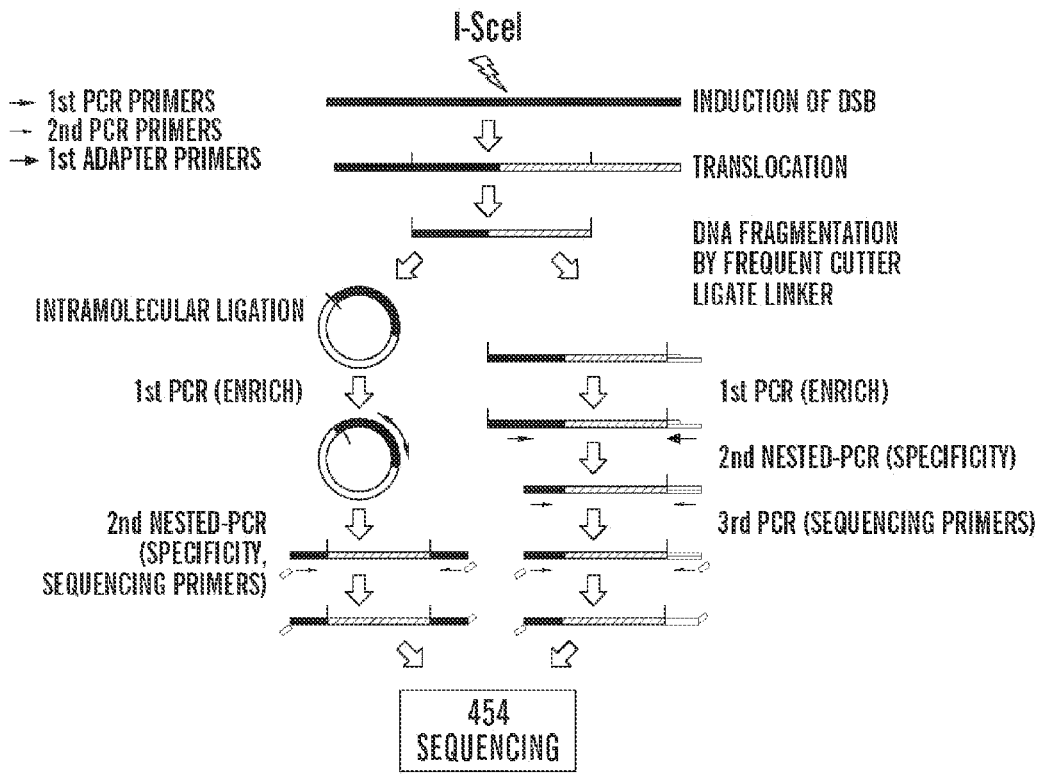

For the adapter-PCR approach illustrated in FIG. 1E, and adapted from Siebert et al., 1995, genomic DNA that had been treated with a DSB-causing agent, was fragmented with a frequently cutting restriction enzyme, which based on target distribution in the mouse genome should allow cloning of 90% or more of potential junctions.

Frequently cutting enzymes, which typically cut every 4 bp are well known to one skilled in the art and one can screen for any their effect on a target genome in silico using a target genome sequence as a template. In the examples we used, for example, MspI, but a skilled artisan can easily substitute the enzymes according to the need for any given genome.

Following digestion, we ligated an asymmetric adapter to the fragmented DNA and digested products with I-SceI or other enzymes to block amplification of germline or unrearranged targeted alleles in subsequent PCR steps. Blocking enzymes typically need to be selected in each individual case based on the DNA sequence of the locus where the target cassette, such as the I-SceI cassette is located, or based on the artificial sequence of the I-SceI cassette itself—any common restriction enzyme that cuts in the unrearranged product past the enzyme restriction site, such as I-SceI restriction site, and therefore should be absent from the translocated product, can be used as a blocking enzyme. The selection is routine and based on each individual sequence. Thus, a skilled artisan can readily find a suitable blocking enzyme for the assays.

The asymmetric primer design has also been published. In general, the primer is designed to anneal to the DNA end generated by the frequently cutting restriction enzyme and contains a stretch of known DNA sequence that can be used to design PCR primers for subsequent amplification reactions, such as the nested PCR.

Adapter primers are designed based on the adapter sequences, and are typically about 15-25 bp long. Design of PCR primers is routine.

We then performed three rounds of nested-PCR with adapter- and locus-specific primers. Depending on the locus-specific PCR primers, one or the other side of the I-SceI DSB provides the "bait" translocation partner (FIG. 1C), with the "prey" provided by DSBs generated at other genomic sites. PCR products were sequenced via 454 Roche next-generation sequencing.

In theory, there is not a minimum or a maximum for how many rounds of nested PCR can be used. However, typical nested PCR reactions benefit from 2-3 rounds. More rounds will be useless since they will just increase the amplification of already overrepresented sequences—Nested PCR (with typically 2 rounds) is used to increase specificity of the amplification reaction, by using independent sets of primers for the same locus. In our examples we used the third round simply to add the barcodes necessary for the 454 sequencing. The third round can be skipped if barcoded primers are used at round 2 or if one uses other sequencing methods where additional bar codes are not needed. In some aspects of all the embodiments of the invention, one performs 2 rounds of nested PCR and an additional round to introduce a tag or a label into the PCR products thus allowing a specific sequencing protocol to be applied to analyze the sequences of the junctions.

In theory any sequencing method can be used in the methods of the invention. We have used methods ranging from standard Sanger sequencing methods to next generation sequencing. Typically, better, faster, and less expensive results are obtained using the next generation sequencing methods. For the analysis of the results, it is also important to be able to have reads that are long enough to reach the actual translocation junction. Therefore, sequencing methods that fulfill these requirements are optimal for the use in the methods of the invention.

As a second approach, we employed circularization-PCR (FIG. 1E; adapted from Mahowald et al., 2009). Using this method, enzymatically fragmented DNA was ligated at a concentration favoring intra-molecular ligation, digested with blocking enzymes, and nested-PCRs performed with locus-specific primers.

In general this method is similar to the one that uses the method adapted from Sievert in the analysis, and it has the same goal. However, the first steps are different and instead of using adapters and primers designed on the adapters, the method uses two sets of locus-specific primers. This may increase the specificity of the reactions, and may be better suited in some cases.

In the ligation step, typically, one uses DNA that is concentrated at less than 1.5 ng/microL. Concentrations varying from about 1.0 to about 2.5 ng/microL can be used and a skilled artisan will be able to optimize the DNA concentrations using routine methods.

We further developed computer programs to align HTGTS junctions we had identified to reference genomes and obviate potential artifacts, including junctions generated during in vitro ligation, mis-assigned highly repetitive sequences, junctions from PCR mis-priming, or identical junctions in a given library.

While BLAST method can be used, generally, the most useful alignment is based on the BLAT software from UCSC (http "colon""forward slash""forward slash" genome"dot" ucsc "dot" edu/FAQ/FAQblat "dot" html).

Blat is an alignment tool like BLAST, but it is structured differently. On DNA, Blat works by keeping an index of an entire genome in memory. Thus, the target database of BLAT is not a set of GenBank sequences, but instead an index derived from the assembly of the entire genome. The index—which uses less than a gigabyte of RAM—consists of all non-overlapping 11-mers except for those heavily involved in repeats. This smaller size means that Blat is far more easily mirrored. Blat of DNA is designed to quickly find sequences of 95% and greater similarity of length 40 bases or more. It may miss more divergent or short sequence alignments.

DNA BLAT works by keeping an index of the entire genome (but not the genome itself) in memory. Since the index takes up a bit less than a gigabyte of RAM, BLAT can deliver high performance on a reasonably priced Linux box. The index is used to find areas of probable homology, which are then loaded into memory for a detailed alignment.

We experimentally controlled for potential background from various sources including in vitro ligation, PCR template switching, and data analysis. As one control, we mixed unrelated human DNA with mouse DNA from activated, I-SceI-infected c-myc25xI-SceI or $\Delta$S$\gamma$12xI-SceI B cells and generated HTGTS libraries. Junctions fusing mouse and human sequences were less than 1% of the total for c-myc25xI-SceI or $\Delta$S$\gamma$12xI-SceI libraries and for libraries made via either method, demonstrating assay specificity (FIG. 1F).

Examples of parameters that can be used include the following:

Total Reads: Total raw reads we get from the sequencing facility.

Unique Alignment: Total number of reads (Qname) with any type of alignment (down to 30 bp).

Total Alignment: Each read (Qname) may have multiple alignments. This number represents the total alignments we get from all the align-able reads.

Clean Margin: Looks for frequent cutter within 10 bp upstream of the translocation and 5 bp downstream of translocation. This 10/5 ratio was originally because of greater chance of by deletion upstream of the "false" translocation rather than by addition the other direction.

Min Match: A valid alignment should have an alignment score (match—mismatch) of >30.

Rest Number: Can be used, but typically we do not use this filter for the method.

Red Primer: Checking for the presence of red primer+4 bp of red.cont. Allowing for 1 mismatch.

Blue Primer: Checking for the presence of blue primer+4 bp of blu.cont. Allowing for 1 mismatch.

Same Blat Score: If one read(Qname) has multiple alignments, and the score.diff is <=3, then we removed the alignments.

Top Blat Score: If one read(Qname) has multiple alignments, we only keep the one with the highest Blat Score.

MultiPCR: If two alignments align to the same junction site (Tstart for a "+" strand alignment, and Tend for a "−" strand alignment), and the Qstart (the start of the junction in the raw sequence) differential is less than 3 bp, we will consider them as PCRrepeat of each other.

RestSite: If the alignment starts after the presence of a restriction site in the raw sequence, we remove it. [Qstart (Restriction site)<=Qstart(Alignment)]

Tgap bases: If the alignment has > or =10 bp of gap (Tgap) within the genomic alignment, the alignment is removed (excludes breaksite Chr and Chr12 for the mouse IgH locus)

Alignment Count: If one read has more than 20 alignments the read is removed.

PCRrept1: ### 1) Read output files from TLPalign good output files ### Create a new fasta(fna) file from the for Chr12 reads from the good output files ### 2) Run BLAT alignment against SV129 (NT114985.2) ### 3) Parse the output PSLX file (with unique Qname, Qstart, and min (Tgap)) and then generate a 'perfilter' file ### 4) Called TLPPCRrept.pl to filter the PCRRept seq with Qsize<=3, Qstart<=2.

PCRrept2: #>read a text file contains repetitive sequences that are rich in Chr12 #>takeout the ones that have same Repeat_cnt and position of the match seq is <=3 bp The analysis is typically performed by a non-human machine, such as a computer executing a computer readable software that allows rapid alignment of the sequences along the template genome.

Naturally, one must first have a template genome, so if one is not available on the databases, one can first sequence the genome and then perform the analysis of the DSB producing or inducing agents, such as enzymes.

Meganucleases

Examples of agents that can be used to create a double-stranded DNA break or DSB include meganucleases.

Thus, the methods of the invention can be used to evaluate the universe of recombination events a DSB caused by a meganuclease. Such screening of meganucleases would assist in selecting meganucleases for the purpose of genetic and genomic engineering. If one finds, for example, an enzyme that results in particularly large number of recombinations or particularly troublesome recombinations, e.g., a possibility to disrupt a gene disruption of which would lead to increased risk of malignant transformation, one can avoid using such meganucleases.

Any meganuclease, existing or newly engineered one, can be used in the methods as described using the recognition sequence as described in the methods.

Meganucleases are sequence-specific endonucleases originating from a variety of single-celled organisms such as Archaea or archaebacteria, bacteria, phages, fungi, yeast, algae and some plant organelles. Meganucleases have long recognition sites of between about 12 and 40 base pairs. As a result the recognition site generally occurs only once in any given genome. The high degree of specificity of these proteins makes them the perfect tools for genome customization: a meganuclease binding to its specific DNA recognition site induces a DNA double-strand break (DSB) at a unique site in the genome of a living cell. For example, the 18-base pair sequence recognized by the I-SceI meganuclease would on average require a genome twenty times the size of the human genome to be found once by chance (although sequences with a single mismatch occur about three times per human-sized genome). Meganucleases are therefore considered to be the most specific naturally occurring restriction enzymes.

To date, about 600 meganucleases, from various unicellular organisms, have been identified and sequenced. However, the naturally occurring meganucleases have also been engineered for genome customization products. For example, meganucleases with 18-24 bp long recognition sites are commercially available.

Meganucleases are mainly represented by two main enzyme families collectively known as homing endonucleases: intron endonucleases and intein (intervening sequences that are spliced and excised post-translationally) endonucleases.

In nature, these proteins are coded by mobile genetic elements, introns or inteins. Introns propagate by intervening at a precise location in the DNA, where the expression of the meganuclease produces a break in the complementary intron- or intein-free allele. For inteins and group I introns, this break leads to the duplication of the intron or intein at the cutting site by means of the homologous recombination repair for double-stranded DNA breaks.

There are five families, or classes, of homing endonucleases (Stoddard B L., Homing endonuclease structure and function. Q Rev Biophys. 2005 February; 38(1):49-95. Epub 2005 Dec. 9.) Among meganucleases, the LAGLIDADG family of homing endonucleases is the most studied and well known family, and it has become a valuable tool for the study of genomes and genome engineering. It is mostly found in the mitochondria and chloroplasts of eukaryotic unicellular organisms. By modifying the recognition sequence of these enzymes through protein engineering, the targeted sequence can be changed. Meganucleases are used to modify all genome types, whether bacterial, plant or animal. They can be used, for example, to correct mutated genes.

The thus far best characterized endonucleases which are most widely used in research and genome engineering include I-SceI (discovered in the mitochondria of baker's yeast *Saccharomyces cerevisiae*), I-CreI (from the chloroplasts of the green algae *Chlamydomonas reinhardtii*) and I-DmoI (from the archaebacterium *Desulfurococcus mobilis*).

The best known LAGLIDADG endonucleases are homodimers (for example I-CreI, composed of two copies of the same protein domain) or internally symmetrical monomers (I-SceI). The DNA binding site, which contains the catalytic domain, is composed of two parts on either side of the cutting point. The half-binding sites can be extremely similar and bind to a palindromic or semi-palindromic DNA sequence (I-CreI), or they can be non-palintromic (I-SceI).

To create tailor-made meganucleases, two main approaches have been adopted: (1) Modifying the specificity of existing meganucleases by introducing a small number of variations to the amino acid sequence and then selecting the functional proteins on variations of the natural recognition site (Mutations altering the cleavage specificity of a homing endonuclease. Seligman L M, et al., Nucleic Acids Res. 2002 Sep. 1; 30(17):3870-9; Sussman et al. Journal of Molecular Biology. 342:31-41, 2004; Rosen L E, et al. (2006) Homing endonuclease I-CreI derivatives with novel DNA target specificities. Nucleic Acids Research. 34:4791-4800); and (2) by exploiting a property that plays an important role in meganucleases' naturally high degree of diversification: the possibility of associating or fusing protein domains from different enzymes (Arnoud S, et al. (2006) Engineering of Large Numbers of Highly Specific Homing Endonucleases that Induce Recombination on Novel DNA Targets. Journal of Molecular Biology. 355:443-458; Smith J. et al., (2006) A combinatorial approach to create artificial homing endonucleases cleaving chosen sequences. Nucleic Acids Research. 34(22):e149. This option makes it possible to develop chimeric meganucleases with a new recognition site composed of a half-site of meganuclease A and a half-site of protein B. By fusing the protein domains of I-DmoI and I-CreI, two chimeric meganucleases have been created using this method: E-Drel and DmoCre (Chevalier BS., et al., 2002) Design, activity, and structure of a highly specific artificial endonuclease. Mol Cell. 10(4):895-905). These two approaches can be combined to increase the possibility of creating new enzymes, while maintaining a high degree of efficacy and specificity research laboratories and for industrial purposes.

For example, over 20,000 protein domains from the homodimeric meganuclease I-CreI as well as from other meganucleases scaffolds have been developed by commercial entities (Grizot S et al., Nucleic Acids Res. 2010 April; 38(6):2006-18. Epub 2009 Dec. 21). Precision Biosciences, a biotechnology company, has developed a fully rational design process called Directed Nuclease Editor (DNE) which is capable of creating engineered meganucleases that target and modify a user-defined location in a genome (Gao et al., Heritable Targeted Mutagenesis in Maize Using a Dedicated Meganuclease. Plant J. 2010 January; 61(1):176-87. Epub 2009 Oct. 7).

Evaluating the recombination events any meganuclease sequence can result in would provide important information regarding the genomic effects of using the meganuclease for any genetic or genomic engineering application.

Zinc-finger Nucleases

Agents that produce DSBs or are suspected of being capable of producing DSBs can also be zinc-finger nucleases.

Zinc-finger nucleases (ZFNs) are artificial restriction enzymes generated typically by fusing a zinc finger DNA-binding domain to a DNA-cleavage domain. Zinc finger domains can be engineered to target desired DNA sequences and this enables zinc-finger nucleases to target unique sequences within complex genomes. By taking advantage of endogenous DNA repair machinery, these reagents can be used to precisely alter the genomes of higher organisms.

Zinc finger nucleases have become useful reagents for manipulating the genomes of many plants and animals including *arabidopsis*, tobacco, soybean, corn, *Drosophila melanogaster*, *C. elegans*, sea urchin, silkworm, zebrafish, frogs, mice, rats, rabbits, pigs, cattle, and various types of mammalian cells. Zinc finger nucleases have also been used in a mouse model of haemophilia and an ongoing clinical trial is evaluating Zinc finger nucleases that disrupt the CCR5 gene in CD4+ human T-cells as a potential treatment for HIV/AIDS. ZFNs are also used for the creation of a new generation of genetic disease models called isogenic human disease models.

Given the breath of potential applications for these enzymes for disabling alleles, editing alleles and gene therapy, the methods of the present invention provide an invaluable tool to screen for the most specific enzymes for any particular genome or genomic application.

Thus, the methods of the invention can also be used to analyze various zinc-finger nucleases for specificity of cutting and their effect on recombinations throughout the genome.

TAL Effector Nucleases or TALEN™

Agents that produce DSBs or are suspected of being capable of producing DSBs can also be TALENs.

TALENs™ are a class of sequence-specific nucleases created by the fusion of transcription activator-like effectors (TALEs) to the catalytic domain of an endonuclease. TALENs are genome customization tools that can be used for gene-specific modifications and disruptions (see, e.g., Ting Li, et al. Nucleic Acids Research, 2011, Vol. 39, No. 1 359-372; Feng Zhang, et al. Nature biotechnology Letters: published online 19 Jan. 2011).

TALEs were first discovered in the plant pathogen, *Xanthomonas*. TALEs specifically bind to DNA and regulate plant genes during infection by the pathogen.

Each TALE contains a central repetitive region consisting of varying numbers of repeat units of typically 33-35 amino acids. It is this repeat domain that is responsible for specific DNA sequence recognition. Each repeat is almost identical with the exception of two variable amino acids termed the repeat-variable diresidues. The mechanism of DNA recognition is based on a code where one nucleotide of the DNA target site is recognized by the repeat-variable diresidues of one repeat.

A TALEN™ is composed of a TALE DNA binding domain for sequence-specific recognition fused to the catalytic domain of an endonuclease that introduces double strand breaks (DSB). The DNA binding domain of a TALEN™ is capable of targeting with high precision a large recognition site (for instance 17 bp).

A TALEN™ is defined as a heterodimer (2 units of a TALE DNA binding domain fused to a catalytic domain) cleaving two close sequences, resulting in increased specificity.

The methods of the invention are optimal also for analysis of TALENs for specificity and recombination events throughout the genome. For example, novel TALENs can be analyzed for their sequence specificity.

Chemical Agents as DSB Inducing Agents

One can also use the method of the present invention to identify hotspots for DSBs and recombinations as a result of a cell's exposure to a chemical agent, such as a chemotherapy agent.

Any chemical agent can be used as an agent that is "suspected of causing" DSBs in the screens of the invention. Such an analysis allows one to detect and determine the translocatome of any given cell if it is exposed to such a chemical agent.

The technical method to generate high throughput, genome-wide translocation sequencing (HTGTS) will be the same as described above when using a chemical agent. Based on the translocation pattern obtained after incubation with a DSB causing agent, it is then possible to locate DSBs hotspots induced by the agent.

EXAMPLES

The following examples are provided to illustrate some applications of the claimed method and its use in analysis of cell genomes in mammalian cells. The examples are not to be considered limiting, e.g., other genomes than the illustrated ones, other enzymes than the illustrated ones and other analysis methods than the illustrated ones may be employed with the same principles as generally explained in the examples and the detailed description.

Example 1

While chromosomal translocations are common pathogenetic events in cancer, mechanisms that promote them are poorly understood. To elucidate translocation mechanisms in mammalian cells, we developed high throughput, genome-wide translocation sequencing (HTGTS). We employed HTGTS to identify tens of thousands of independent translocation junctions involving fixed I-SceI meganuclease-generated DNA double strand breaks (DSBs) within the c-myc oncogene or IgH locus of B lymphocytes induced for Activation Induced-cytidine Deaminase (AID)-dependent IgH class-switching. DSBs translocated very widely across the genome, but were preferentially targeted to transcribed chromosomal regions and also to numerous AID-dependent and AID-independent hotspots, with the latter being comprised mainly of cryptic genomic I-SceI targets. Comparison of translocation junctions with genome-wide nuclear run-ons revealed a marked association between transcription start sites and translocation targeting. The majority of translocation junctions were formed via end-joining with short micro-homologies. We discuss implications of our findings for diverse fields including gene therapy and cancer genomics.

Recurrent oncogenic translocations are common in hematopoietic malignancies including lymphomas (Kuppers and Dalla-Favera, 2001) and also occur frequently in solid tumors such as prostate and lung cancers (Shaffer and Pandolfi, 2006). DNA double-strand breaks (DSBs) are common intermediates of these genomic aberrations (Stratton et al., 2009). DSBs are generated by normal metabolic processes, by genotoxic agents including some cancer therapeutics, and by V(D)J and immunoglobulin (Ig) heavy (H) chain (IgH) class switch recombination (CSR) in lymphocytes (Zhang et al., 2010). Highly conserved pathways repair DSBs to preserve genome integrity (Lieber, 2010). Nevertheless, repair can fail, resulting in unresolved DSBs and translocations. Recurrent translocations in tumors usually arise as low frequency events that are selected during oncogenesis. However, other factors influence the appearance of recurrent translocations including chromosomal location of oncogenes (Gostissa et al., 2009). Chromosomal environment likely affects translocation frequency by influencing mechanistic factors, including DSB frequency at translocation targets, factors that contribute to juxtaposition of broken loci for joining, and mechanisms that circumvent repair functions that promote intra-chromosomal DSB joining (Zhang et al., 2010).

IgH CSR is initiated by DSBs that result from transcription-targeted AID-cytidine deamination activity within IgH switch (S) regions that lie just 5' of various sets of CH exons. DSBs within the donor Sµ region and a downstream acceptor S region are fused via end-joining to complete CSR and allow expression of a different antibody class (Chaudhuri et al., 2007). Clonal translocations in human and mouse B cell lymphomas often involve IgH S regions and an oncogene, such as c-myc (Kuppers and Dalla-Favera, 2001; Gostissa et al., 2011). In this regard, AID-generated IgH S region DSBs directly participate in translocations to c-myc and other genes (Franco et al., 2006; Ramiro et al., 2006; Wang et al., 2009). Through its role in somatic hypermutation (SHM) of IgH and Ig light (IgL) variable region exons, AID theoretically might generate lower frequency DSBs in Ig loci that serve as translocation intermediates (Liu and Schatz, 2009). In addition, AID mutates many non-Ig genes in activated B cells at far lower levels than Ig genes (Liu et al., 2008), such off-target AID activity also may contribute to translocations of non-Ig genes (Robbiani et al., 2008). Indeed, AID even has been suggested to initiate lesions leading to translocations in non-lymphoid cancers, including prostate cancer (Lin et al., 2009). However, potential roles of AID in generating DSBs genome-wide has not been addressed. In this regard, other sources of translocation-initiating DSBs could include intrinsic factors, such as oxidative metabolism, replication stress, and chromosome fragile sites, or extrinsic factors such as ionizing radiation or chemotherapeutics (Zhang et al., 2010).

DSBs lead to damage response foci formation over 100 kb or larger flanking regions, promoting DSB joining and suppressing translocations (Zhang et al., 2010; Nussenzweig and Nussenzweig, 2010). IgH class-switching in activated B cells can be mediated by yeast I-SceI endonuclease-generated DSBs without AID or S regions, suggesting general mechanisms promote efficient intra-chromosomal DSB joining over at least 100 kb (Zarrin et al., 2007). In somatic cells, classical non-homologous end-joining (C-NHEJ) repairs many DSBs (Zhang et al., 2010). C-NHEJ suppresses translocations by preferentially joining DSBs intra-chromosomally (Ferguson et al., 2000). Deficiency for C-NHEJ leads to frequent translocations, demonstrating that other pathways fuse DSBs into translocations (Zhang et al., 2010). Correspondingly, an alternative end-joining pathway (A-EJ), that prefers ends with short micro-homologies (MHs), supports CSR in the absence of C-NHEJ (Yan et al., 2007) and joins CSR DSBs to other DSBs to generate translocations (Zhang et al., 2010). Indeed, C-NHEJ suppresses p53-deficient lymphomas with recurrent IgH/c-myc translocations catalyzed by A-EJ (Zhu et al., 2002). Various evidence suggests A-EJ may be translocation prone (e.g. Simsek and Jasin, 2010).

The mammalian nucleus is occupied by non-randomly positioned genes and chromosomes (Meaburn et al., 2007). Fusion of DSBs to generate translocations requires physical proximity; thus, spatial disposition of chromosomes might impact translocation patterns (Zhang et al., 2010). Cytogenetic studies revealed that certain loci involved in oncogenic translocations are spatially proximal (Meaburn et al., 2007). Studies of recurrent translocations in mouse B cell lymphomas suggested that aspects of particular chromosomal regions, as opposed to broader territories, might promote proximity and influence translocation frequency (Wang et al., 2009). Non-random position of genes and chromosomes in the nucleus led to two general models for translocation initiation. "Contact-first" poses translocations to be restricted to proximally-positioned chromosomal regions, while "breakage-first" poses that distant DSBs can be juxtaposed (Meaburn et al., 2007). In depth evaluation of how chromosomal organization influences translocations requires a genome-wide approach.

To elucidate translocation mechanisms, we have developed approaches that identify genome-wide translocations arising from a specific cellular DSB. Thereby, we have isolated large numbers of translocations from primary B cells activated for CSR, to provide a genome-wide analysis of the relationship between translocations and particular classes of DSBs, transcription, chromosome domains, and other factors.

Development of High Throughput Genomic Translocation Sequencing

We developed high throughput, genome-wide translocation sequencing (HTGTS) to isolate junctions between a chromosomal DSB introduced at a fixed site and other sequences genome-wide. Other than from resection at the fixed break (see below), such junctions are expected to result mostly from end-joining of introduced DSBs to other genomic DSBs. Thus, HTGTS also identifies DSBs throughout the genome capable of joining to any given fixed DSB.

To show how the HTGTS works, we isolated from primary mouse B cells and analyzed more than 150,000 independent junctions resulting from fusion of DSBs in IgH or c-myc to sequences distributed widely across the genome (FIGS. 1A and B). The c-myc and IgH loci were chosen because they participate in recurrent oncogenic translocations in human and mouse B cell lymphomas. Any site of interest can be chosen using the same principles of the method.

To target DSBs, we employed an 18 bp canonical I-SceI meganuclease target sequence, which is absent in mouse genomes (Jasin, 1996). One c-myc target was a cassette with 25 tandem I-SceI sites within c-myc intron 1 on chromosome (chr) 15 (termed c-myc25xI-SceI; FIG. 1C). We employed 25 tandem I-SceI sites to increase cutting frequency (Wang et al., 2009). Retrovirally-expressed I-SceI in activated B cells harboring the c-myc25xI-SceI increased IgH/c-myc translocations 100-fold (Wang et al., 2009). For comparison, we employed an allele with a single I-SceI site in the same position (termed c-myc1xI-SceI) that showed moderately less cutting (FIG. 1C; FIG. 4). For IgH, we employed an allele with two I-SceI sites in place of the 10-kb endogenous Sγ1 (termed ΔSγ12xI-SceI) on chr12 (Zarrin et al., 2007). As a model cellular system, we employed primary splenic B cells activated in culture with αCD40 plus IL4, which induces AID expression, transcription, DSBs and CSR at Sγ1 (IgG1) and Sε (IgE), during days 2-4 of activation. At 24 hours, we infected B cells with I-SceI-expressing retrovirus to induce DSBs at I-SceI targets (Zarrin et al., 2007). Cells were processed at day 4 to minimize doublings and potential cellular selection. As high-titer retroviral infection can impair C-NHEJ (Wang et al., 2009), we also assayed B cells that express from their Rosa26 locus an I-SceI-glucocorticoid receptor fusion protein (I-SceI-GR) that can be activated via triamcinolone acetonide (TA) treatment (FIG. 1D). The c-myc25xI-SceI cassette was frequently cut in TA-treated c-myc25xI-SceI/ ROSAI-SceI-GR B cells and hybridomas derived from them.

For genome-wide isolation of junctions between DSBs in targeted I-SceI sites and other DSBs, we employed two methods in the HTGTS analysis.

For the adapter-PCR approach (FIG. 1E, Siebert et al., 1995), genomic DNA was fragmented with a frequently cutting restriction enzyme, which based on target distribution in the mouse genome should allow cloning of 90% or more of potential junctions. Following digestion, we ligated an asymmetric adapter to the fragmented DNA and digested products with I-SceI or other enzymes to block amplification of germline or unrearranged targeted alleles in subsequent PCR steps. We then performed three rounds of nested-PCR with adapter- and locus-specific primers. Depending on the locus-specific PCR primers, one or the other side of the I-SceI DSB provides the "bait" translocation partner (FIG. 1C), with the "prey" provided by DSBs generated at other genomic sites. PCR products were sequenced via 454 Roche next-generation sequencing.

As a second approach, we employed circularization-PCR (FIG. 1E; Mahowald et al., 2009), in which enzymatically fragmented DNA was ligated at a concentration favoring intra-molecular ligation, digested with blocking enzymes, and nested-PCRs performed with locus-specific primers.

We also developed computer programs to align HTGTS junctions to reference genomes and obviate potential artifacts, including junctions generated during in vitro ligation, mis-assigned highly repetitive sequences, junctions from PCR mis-priming, or identical junctions in a given library.

We experimentally controlled for potential background from various sources including in vitro ligation, PCR template switching, and data analysis. As one control, we mixed human DNA with mouse DNA from activated, I-SceI-infected c-myc25xI-SceI or ΔSγ12xI-SceI B cells and generated HTGTS libraries. Junctions fusing mouse and human sequences were less than 1% of the total for c-myc25xI-SceI or ΔSγ12xI-SceI libraries and for libraries made via either method, demonstrating assay specificity (FIG. 1F).

We identified nearly 150,000 independent junctions from numerous independent libraries (each from a different mouse) for each mouse line with both approaches; in addition, for the c-myc25xI-SceI or ΔSγ12xI-SceI lines, junctions were isolated from wild-type (WT) and AID−/− backgrounds (Supp. Table 1). We show genome-wide maps of junctions in two formats. Colored dot plots show overall distribution of translocation numbers in selected size bins genome-wide and are useful for visualizing hotspots.

Genome-wide map of translocations originating from the c-myc25x I-SceI cassette (chr15) in αCD40/IL4-activated and I-SceI-infected B cells was created. Single translocation junctions were represented by dots located at the corresponding chromosomal position. The dot scale was 2 Mb. Clusters of translocations were indicated with color codes. Translocations were sorted by orientation, with (−) and (+)-oriented junctions plotted on the left and right side of each ideogram, respectively. Hotspot genes were listed on top of chromosomes, with notation on the left side of chromosomes to indicate position. Data are from HTGTS libraries from 7 different mice. Centromere (Cen) and telomere (Tel) positions were indicated.

Bar plots compress hotspots and illustrate translocation site density. HTGTS yields an average of 1 unique junction/5 ng of DNA, corresponding to about 1 junction/1,000 genomes. While the largest portion of data was obtained with c-myc25xI-SceI alleles cut via retroviral I-SceI, most major findings were reproduced via HTGTS libraries from the c-myc25xI-SceI allele cleaved via I-SceI-GR and the c-myc1XI-SceI allele cleaved by retroviral I-SceI. Likewise, major findings for c-myc25xI-SceI or ΔSγ12xI-SceI were reproduced with both HTGTS methods.

Analysis of Genome-wide Translocations from c-myc DSBS

For HTGTS of c-myc25xI-SceI or c-myc1xI-SceI alleles, we used primers about 200 bp centromeric on chr15 to the cassette (FIG. 1C). These primers detect junctions involving broken ends (BEs) on the centromeric (5') side of c-myc I-SceI DSBs ("5'c-myc-I-SceI BEs"). Based on convention, prey sequences joined to 5'c-myc-I-SceI BEs are in (+)

orientation if read from the junction in centromere to telomere orientation and in (−) orientation if read in the opposite direction (FIG. S3A-D). Joins in which 5'c-myc-I-SceI BEs are fused to resected 3'c-myc-I-SceI BEs would be (+) orientation (FIG. 3A). Intra-chromosomal joins to DSBs centromeric or telomeric to 5'c-myc-I-SceI BEs would be (+) or (−) junctions depending on the side of the second break to which they were joined, with potential outcomes including deletions, inversions, and extra-chromosomal circles (FIGS. S3B and S3C). Junctions to DSBs on different chromosomes could yield (+) or (−) orientations and derivative chromosomes could be centric or dicentric (FIG. S3D). We analyzed over 100,000 independent junctions from 5'c-myc-I-SceI BEs generated in WT and AID−/− backgrounds and found prey sequences to be distributed widely through the genome, with similar general distribution patterns for both backgrounds. Other than 200 kb downstream of bait break (see below), intra-chromosomal and inter-chromosomal junctions were evenly distributed into (+) and (−) orientation. This finding demonstrates that extra-chromosomal circles and acentric fragments were represented similarly to other translocation classes, indicating little impact of cellular selection on junction distribution. Analysis of thousands of 5'c-myc-I-SceI BE junctions from c-myc25xI-SceI, c-myc1xI-SceI and c-myc25xI-SceI/ROSAI-SceI-GR models revealed all to arise from end-joining, with most (75-90%) having short junctional MHs (Table 1). Finally, translocations from 5'c-myc-I-SceI BEs were located preferentially, but not exclusively, in genes (Supp. Table 3).

WT and AID−/− HTGTS maps for 5'c-myc-I-SceI BEs had other common features. First, the majority of junctions (75%) arose from joining 5'c-myc-I-SceI BEs to sequences within 10 kb of the breaksite, with most lying 3' of the breaksite. In addition, the density of joins remained relatively high within a region 200 kb telomeric to the breaksite. Notably, most junctions within this 200 kb telomeric breaksite region, but not beyond, were in the (+) orientation consistent with involvement of resected 3'c-myc-I-SceI BEs. A substantial fraction of junctions (15%) occurred within the region 100 kb centromeric to the breaksite. As these could not have resulted from resection (due to primer removal), they may reflect propensity for joining intra-chromosomal DSBs separated at such distances (Zarrin et al., 2007). Compared overall with other chromosomes, chr15 had a markedly high density of translocations along it's 50 Mb telomeric portion and relatively high density along it's centromeric portion. In addition, many chromosomes regions had relatively high or low translocation densities with such overall patterns being conserved between WT and AID−/− backgrounds. Finally, although the majority of hotspots were WT-specific, a number were shared between the WT and AID−/− backgrounds.

Analysis of HTGTS Libraries from IgH DSBs

For HTGTS of the ΔSγ12xI-SceI alleles, we used primers from the 3' end of Iγ1, on 5' (telomeric) side of the I-SceI cassette (FIG. 1C)., allowing detection of junctions involving BEs on the telomeric (5') side of Sγ1 I-SceI DSBs ("5'Sγ1-I-SceI BEs"). Intra- and inter-chromosomal joins involving 5'Sγ1-I-SceI BEs also result in (+) or (−) junctions depending on the side of the second break to which they are joined with the range of potential chromosomal outcomes including deletions, inversions, extra-chromosomal circles and acentrics. We isolated and analyzed approximately 9,000 and 8,000 5'Sγ1-I-SceI BEs junctions from WT and AID−/− libraries, respectively. Reminiscent of the 5'c-myc-I-SceI junctions, about 75% of these junctions were within 10 kb of the breaksite, with a larger proportion on the 3' (centromeric) side and predominantly in the (−) orientation, consistent with joining to resected 3'-I-SceI BEs. Outside the breaksite region, the general 5'Sγ1-I-SceI BE translocation patterns resembled those observed for 5'c-myc-I-SceI BEs, with both (+) and (−) orientation translocations occurring over all chromosomes. While we analyzed more limited numbers of 5'Sγ1-I-SceI BE junctions (Table in FIG. 4), the broader telomeric region of chr12 had a large number of hits and, within this region, there were IgH hotspots in WT but not AID−/− libraries.

Sμ and Sε are major targets of AID-initiated DSBs in B cells activated with αCD40/IL4. Correspondingly, substantial number of 5'Sγ1-I-SceI BE junctions from WT, but not AID−/−, B cells joined to either Sμ (about 500 inversion or extra-chromosomal circle junctions) or to Sε (about 280 deletion or inversion junctions), which, respectively lie approximately 100 kb upstream and downstream of the ΔSγ12x I-SceI cassette. These findings support the notion that DSBs separated by 100-200 kb distances can be joined at relatively high frequency by general repair mechanisms (Zarrin et al., 2007). We also observed frequent junctions (about 130) from WT libraries specifically within Sγ3, which lies about 20 kb upstream of the breaksite, a finding of interest as joining Sγ3 to donor Sμ DSBs during CSR in αCD40/IL4 activated B cells occurs only at low levels. Our current approach generally did not distinguish relative distribution of most junctions between chromosomal homologs. However, in WT, but not in AID−/− libraries, we found numerous (43) junctions with Sγ1, which also is targeted by AID in αCD40/IL4-activated B cells. As Sγ1 is present only on one chr12 homolog due to the ΔSγ12xI-SceI replacement mutation, these findings demonstrate robust translocation of 5'Sγ1-ISceI BEs to AID-dependent Sγ1 DSBs on the homologous chromosome, consistent with trans-switching during CSR (Reynaud et al., 2005). Finally, while AID deficiency greatly reduced junctions into S regions, we still observed a focal cluster of five 5'Sγ1-I-SceI BE junctions in or near Sμin AID−/− ΔSγ12xI-SceI libraries.

Most c-myc Translocation Hotspots are Targeted by AID

Figure 2A:
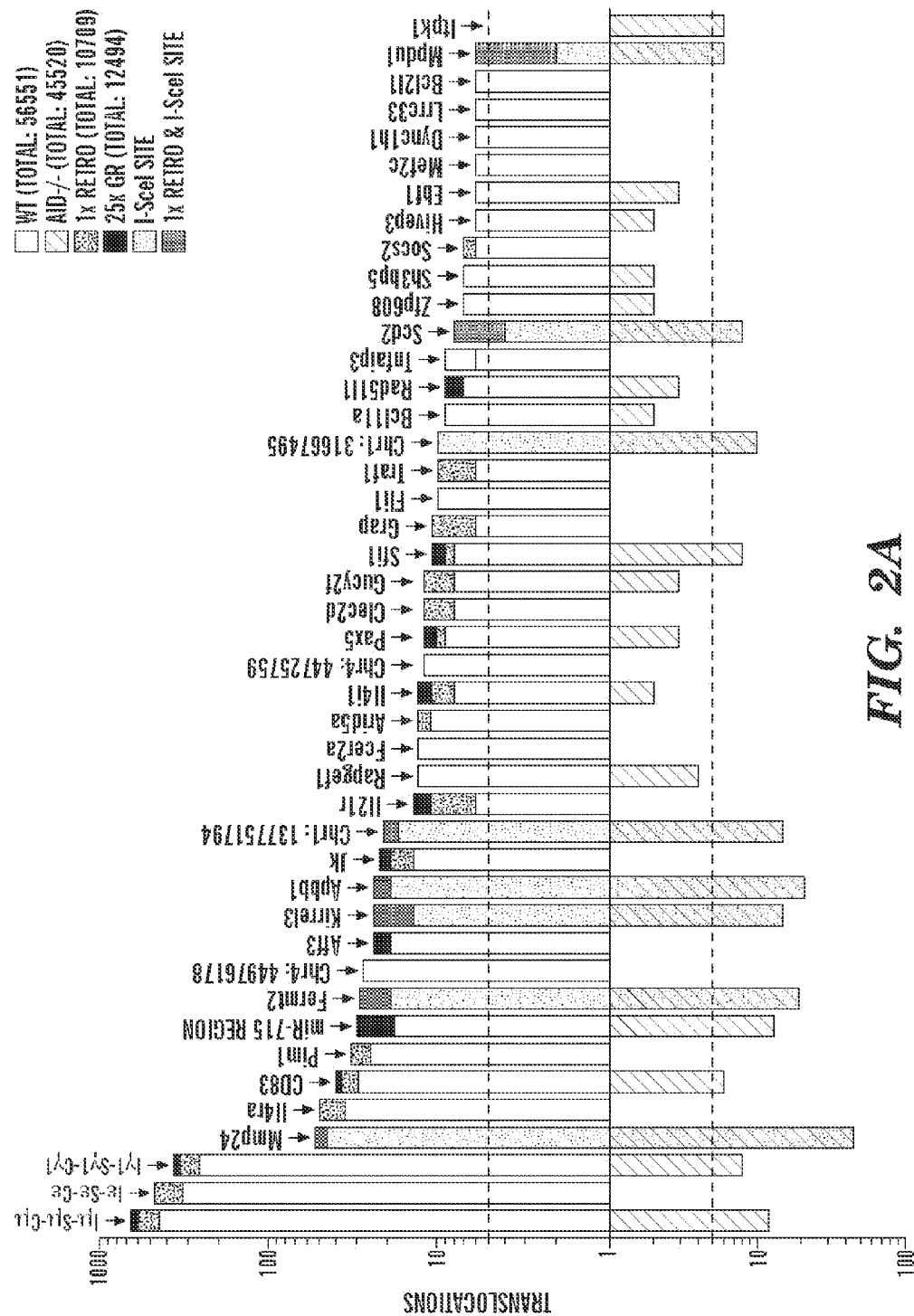
FIGS. 2A-2C show identification of specific and general translocation hot spots.

To identify 5'c-myc-I-SceI BE translocation hotspots in an unbiased manner, we separated the genome into 250 kb bins and determined the number of junctions per bin. From the Poisson's distribution of translocation frequency, we extracted bins which contained a statistically significant enrichment of translocations above random chance. Translocations clustered to a particular gene or intergenic region were considered hotspots if junction frequency was ≥5/250 kb bin (FIG. 2A). This approach identified 55 hotspots in WT libraries and 15 in AID−/− libraries (Table S2). Among the 43 most significant hotspots (>5 hits/gene, see FIG. 2), 39 were in genes (including a micro-RNA gene) and 4 were in intergenic regions. Of these hotspots, 21 were present at significantly greater levels in WT versus AID−/− backgrounds (Table S2), and, therefore, classified as AID-dependent; while 9 more were enriched (from 3 to 6 fold) in the WT background and are potentially AID-dependent. Of the others, 8 were equally represented between WT and AID−/− backgrounds, with one (Sfi1) being questionable, since the gene may exist in multiple copies (Quinlan et al., 2010). Finally there were 5 genes classified as hotspots in only one or the other background, but that were not significantly different between WT and AID−/− backgrounds (Table S2).

The Sμ, Sγ1 and Sε regions, which are the ones targeted for CSR by αCD40/IL4 treatment, were by far the strongest AID hotspots with approximately 450, 260, and 330 independent junctions, respectively, in WT c-myc25x I-SceI HTGTS libraries. Other non-IgH AID-dependent hotspots ranged from 1% to 10% of Sμ levels (FIG. 2A). The translocation specificity to these three specific S regions, which together comprise less than 20 kb, was remarkable. Indeed, there were only a few junctions in the remainder of the CH locus, which includes 4 other S regions (Sγ3, Sγ2a, Sγ2b and Sα) that are not substantially activated by αCD40/IL4. There was only one Sγ3 junction, even though this region was a marked hotspot for 5'Sγ1-I-SceI BEs. In this regard, while AID-dependent DSBs in Sγ3 likely are much less frequent than in Sμ, Sγ1 and Sε under αCD40/IL4 stimulation conditions, Sγ3 DSBs may be more favored targets of 5'Sγ1-I-SceI BEs because of linear proximity (within 20 kb). Strikingly, the relative frequency of 5'c-myc-I-SceI BEs on chr15 to the Sμ and Sε regions on chr12 were only 5 and 7 fold less, respectively, than levels of 5'Sγ1-ISceI BEs to Sμ and Sε. Thus, even though DSBs are rare in c-myc, their translocation to IgH when they do occur is driven at a high rate by other mechanistic aspects (Wang et al., 2009). Finally, translocations also occurred in Sμ and Sγ1 in AID−/− B cells at much lower levels that in WT, but frequently enough to qualify as AID-independent hot-spots.

Several top AID mutational or binding targets in activated B cells (Liu, et al 2008; Yamane, et al. 2011) were translocation hotspots for 5'-myc-I-SceI BEs, including our top 3 non-IgH hotspots (Il4ra, CD83, and Pim1) and other probable AID-dependent translocation targets (e.g. Pax5 and Rapgef1) (FIG. 2A; Table S2). We also identified other AID-dependent translocation hotspots including the Aff3, Il21r, and Socs2 genes, and a potential long intergenic non-coding RNA on chr4 (FIG. 2A; Table S2). These hotspot patterns were consistent across biological replicates and independent of the c-myc25x I-SceI versus c-myc1xI-SceI targets or how we introduced I-SceI activity (TA-induced I-SceI-GR versus retrovirally expressed I-SceI) (see FIG. 2A). Moreover, we confirmed ability of a subset of these hotspots to translocate to the c-myc25x I-SceI cassette by direct PCR (Table S4). Thus, AID not only binds and mutates a broad set of non-Ig targets but also acts on them at levels sufficient to cause DSBs and translocations. No AID-dependent hotspots were in non-transcribed intergenic regions.

Translocations Genome-wide Frequently Occur Near Active Transcription Start Sites The majority of 5'c-myc-I-SceI BE translocation hotspots were AID targets. Given the established role of transcription in AID targeting, we more broadly assessed potential roles of transcription in translocation targeting, both for individual hotspots and genome-wide. To directly quantify transcription across the genome, we applied unbiased global run-on sequencing (GRO-seq; Core et al., 2008) to two biological replicates of αCD40/IL4-activated and I-SceI-infected B cells. GRO-seq measures elongating PolI activity at approximately 100 bp resolution and distinguishes transcription on both DNA strands. For each of 10,246 and 6386 genome-wide translocation junctions from WT and AID−/− backgrounds, respectively, we determined nearest transcription start sites (TSSs).

We excluded junctions within 1 Mb of the c-myc breaksite and junctions within IgH (analyzed in depth below) to avoid biases introduced by these dominant classes of junctions. We then divided translocations based on whether the nearest TSS had significant promoter proximal activity (6858 for WT and 4937 for AID−/− background) versus no significant promoter proximal activity (3388 for WT and 2449 for AID−/− backgrounds) based on GRO-seq analysis.

Figures 2B, 2C:
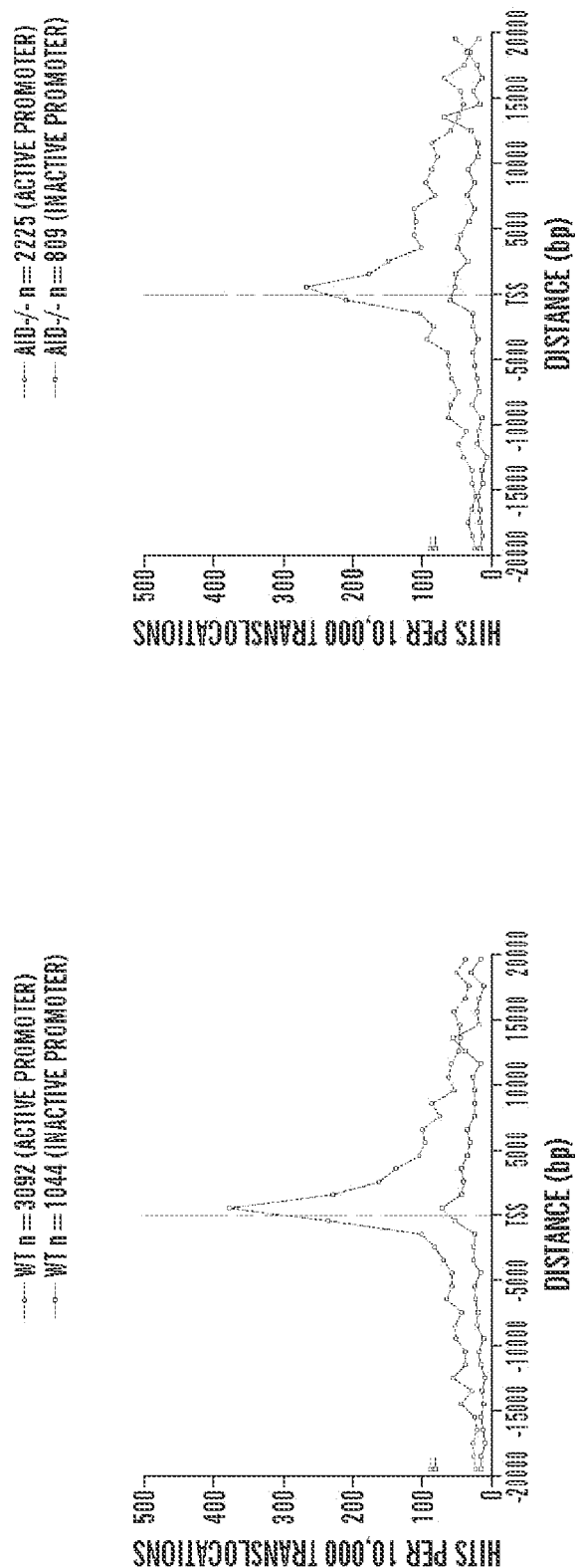

Strikingly, both WT and AID−/− translocation junctions had a high probability of being within 2-3 kb of a TSS, with the majority located in the sense transcriptional direction. Junctions also occurred at increased levels close to the TSS on the anti-sense side, correlating with focal anti-sense transcription in the immediate vicinity of activated B cell promoters genome-wide (e.g. FIG. 5) and consistent with findings in other cell types (Core et al., 2008). In contrast, there was no marked TSS correlation for genes that lacked promoter activity (FIGS. 2B and 2C). These findings strongly imply an intimate relationship between active transcription and translocation targeting genome-wide.

In B cells, constitutive transcription through Sμ initiates from upstream promoters associated with V(D)J rearrangements and "germline" promoters associated with the Iμ exon upstream of Sμ. Activation with αCD40/IL4 stimulates CSR predominantly between Sθ and Sγ1 or Sε by inducing AID and by activating transcription from promoters associated with the Iγ1 and Iε exons upstream of Sγ1 and Sε. Most IgH translocations in WT αCD40/IL4-activated B cell were in the 5' portion of Sμ, Sγ1 and Sε, consistent with transcription targeting high-level AID activity and associated DSBs to S regions through mechanisms such as R-loops and transcriptional pausing that are promoted by S region sequences. In this regard, GRO-seq analyses show transcriptional pausing within Sμ and Sγ1 and less so in Sε. In contrast to many other transcribed AID target genes (see below), germline CH genes did not have a translocation peak closely associated with their TSSs (1-2 kb upstream of the S region), even though these TSSs generated substantial sense and anti-sense transcription. AID-independent IgH locus translocations were scattered through S and C regions, consistent with DSBs initiating them arising by a different, AID-independent mechanism.

Other top AID-dependent translocation hotspots, including Il4ra, CD83, Aff3 and Pim1, as well as potential hotspots including Pax5 and Bcl11a, showed translocations clustered tightly (within a few hundred bp) in the sense direction downstream of GRO-Seq-defined bi-directional TSSs. The lower level translocations into some of these genes in AID−/− mice had less of a correlation with TSS. Notably, there were distinct peaks of translocations at the TSSs of the Il4ra gene and Il21r gene, which lies just 20 kb downstream. This is a notable finding given that there were no translocations into the 3' portion of Il4ra even though it was highly transcribed. Thus, AID appears to target translocations specifically to the transcription initiation region in transcribed genes other than IgH. Another example of interest involves CD83, where two peaks of translocations within the gene map to two potential TSSs as highlighted by the peak of sense and anti-sense transcription downstream of the annotated TSS. We found many other consistent examples, for both AID-dependent (e.g. transcribed intergenic region on chr4) and AID-independent hotspots (e.g. miR-715 gene) (FIGS. S7C and D).

Chromosome structure or chromosomal territories, possibly associated with transcription, position or other factors, might promote translocations. However, this notion has not been tested directly at a genome-wide level. For 5'c-myc-I-SceI BEs (outside of breaksite region), 55% of overall translocations were located within genes, whereas genes account for only 36% of the genome (see Table S3). Therefore, we asked whether translocations from 5'c-myc-I-SceI BEs were equally distributed along all regions of chromosomes or varied with gene density. For this purpose, we compared translocation densities to publically available gene density maps and to our GRO-seq transcription activity maps of all genes on each mouse chromosome. Strikingly, the distribution of translocations highly correlated with gene density and transcription levels. In general, chromosomal regions with the highest transcriptional activity had the highest translocation density. In contrast, regions in which transcription was very low or undetectable, including some sizable regions, generally were very low in translocations. Finally, we found no substantial chromosome regions with high overall transcription and low translocation levels.

HTGTS Libraries Reveal Numerous Cryptic Genomic I-SceI Target Sites

Ten AID-independent translocation hotspots for the 5'c-myc-I-SceI BEs were in genes, including miR-715 and 3 were in intergenic regions. Within eight of these hotspots, junctions were very tightly clustered. We examined genomic regions around these junctions and found I-SceI-related sites in the vicinity of all. These putative cryptic I-SceI sites had from 1 to 5 divergent nucleotides with respect to the canonical 18 bp I-SceI target site (FIG. 3A). Many of these putative I-SceI were very near to (within 50 bp) or actually contributed to translocation junctions. We scanned the mouse genome for cryptic I-SceI sites that diverged up to 3 positions and further identified 10 putative cryptic I-SceI sites within 400 bp of one or more 5'c-myc-I-SceI BE translocation junctions (FIG. 3A). In vitro I-SceI digestion of PCR-amplified genomic fragments demonstrated that all 8 putative I-SceI targets at hotspots, and six out of seven tested additional putative I-SceI targets, were bona fide I-SceI substrates with some as good a substrate as the canonical I-SceI site (e.g. FIGS. 3A, 3B). We performed direct translocation PCR assays with three selected cryptic I-SceI sites and confirmed their I-SceI-dependent translocation to the c-myc25x I-SceI cassette (FIG. 3C). Finally, GRO-seq analyses showed that 6 of 8 cryptic I-SceI translocation hotspots were in transcriptionally silent areas and that the two hotspots in transcribed genes were distant from the TSS (e.g. FIG. 3D), highlighting the distinction between the I-SceI-mediated hotspots and most other genomic hotspots.

With the HTGTS approach, we have identified the universe of genome-wide translocations that emanate from DSBs introduced into c-myc or IgH in activated B lymphocytes. A substantial percentage of these introduced DSBs (80-90%) join to sequences on the same chromosome proximal to the join, likely reflecting the strong preference for C-NHEJ to join DSBs intra-chromosomally (Ferguson et al., 2000; Zarrin et al., 2007; Mahowald et al., 2009). The remaining 10-15% translocate broadly across all chromosomes, with general translocation density correlating with transcribed gene density. Translocations are most often near TSSs at the level of individual genes. Despite c-myc and IgH DSBs translocating broadly, there are clear hotspots, with the majority being generated by cellular AID activity and most of the rest by activity of ectopically-expressed I-SceI at cryptic genomic targets. Thus far, we found no correlation between translocation hotspots and common fragile sites shared in mouse and human (Durkin and Glover, 2007), although more focused experimental studies will be necessary to fully address such a possible relationship. Notably, the targeted DSB ends join at similar levels to both (+) and (−) orientations of hotspot sequences, arguing against a role for cellular selection in their appearance. This finding also indicates that both sides of hotspot DSBs have similar opportunity to translocate to a DSB on another chromosome.

The majority of HTGTS junctions from the c-myc I-SceI DSBs are mediated by MH-mediated end-joining, reminiscent of joins in cancer genomes (Stratton et al., 2009) and consistent with a role for A-EJ. Recurrency of translocations in cancer genomes is a characteristic used to consider them as potential "drivers". Our HTGTS studies clearly illustrate that recurrent translocations form in the absence of selection, consistent with the notion that mechanistic factors contribute to some recurrent tumor translocations by promoting their frequent occurrence (Wang et al., 2009; Lin et al., 2009). HTGTS could be applied to further address questions regarding the contribution of mechanistic aspects versus oncogenic selection with respect to recurrent translocations in various cancers, including potential roles in this context of cancer therapeutics that affect genome stability. HTGTS also provides a method to discover recurrent genomic DSBs, as evidenced by ability of HTGTS to find known DSBs, such as AID-initiated DSBs in S regions, and previously unrecognized genomic I-SceI hotspots.

Thus, HTGTS is readily applicable for genome-wide screens for translocations and recurrent DSBs in a wide range of cell types.

AID has a Dominant Role in Targeting Recurrent Translocations Genome-wide

Prior studies demonstrated that AID binds to (Yamane et al., 2011) and mutates (Pasqualucci et al, 2001; Liu et al., 2008) non-Ig genes. Our studies now indicate that AID also induces DSBs and translocations in non-Ig genes. DSB-inducing activity is targeted to IgH S regions by transcription, which promotes AID recruitment and generates appropriate DNA substrates, such as R-loops, for this single-strand DNA-specific cytidine deaminase (Pavri and Nussenzweig, 2011; Chaudhuri et al., 2007). S regions are, by far, the predominant hotspots for translocations of 5' c-myc-I-SceI BEs in WT cells. In this regard, the major peak of 5'c-myc-I-SceI BE translocations into Sµ, Sγ1 and Sε occurs several kb downstream of the I region promoters. Likewise, the majority of Sγ1-I-SceI breaks join to Sµ, Sγ3 and Sε at similar distance downstream of the I region promoters (not shown). In contrast, the peak of translocations within AID hotspots other than S regions falls, on average, within 500 bp of the TSSs.

Thus, aspects of the transcriptional initiation process may serve to attract AID activity, as suggested by the finding that ectopically expressed AID in yeast mutates transcriptional promoter regions in the context of short R-loops (Gomez-Gonzalez and Aguilera, 2007). In this regard, the difference in translocation patterns and levels between S region transcription units and general AID hotspot genes likely reflects further evolution of S regions as specialized sequences to attract and focus high-level AID activity. As AID-dependent translocation hotspots identified by HTGTS included a number of genes mutated and/or translocated in human lymphomas, HTGTS might implicate new oncogenic targets when applied to relevant human cancer progenitor cells. Finally, S regions still qualified as translocation hotspots for 5' c-myc-I-SceI BEs in AID−/− B cells, albeit at much lower levels than in WT cells, supporting prior suggestions that these regions may be intrinsically prone to DSB and oncogenic translocations (Dudley et al., 2002; Kovalchuk et al., 2007; Unniraman et al., 2004).

A Broad Role for Transcription and Transcription Initiation in Targeting Translocations We find a remarkable genome-wide correlation between transcription and translocations, with a peak of translocation junctions lying in the vicinity of TSSs. In this regard, we observed a number of regions genome-wide that are quite low in or devoid of both translocations and transcription, but few, if any, that were low in translocations but high in transcription. On the other hand, we found that transcription is not required for high frequency translocations, since many I-SceI-dependent hotspots are in non-transcribed regions.

Together, these observations are quite consistent with transcription mechanistically promoting translocations by promoting DSBs. In this regard, transcription has long been discussed as a process that could induce DSBs through various mechanisms (Aguilera, 2002; Haffner et al., 2011).

Potential Influences Genome Organization in the Three-dimensions on Translocations Sequences lying in regions across all chromosomes translocate to DSBs in c-myc on chr15 and IgH in chr12, suggesting that the 3D position of a given DSB-containing sequences throughout the genome is not absolutely fixed relative to those of other sequences. Movement might occur during the cell cycle or perhaps be mediated in some contexts, such as shortened telomeres, via DSB response factors (Dimitrova et al., 2008). A key test of this notion will be to test whether or not new sets or subsets of HTGTS-determined translocation hotspots or regions are observed in the context of different I-SceI target sites on different chromosomes. In the latter context, the high level of translocations of 5'c-myc-I-SceI BEs along much the length of chr15, while highly correlated with transcription, might also be further promoted by high relative proximity of many intra-chromosomal regions (Lieberman-Aiden et al., 2009). More firm discrimination between long-debated breakage- and contact-first translocation models should be provided by HTGTS analyses of substrates integrated at multiple chromosomal sites, coupled with random DSB introduction genome-wide (e.g. by γ-irradiation; Mahowald et al., 2009) and parallel determination of 3D genome positioning (Lieberman-Aiden et al., 2009).

HTGTS Reveals Unexpectedly Large Number of Genomic I-SceI Targets

Our HTGTS studies of I-SceI-initiated DSBs in c-myc and IgH revealed eighteen cryptic genomic I-SceI sites as translocation hotspots. We found no strict correlation between conservation with the canonical I-SceI target site and in vitro cleavage efficiency, in agreement with a more limited prior analysis of human cryptic I-SceI cutting sites (Petek et al., 2010). There could potentially be more cryptic I-SceI sites; to find the full spectrum, bait sequences may need to be introduced into a variety of chromosomal locations to neutralize position effects. In this regard, a potentially useful feature of the endogenous I-SceI sites is that they could be used as baits for different genomic sites within the same B cell sample.

Beyond I-SceI, the HTGTS approach can readily be extended through the use of Zinc finger nucleases (Handel and Cathomen, 2011), meganucleases (Arnould et al, 2011), or sequence-specific TALENS (Christian et al., 2010) designed to cleave specific endogenous sites, thereby, obviating the requirement to introduce a cutting site and greatly facilitating the process.

The above three classes of endonucleases are being widely developed for targeting gene corrections in stem cells in the context of gene therapy for various human mutations. One major concern with all such nucleases is relative activity on the specific target versus off-target activity, with the latter having been difficult to assess. Our findings suggest that HTGTS will provide a very effective means both for identifying off-target DSBs generated by such enzymes, as well as for assessing ability of such off-target DSBs to translocate and for identifying to which sequences they translocate. Knowledge of cryptic genomic sites for endonucleases designed for therapeutic purposes should allow refinement of such enzymes to further enhance their target specificity in the genome.

Mouse Strains Utilized

ΔSγ12xI-SceI, c-myc25xI-SceI and AID−/− mice were previously described (Zarrin et al., 2007; Wang et al., 2009; Muramatsu et al., 2000). c-myc1xI-SceI mice were generated similarly to c-myc25xI-SceI. We generated ROSAI-SceI-GR mice by targeting an I-SceI-GR/IRES-tdTomato expression cassette into the Rosa26 locus. All mice used in the study are heterozygous for the modified alleles containing I-SceI cassettes. The Institutional Animal Care and Use Committee of Children's Hospital (Boston, Mass.) approved all animal work.

Splenic B Cell Purification, Activation in Culture and Retroviral Infection

CD43-B cells were isolated from spleen, cultured with αCD40/IL4 and retroviral infection was performed after 24 hours as previously described (Wang et al., 2009). c-myc25xI-SceI/ROSAI-SceI-GR B cells were cultured in medium containing charcoal-stripped serum and I-SceI-GR was activated with 10 μM triamcinolone acetate (TA, Sigma). At day 4, cells were analyzed by cytofluorimetry to assess levels of CSR and retroviral infection and harvested for DNA isolation.

Generation of HTGTS Libraries

Genomic DNA was digested with HaeIII for c-myc25xI-SceI samples or MspI for ΔSγ12xI-SceI samples. For generation of adapter-PCR libraries, an asymmetric adapter was ligated to the cleaved genomic DNA in vitro. Ligation products were then incubated with restriction enzymes chosen to reduce background arising from germline and unrearranged targeted alleles. Three rounds of nested-PCR were performed using adapter- and locus-specific primers. For generation of circularization-PCR libraries, HaeIII- or MspI-digested genomic DNA was incubated at the concentration of 1.6 ng/μl to favor intramolecular ligation and samples were treated with blocking enzymes as above. Two rounds of nested-PCR amplification were performed with primers specific for sequences upstream of the I-SceI cassette in c-myc or IgH. The generated libraries were sequenced by Roche-454. For further details, see Suppl. Experimental Procedures.

Data Analysis

Raw sequence data was aligned to the mouse reference genome (Mouse July 2007-NCBI37/mm9) with the BLAT program and filtered with custom software. For translocation hotspots analysis, filtered reads from WT or AID−/− libraries were pooled and reads aligning to chr15 or to the IgH locus were eliminated. The adjusted genome was divided into 250 kb bins and bins containing ≥5 hits constituted a hotspot.

In vitro testing of putative cryptic I-SceI sites. A genomic region encompassing each candidate I-SceI site was PCR-amplified and 500 ng of purified PCR products were incubated with 5 units of I-SceI for 3 hours. Reactions were separated on agarose gel and the relative intensity of the uncut and I-SceI-digested bands was calculated with the FluorchemSP program (Alpha Innotech).

PCR Assay to Detect Translocations Between c-myc and Cryptic I-SceI Sites

Translocation junctions between c-myc and candidate cryptic I-SceI targets were PCR-amplified from DNA prepared from αCD40/IL4-activated c-myc25xI-SceI B cells infected with control or I-SceI-expressing retrovirus, according to our standard protocol (Wang et al., 2009). Primer sequences and PCR conditions are detailed below.

GRO-seq

Nuclei were isolated from day 4 αCD40/IL4-stimulated and I-SceI-infected c-myc25xI-SceI B cells as previously described (Giallourakis et al., 2010). GRO-seq libraries were prepared from 5×106 cells from two independent mice using the previously described protocol (Core et al., 2008). Both libraries were sequenced on the Hi-Seq 2000 platform with single-end reads and analyzed as previously described. After filtering and alignment were performed, we obtained 34,212,717 reads (mm9) for library 1 and 15,913,244 reads (mm9) for library 2. The results between libraries were highly correlated and therefore we show results only from replicate 1 in e.g., FIG. 3, and below.

Gene targeting of c-myc1xI-SceI and ROSAI-SceI-GR Alleles

To generate the c-myc1xI-SceI targeting construct, the previously described c-myc25xI-SceI targeting construct (Wang et al., 2009) was digested with I-SceI and re-ligated to generate a construct containing a single I-SceI site cassette, flanked by a 4.6 kb SphI-SphI 5' homology arm encompassing c-myc exon1 and a 2.6 kb SphI-SphI 3' homology arm containing c-myc exon 2 and 3. We electroporated the targeting construct into TC1 (129/Sv) ES cells and screened EcoRI-digested DNA to identify potentially targeted ES cell clones via Southern blotting with a 5' probe consisting of the 1.5 kb XbaI-XbaI fragment upstream of c-myc exon1 and a 3' probe consisting of the 1.5 kb XhoI-KpnI fragment downstream of c-myc exon3. To generate the ROSAI-SceI-GR allele we followed the previously described strategy (Sasaki et al., 2006) to target an I-SceI-GR/IRES-tdTomato expression cassette into TC1 (129/Sv) ES cells. In both cases, the Neo cassette was deleted from targeted ES clones by infection with a Cre-recombinase-expressing adenovirus before generating c-myc1xI-SceI or ROSAI-SceI-GR mice.

B Cell Culture Conditions, Retroviral Infection and CSR Assays

Retroviral supernatants were prepared from Phoenix packaging cells transfected with pMX-ISceI vector or empty pMX vector as control. B cells were put in culture at a density of 1×106/ml in RPMI medium containing fetal bovine serum, αCD40 (1 µg/ml, eBioscience) and IL4 (20 ng/ml, R&D Systems). After 24 hours of culture, retroviral infection was performed adding one volume of viral supernatant, spinning for 1.5 hours at 2400 RPM in the presence of polybrene at 2.5 µg/ml and incubating cells with viral supernatant overnight. After infection, medium was changed and cells were replated at 0.5×106/ml. At day 4 of stimulation, infection efficiency was evaluated by measuring the percentage of cells expressing the retroviral IRES-GFP and was found to be between 60% and 85%. ROSAI-SceI-GR B cells were cultured in RPMI medium as above but with 15% charcoal-stripped fetal bovine serum to minimize nonspecific activation of the I-SceI-GR fusion and thus obtain high levels of cutting at the appropriate time. CSR was evaluated in the case of retrovirally infected cells by staining with Cy5-PE-labeled anti-mouse B220 (eBiosciences) and PE-labeled anti-mouse IgG1 (BD Biosciences). The TA-induced ROSAI-SceI-GR B cells were evaluated by staining with Cy5-PE-labeled anti-mouse B220 and FITC-labeled anti-mouse IgG1 (BD Biosciences). CSR ranged between 25% and 40% for retrovirus-infected B cells and 9-12% for TA-induced B cells.

ROSAI-SceI-GR B Cell Hybridoma Analysis

Day 4 activated c-myc25x I-SceI/ROSAI-SceI-GR B cells were fused to the NS-1 fusion partner (ATCC TIB-18) and selected for 7-10 days in HAT medium. Single hybridoma clones were expanded and DNA was prepared. Integrity of the c-myc25x I-SceI cassette was assessed by performing PCR reactions with primers Myc-Prelox and Myc-Ex2a (see primers sequences in Table 1).

Two Color FISH

Metaphases were prepared from day 4-stimulated c-myc25x I-SceI and c-myc1x I-SceI B cells infected with either control or I-SceI-expressing retrovirus, following standard protocols (Wang et al., 2009). FISH was performed with the following BAC probes flanking the c-myc locus: RP24-434C10 (centromeric to c-myc) and RP23-113021 (telomeric to c-myc). The intact c-myc locus shows colocalization of signals from the two probes, whereas c-myc breaks and translocations are visualized as split probe signals.

Generation of HTGTS Libraries by Adapter-PCR

Genomic DNA from c-myc25x I-SceI, c-myc1x I-SceI and c-myc25x I-SceI/ROSAI-SceI-GR B cells was digested overnight with HaeIII and HaeIII-generated blunt ends were A-tailed with Klenow polymerase. Genomic DNA from ΔSγ12x I-SceI B cells was digested overnight with MspI. An asymmetric adapter (composed of an upper linker and a lower 3'-modified linker) was then ligated to fragmented DNA at a molar ratio of 20:1 for 30 minutes at 25° C. To remove unrearranged I-SceI cassettes, ligation reactions were digested either with I-SceI, or with both EcoRV and XbaI (for c-myc libraries). The blocking digests were carried out for 8 hours. Translocation junctions were then PCR-amplified using the emulsion (em)-PCR approach as previously described (Williams et al., 2006). In the first round of PCR, 1 µg of DNA was amplified in a final volume of 50 µl, using a biotinylated forward primer (Myc-L for c-myc libraries or Sγ1-C for ΔSγ1 libraries; see table below for primer sequences) and an adapter-specific reverse primer (AP1) and Phusion polymerase (Finnzymes). 20 PCR cycles were performed in the following conditions: 98° C. for 10 seconds, 58° C. for 30 seconds, and 72° C. for 30 seconds. Multiple reactions were performed in generating large-scale libraries. Thereafter, biotinylated PCR products were isolated using the Dynabeads MyOne Streptavidin C1 kit (Invitrogen) and an additional 3-hour digestion with blocking enzymes was performed.

PCR products were eluted from the beads via a 30 minute incubation at 65° C. in 95% formamide/10 mM EDTA and purified. The purified products were then amplified in a second round with em-PCR. 30 µl of the first round PCR product, 80 pmol each of primers AP2 and Myc-Prelox (for c-myc libraries) or Sγ1-E (for ΔSγ1 libraries), 20 µl ultrapure BSA (Ambion) and 2 µl Taq polymerase (Qiagen) in a final volume of 200 µl were emulsified in 400 µl of an oil-surfactant mixture. The emulsion mixture was divided into 50 µl individual aliquots and PCR was performed using the following conditions: 30 cycles of 94° C. for 30 seconds, 60° C. for 30 seconds, and 72° C. for 1 minute. Following PCR, the products were pooled and centrifuged in a table-top centrifuge for 5 minutes at 14,000 RPM to separate the phases and the oil layer was removed. The sample was then extracted 3 times with 1 ml of $H_2O$-saturated diethyl ether and DNA was re-purified. The third, non-emulsion, round of PCR was performed with the same primers as in round 2, but with the addition of linkers and barcodes for 454 sequencing. After amplification, the pooled PCR reactions were size-fractionated between 200 and 800 base pairs on agarose gel. An aliquot of the gel-purified material was submitted for 454-sequencing.

Generation of HTGTS Libraries by Circularization-PCR

Genomic DNA from c-myc25xI-SceI, c-myc1xI-SceI and c-myc25xI-SceI/ROSAI-SceI-GR B cells was digested overnight with HaeIII. Genomic DNA from ΔSγ12xI-SceI B cells was digested overnight with MspI. After purification 250 ng of DNA was ligated for 12-hours in 150 µl total volume to favor formation of intramolecular circles. To obtain HTGTS libraries, multiple ligations were performed for each sample and the final purified ligation products were pooled together. The ligated material was heat inactivated at 65° C. for 30 minutes and then incubated with EcoRV and XbaI (for c-myc libraries) or EcoRI, HindIII, and PstI (for ΔSγ1 libraries) for 4 hours. These blocking digests served to linearize circular products deriving from WT (non-targeted) alleles and from unrearranged I-SceI cassettes. The DNA was then purified and resuspended in a final volume of 50 μl. Nested PCR was either performed in multiple reactions, using 1 μl of purified ligation mixture each (which yielded on average at least one junction per reaction) or in bulk with the em-PCR approach detailed above. The first PCR amplification step was carried out with Myc-G and Myc-H primers for c-myc libraries, or Sγ1-B and Sγ1-C for ΔSγ1 libraries (see table for primer sequence) and Phusion polymerase (Finnzymes). 20 PCR cycles (for em-PCR) or 30 PCR cycles (for separate reactions) were performed as follows: 98° C. for 10 seconds, 58° C. for 30 seconds, and 72° C. for 30 seconds. For large-scale libraries, 60 em-PCR reactions of 50 μl final volume were run, using 500 ng of ligated DNA per each reaction. For the second PCR amplification step we used primers Myc-I and Myc-Prelox (for c-myc libraries) or primers Sγ1-A and Sγ1-E (for ΔSγ1 libraries) and Taq polymerase (Qiagen). 30 cycles of PCR amplification were performed with the following conditions: 94° C. for 30 seconds, 60° C. for 30 seconds, and 72° C. for 1 minute. For the multiple, non-emulsion PCR reactions, round 2 PCR primers contained the linker fragment and barcode as required for 454 sequencing. In the case of em-PCR, these linkers and barcodes were added in a third round of PCR (10 cycles). After amplification, PCR products were pooled and 200-1000 bp fragments were isolated after fractionation on agarose gel and submitted for 454-sequencing.

Calculation of Restriction Sites Distribution

We defined all recognition sequences for HaeIII or MspI in the mouse genome and calculated the distances between two consecutive sites. The distribution of the distance showed that the probability of getting a fragment of more than 10 kb for each of the cutting enzyme was less than 0.002% for HaeIII and 1.72%. for MspI.

Data Analysis

Alignment and filtering. Raw 454 sequence data was aligned to the mouse reference genome (Mouse July 2007-NCBI Build37/mm9) with the BLAT program (Kent, 2002). Data were then filtered to remove PCR repeats (including repeats that are slightly divergent due to sequencing errors), fragment ligation artifacts (where, for example, a random HaeIII or MspI fragment was incorporated during in vitro ligation), 'illegitimate' ligation products (rare events in which a fragment generated by the HaeIII or MspI became ligated in vitro to an in vivo generated I-SceI end), and mis-priming during PCR. Specific settings for BLAT and scripts for the filters are available on request. For hotspot analysis, candidate hits were confirmed by repeating the alignment using the NCBI BLAST webserver (default settings) (Johnson et al., 2008) and by locating and inspecting the sequence spanning the translocation junction. Hits with discrepancies between BLAST and BLAT alignment and bearing junctions that had already been scored in the same mouse/DNA sample were removed. These post-filtering steps were simply executed and were critical for hotspot designations to prevent infrequent artifacts from confounding the analyses.

Data display. To visualize the distribution of junctions within HTGTS libraries circle plots were generated using Circos program (Krzywinski et al., 2009). As input data for Circos, the coordinates of the breaksite and the translocation junctions were used. To generate translocatome maps, we also used R program (Development Core Team, 2010) to calculate the position of each individual junction relative to the chromosomal length (divided into bins of different size as specified in Figure legends) and then generated a dot to represent a single translocation junction. For comparison of translocation density maps and nascent RNA signals, we uploaded both data sets to the UCSC genomw browser.

Determination of translocation hotspots. All filtered reads derived from WT or AID-/- libraries were pooled for hotspot analysis. Reads aligning to chr15 or to the IgH locus were eliminated from each pool. The adjusted genome was divided into equal sized bins (phased with the first nucleotide of each chromosome), and bins occupied with zero, one, two, etc. hits were enumerated. The bin size was adjusted down from 2 Mb until a size for which 60% of the bins were empty. The data fit a Poisson distribution. Hotspots were defined as all bins in the 10% of the tail of the distribution ($P<0.05$). For both the WT and AID-/- pools, we used a bin size of 250 kb. Bins containing ≥5 hits constituted a hotspot. When pools were re-analyzed after offsetting bins by 190 kb hotspots were similar in number and location.

Evaluation of HTGTS Background

Human DNA isolated from the K562 cell line was mixed 1:1 with DNA from αCD40/IL4-activated and I-SceI-infected c-myc25xI-SceI or ΔSγ12xI-SceI primary B cells from WT or AID-/- background. The DNA mixes were then used to generate HTGTS libraries as described. The primary sequence readouts were analyzed against the mouse genome to identify the real translocations as detailed above. In addition, the same primary readouts were analyzed against the human genome with the same filter settings, to identify potential artifactual translocations involving human DNAs. Alignment were verified by BLAST. The background was calculated as percentage of artifactual human:mouse hybrid junctions over total junctions.

Analysis of translocation junctions. Small-scale HTGTS libraries obtained from one c-myc25xI-SceI (1359 junctions), one c-myc1xI-SceI (1066 junctions) and one c-myc25xI-SceI/ROSAI-SceI-GR mouse (547 junctions) were extensively and individually post-filtered to remove all duplicate sequences (defined as identical junctions) and ambiguous alignments. MH at the junction was calculated with two different algorithms, and sequences that differed were further inspected. Junctions mapping within 1 Mb from the breaksite (chr15: 61818880) on either side were considered separately. Junctions corresponding to local resection events (within the segment defined by the first HaeIII site telomeric to the I-SceI cassette) were not included in the analysis.

Identification of cryptic I-SceI sites. Candidate I-SceI sites were identified by examining the sequences of all recurrent hits in the WT or AID-/- library pools displaying an exceptionally focal pattern. In addition, all translocation junctions were compared against a hit table of all sites in the mouse genome (±200 bp) matching the canonical I-SceI consensus sequence at 15 or more positions. A genomic region encompassing each candidate I-SceI site then was PCR-amplified with primers detailed below. This approach was taken to avoid potential effects of dam and dcm methylation on cutting efficiency (Petek et al., 2010). The genomic sequence of the candidate I-SceI sites was confirmed by sequencing the corresponding PCR product. 500 ng of purified PCR products were digested in vitro with 5 units of I-SceI for 3 hours. Digestion reactions were separated on agarose gel and the relative intensity of the uncut and I-SceI-digested bands were calculated with the FluorchemSP program (Alpha Innotech). Efficiency of cutting was scored as follows: +++, 100% to 70%; ++, 70% to 30%; +, 30% to 10%; −, less than 10%.

PCR Assay to Detect Translocations Between c-myc25x I-SceI and Hotspot Genes

Translocation junctions were PCR-amplified from DNA prepared from αCD40/IL4-activated c-myc25xI-SceI B cells infected with control or I-SceI-expressing retrovirus.

To estimate translocation frequencies, multiple independent PCR reactions were performed each containing 5000 or 50000 cell equivalents of DNA. Two rounds of nested PCR reactions were performed. Reverse primers Myc-Ex2b and Myc-Ex2a (see table for primer sequence) were specific for c-myc sequence telomeric to the I-SceI cassette. Forward primers were specific for each gene tested (Dmrt1, Scd2, Mmp24, Il4ra, Il21r, CD83 and Pim1) and are listed in the table below. For cryptic I-SceI targets, these primers were chosen centromeric to the putative site. For the first PCR round, conditions were as follows: 94° C. 3 min; 94° C. 15 s, 62° C. 15 s, 68° C. 7 min plus an increment of 20 s per cycle, 25 cycles; 68° C. 5 min. For the nested PCR round, conditions were as follows: 94° C. 3 min; 94° C. 15 s, 62° C. 15 s, 68° C. 7 min, 25 cycles; 68° C. 5 min. The Expand Long Template PCR System (Roche) was used for both reactions.

Analysis of GRO-seq Data

We calculated promoter proximal gene activity indexes at transcriptional start sites (TSSs) by analyzing the GRO-seq density ±1 kb around the TSSs as defined for 21,906 genes annotated in the current reference sequence of the mouse genome (NCBI Build 37, mm9) and downloaded from the UCSC server at world wide web at hgdownload "dot" cse "dot" ucsc "dot" edu "forward slash" goldenPath "forward slash" mm9 "forward slash" database "forward slash" refGene "dot" txt "dot"gz). Where a gene had multiple isoforms, the longest was used. Each 2 kb window was divided into 200 bp bins and tiled across in 50 bp increments to identify the peak GRO-seq signal, which we then took as the experimental TSS. We obtained a promoter proximal gene activity and a p value based on our background density, which we calculated to be 0.02 reads/kb. If the promoter proximal peak had a p value less then 0.001, we considered the gene to have significant promoter proximal activity and assigned the coordinate of the TSS based on the GRO-seq peak derived above experimentally. If a TSS, as annotated in the mm9 assembly, did not have significant promoter proximal activity in the region then this mm9 coordinate was used.

TABLE 1

Primer Sequences

| NAME (orientation) | SEQUENCE | PURPOSE |
|---|---|---|
| c-myc primers | | |
| Myc-Prelox (For) | ACCGCCGCTAATTCCGATCATATTC (SEQ ID NO: 1) | Amplifying 25x cassette; 2nd round PCR for HTGTS (ad-PCR and cir-PCR) |
| Myc-Ex2a (Rev) | ATAGGGCTGTACGGAGTCGTAGTC (SEQ ID NO: 2) | Amplifying 25x cassette; 2nd round direct translocation PCR |
| Myc-Ex2b (Rev) | GCTCTGCTGTTGCTGGTGATAGAA (SEQ ID NO: 3) | 1st round direct translocation PCR |
| Myc-G (Rev) | CCTTCGAGCAGGGACTTAGCC (SEQ ID NO: 4) | 1st round PCR for HTGTS (cir-PCR) |
| Myc-H (For) | AGCAGCTGCTAGTCCGACGA (SEQ ID NO: 5) | 1st round PCR for HTGTS (cir-PCR) |
| Myc-I (Rev) | AGACGCCCAGGAATCGCCAT (SEQ ID NO: 6) | 2nd round PCR for HTGTS (cir-PCR) |
| Myc-L (For) | CGAGCGTCACTGATAGTAGGGAGT (SEQ ID NO: 7) | 1st round PCR for HTGTS (ad-PCR) |
| Sγ1 primers | | |
| Sγ1-B (Rev) | GCTCAGGTTTGTCTGTGGG (SEQ ID NO: 8) | 1st round PCR for HTGTS (cir-PCR) |
| Sγ1-C (For) | GGAATATATCGAGAAGCCTGAGG (SEQ ID NO: 9) | 1st round PCR for HTGTS (ad-PCR and cir-PCR) |
| Sγ1-A (Rev) | CTC TAC ATG CCT GTG CTT GT (SEQ ID NO: 10) | 2nd round PCR for HTGTS (cir-PCR) |
| Sγ1-E (For) | GCCTCGAGGGACCTAATAAC (SEQ ID NO: 11) | 2nd round PCR for HTGTS (cir-PCR and ad-PCR) |

TABLE 1-continued

Primer Sequences

| NAME (orientation) | SEQUENCE | PURPOSE |
|---|---|---|
| Other primers for ad-PCR | | |
| Upper linker | GTAATACGACTCACTATAGGGCACGCGTGGTCGACGGCCCGGGCTGGT (SEQ ID NO: 12) | |
| Lower linker | TAACCAGCCC (5'P, 3'inverted dT) (SEQ ID NO: 13) | |
| MspI lower linker | CGACCAGCCC (5'P, 3'inverted dT) (SEQ ID NO: 14) | |
| AP1 | GTAATACGACTCACTATAGGGC (SEQ ID NO: 15) | |
| AP2 | ACTATAGGGCACGCGTGGT (SEQ ID NO: 16) | |
| Primers for amplification of genomic region containing cryptic I-SceI sites | | |
| chr1A-for | CCCTGCCTCCCTTAAGCAGGC (SEQ ID NO: 17) | |
| chr1A-rev | CAGACTTGGAGGGAGGGAGGG (SEQ ID NO: 18) | |
| chr2A-for | TCAAAGATGTTTGGAGGCCACTGC (SEQ ID NO: 19) | |
| chr2A-rev | GCTCATGCAACACTACCCTGTGC (SEQ ID NO: 20) | |
| chr2B-for | TCTGAGAGTCTTCCCAGTCCACC (SEQ ID NO: 21) | |
| chr2B-rev | GGGAAGTGCACAGCAAACCGG (SEQ ID NO: 22) | |
| chr2C (Mmp24)-for | AATCCTGGTACTGGAATCGG (SEQ ID NO: 23) | |
| chr2C (Mmp24)-rev | AGATGGCACACTGCTAGGAC (SEQ ID NO: 24) | |
| chr4-for | ACTGCTCTGCCTGGTCACCTTG (SEQ ID NO: 25) | |
| chr4-rev | TGCACGTGATTCCAGCACTTGG (SEQ ID NO: 26) | |
| chr7 (Apbb)-for | TCCACACTCACTACAGCCATTTCC (SEQ ID NO: 27) | |
| chr7 (Apbb)-rev | TCTCTTGTTCCCCTCATACCTCAC (SEQ ID NO: 28) | |
| chr8 (PaIId)-for | GACACACTGCAAAAGCTGATCCCC (SEQ ID NO: 29) | |
| chr8 (PaIId)-for | TCCTGCCAGTCACCTCCCATC (SEQ ID NO: 30) | |
| chr9 (kirrel3)-for | ACAAGGCACCACACAATGGGTG (SEQ ID NO: 31) | |
| chr9 (kirrel3)-rev | TTAAGGGCACTGTCTGAGGGGG (SEQ ID NO: 32) | |

TABLE 1-continued

Primer Sequences

| NAME (orientation) | SEQUENCE | PURPOSE |
|---|---|---|
| chr13-for | AACCCTCATACTCTCCAGCCACC (SEQ ID NO: 33) | |
| chr13-rev | TTGCTGCCCTATGAGTCCTGGG (SEQ ID NO: 34) | |
| chr14 (Fermt2)-for | GAGGCTCACCTTTCAGAGGGCC (SEQ ID NO: 35) | |
| chr14 (Fermt2)-rev | GAGGCTTCCCTTATCGTGGCACC (SEQ ID NO: 36) | |
| chr15A-for | GGCATCGCATCCAAGTCAACCTC (SEQ ID NO: 37) | |
| chr15A-rev | CCTTTTGAGGGCCACCTGACTG (SEQ ID NO: 38) | |
| chr15B (Aco2)-for | TTAAGGTGGTCTTCCCCTGAGGC (SEQ ID NO: 39) | |
| chr15B (Aco2)-rev | AAGAGGCTGTCAGTGAGCCGAG (SEQ ID NO: 40) | |
| chrX-for | AGTGAGAAATGAGCACCATGGGC (SEQ ID NO: 41) | |
| chrX-rev | GAGGCACGAAGAGGCTACTCAG (SEQ ID NO: 42) | |

Primers for direct tranlsocation PCR

| NAME (orientation) | SEQUENCE | PURPOSE |
|---|---|---|
| CD83-ExtF | TGCTTACGCCGCTCTGTTTCT (SEQ ID NO: 43) | First round |
| CD83-IntF | TATGCAGTGTCCTGGCCAAG (SEQ ID NO: 44) | Second round |
| Dmrt1-ExtF | GACCTACCACTCTGCAGCTGG (SEQ ID NO: 45) | First round |
| Dmrt1-IntF | GGAGTTCTAGGCCAGCCTTGG (SEQ ID NO: 46) | Second round |
| Il21r-ExtF | ATGTCCTCCTTCCCACAATGCTG (SEQ ID NO: 47) | First round |
| Il21r-IntF | AGCAGTGCTTAAGGCAGAAAGTCTG (SEQ ID NO: 48) | Second round |
| Il4ra-ExtF | GCCTGAACTCGACGGGTAGGAAC (SEQ ID NO: 49) | First round |
| Il4ra-IntF | AGAACCGATCTGGCCTGAAACC (SEQ ID NO: 50) | Second round |
| Mmp24-ExtF | GGTCACTAACTCATGCCCCACC (SEQ ID NO: 51) | First round |
| Mmp24-IntF | GAGGAGACGGAAGTGAAGCTCTG (SEQ ID NO: 52) | Second round |
| Pim1-ExtF | TGGCCATTAAGCACGTGGAGAAG (SEQ ID NO: 53) | First round |

TABLE 1-continued

Primer Sequences

| NAME (orientation) | SEQUENCE | PURPOSE |
|---|---|---|
| Pim1-IntF | GATTGGGGAGAACTGGTGAGTGAG (SEQ ID NO: 54) | Second round |
| Scd2-ExtF | AAGGGCACAAGTTAGGTGGTAGGA (SEQ ID NO: 55) | First round |
| Scd2-IntF | AGGGTGTGAGAGGAAAATGGTGG (SEQ ID NO: 56) | Second round |

TABLE S1

Mice used for generation of HTGTS libraries.

$c\text{-}myc^{1x\ I\text{-}SceI}/WT$

| Mouse # | Mouse ID | sex | age | % CSR | % inf | Total n of translocations | | | Hits on chr15 | | Hits on all chrs (chr15 excluded) | |
|---|---|---|---|---|---|---|---|---|---|---|---|---|
| | | | | | | ad | cir | tot | n | % | n | % |
| #1 | 183 | F | 8 mo | 43 | 74 | 6042 | 3046 | 9088 | 7034 | 77.40 | 2054 | 22.60 |
| #2 | 2 | M | 3 mo | 24 | 87 | nd | 549 | 549 | 443 | 80.69 | 106 | 19.31 |
| #3 | 9 | M | 2 mo | 35 | 63.5 | nd | 4303 | 4303 | 3423 | 79.55 | 880 | 20.45 |
| TOTA | | | | | | 6042 | 7898 | 13940 | 10900 | 78.19 | 3040 | 21.81 |

$c\text{-}myc^{25x\ I\text{-}SceI}/ROSA^{I\text{-}SceI\text{-}GR}$

| Mouse # | Mouse ID | sex | age | % CSR | % inf | Total n of translocations | | | Hits on chr15 | | Hits on all chrs (chr15 excluded) | |
|---|---|---|---|---|---|---|---|---|---|---|---|---|
| | | | | | | ad | cir | tot | n | % | n | % |
| #1 | 3 | M | 1.5 mo | 12.6 | Na | nd | 1089 | 1089 | 868 | 79.71 | 221 | 20.29 |
| #2 | 8 | M | 1.5 mo | 10.8 | Na | nd | 1100 | 1100 | 891 | 81.00 | 209 | 19.00 |
| #3 | 16 | M | 2 mo | 9.2 | Na | nd | 735 | 735 | 557 | 75.78 | 178 | 24.22 |
| #4 | 17 | M | 3.5 | 46 | Na | nd | 393 | 393 | 302 | 76.84 | 91 | 23.16 |
| #5 | 433, 43 | F | 4.5 mo | 9 | Na | 9137 | nd | 9137 | 7810 | 85.48 | 1327 | 14.52 |
| TOTA | | | | | | 9137 | 3317 | 12454 | 10428 | 83.73 | 2026 | 16.27 |

$c\text{-}myc^{25x\ I\text{-}SceI}/WT$

| Mouse # | Mouse ID | sex | age | % CSR | % inf | Total n of translocations | | | Hits on chr15 | | Hits on all chrs (chr15 excluded) | |
|---|---|---|---|---|---|---|---|---|---|---|---|---|
| | | | | | | ad | cir | tot | n | % | n | % |
| #1 | 488 | M | 3 mo | 32 | 60 | 12479 | 1778 | 14257 | 11497 | 80.64 | 2760 | 19.36 |
| #2 | 484, 48 | M, | 3 mo | 31 | 61 | 14426 | nd | 14426 | 12007 | 83.23 | 2419 | 16.77 |
| #3 | 311 | F | 6.5 mo | 17 | 63 | 14365 | 1065 | 15430 | 13539 | 87.74 | 1891 | 12.26 |
| #4 | 248, 24 | F | 2 mo | 33 | 70 | nd | 3942 | 3942 | 2991 | 75.88 | 951 | 24.12 |
| #5 | 253 | M | 5 mo | 41 | 45 | 1200 | 1778 | 2978 | 2354 | 79.05 | 624 | 20.95 |
| #6 | 749 | M | 4 mo | 22 | 86 | nd | 3708 | 3708 | 3014 | 81.28 | 694 | 18.72 |
| #7 | 858 | F | 1.5 mo | 37 | 67 | nd | 1511 | 1511 | 1258 | 83.26 | 253 | 16.74 |
| TOTA | | | | | | 42470 | 13782 | 56252 | 46660 | 82.95 | 9592 | 17.05 |

$c\text{-}myc^{25x\ I\text{-}SceI}/AID\text{-}/\text{-}$

| Mouse # | Mouse ID | sex | age | % CSR | % inf | Total n of translocations | | | Hits on chr15 | | Hits on all chrs (chr15 excluded) | |
|---|---|---|---|---|---|---|---|---|---|---|---|---|
| | | | | | | ad | cir | tot | n | % | n | % |
| #1 | 409 | M | 4 mo | 1.25 | 74 | 13980 | 3177 | 17157 | 15000 | 87.43 | 2157 | 12.57 |
| #2 | 487 | F | 3 mo | 1.04 | 68 | 13149 | 2233 | 15382 | 13322 | 86.61 | 2060 | 13.39 |

TABLE S1-continued

Mice used for generation of HTGTS libraries.

| #3 | 494 | F | 3 mo | 1.15 | 62 | 9911 | nd | 9911 | 8582 | 86.59 | 1329 | 13.41 |
| #4 | 342 | M | 3 mo | 0.5 | 37 | 1245 | 2225 | 3470 | 2911 | 83.89 | 559 | 16.11 |
| TOTA | | | | | | 38285 | 7635 | 45920 | 39815 | 86.71 | 6105 | 13.29 |

| ΔSγ1$^{25x\ I\text{-}SceI}$/WT | | | | | | | | | | | Hits on all chrs | |
|---|---|---|---|---|---|---|---|---|---|---|---|---|
| Mouse | Mouse | | | | | Total n of translocations | | | Hits on chr15 | | (chr15 excluded) | |
| # | ID | sex | age | % CSR | % inf | ad | cir | tot | n | % | n | % |
| #1 | 186 | F | 1.5 mo | 20 | 48 | nd | 1675 | 1675 | 1568 | 93.61 | 107 | 6.39 |
| #2 | 188 | F | 8 mo | 13 | 74 | 5190 | 972 | 6162 | 5673 | 92.06 | 489 | 7.94 |
| #3 | 958 | F | 2.5 mo | 27 | 84 | nd | 1542 | 1542 | 1425 | 92.41 | 117 | 7.59 |
| TOTA | | | | | | 5190 | 4189 | 9379 | 8666 | 92.40 | 713 | 7.60 |

| ΔSγ1$^{25x\ I\text{-}SceI}$/AID-/- | | | | | | | | | | | Hits on all chrs | |
|---|---|---|---|---|---|---|---|---|---|---|---|---|
| Mouse | Mouse | | | | | Total n of translocations | | | Hits on chr15 | | (chr 15 excluded) | |
| # | ID | sex | age | % CSR | % inf | ad | cir | tot | n | % | n | % |
| #1 | 165 | M | 2 mo | 0.1 | 40 | nd | 2742 | 2742 | 2561 | 93.40 | 181 | 6.60 |
| #2 | 278 | F | 7 mo | 0.3 | 77 | 3081 | 1350 | 4431 | 4115 | 92.87 | 316 | 7.13 |
| TOTA | | | | | | 3081 | 4092 | 7173 | 6676 | 93.07 | 497 | 6.93 |

TABLE S2

Number of hits within hotspots and in c-myc$^{25xI\text{-}SceI}$ WT and AID-/- HTGTS libraries

| Gene/ intergenic region | n of hits in hotspots[a] | | Binomial test (p-value) | n of total hits[b] | | Chr | Genomic sequence (mm9, UCSC browser) | Size (bp) |
|---|---|---|---|---|---|---|---|---|
| | WT | AID-/- | | WT | AID-/- | | | |
| | | | ally signific | | | | | |
| Iμ-Sμ-Cμ | 446 | 12 | 2.20E-16 (p < 0.001) | 446 | 12 | chr12 | 114,656,789-114,665,418 | 8,629 |
| Iε-Sε-Cε | 327 | 0 | 2.20E-16 (p < 0.001) | 327 | 0 | chr12 | 114,506,320-114,515,995 | 9,675 |
| Iγ1-Sγ1-Cγ1 | 259 | 8 | 2.20E-16 (p < 0.001) | 259 | 8 | chr12 | 114,563,470-114,577,590 | 14,120 |
| Il4ra | 35 | 1 | 6.33E-09 (p < 0.001) | 35 | 1 | chr7 | 132,695,796-132,722,988 | 27,193 |
| chr4:44976178 | 26 | 1 | 1.32E-05 (p < 0.001) | 26 | 1 | chr4 | 44,976,178-44,983,040 | 6,862 |
| Pim1 | 25 | 1 | 2.39E-05 (p < 0.001) | 25 | 1 | chr17 | 29,627,990-29,632,404 | 4,415 |
| Aff3 | 19 | 1 | 5.65E-05 (p < 0.001) | 19 | 1 | chr1 | 38,234,172-38,721,800 | 487,629 |
| J Kappa | 14 | 0 | 0.000591 (p < 0.001) | 14 | 0 | chr6 | 70,672,513-70,676,431 | 3,918 |
| Fcer2a | 13 | 0 | 0.001074 (p < 0.01) | 13 | 0 | chr8 | 3,681,737-3,694,174 | 12,438 |
| Cd83 | 30 | 6 | 0.001945 (p < 0.01) | 30 | 6 | chr13 | 43,880,476-43,898,501 | 18,026 |
| Arid5a | 11 | 0 | 0.003649 (p < 0.01) | 11 | 0 | chr1 | 36,364,578-36,380,874* | 16,297 |
| Fli1 | 10 | 1 | 0.006825 (p < 0.01) | 11 | 1 | chr9 | 32,229,793-32,348,953 | 119,161 |
| chr4:44725759 | 12 | 0 | 0.01081 (p < 0.05) | 12 | 0 | chr4 | 44,725,759-44,727,010 | 1,251 |
| Clec2d | 8 | 0 | 0.02447 (p < 0.05) | 8 | 0 | chr6 | 129,130,633-129,136,553 | 5,921 |
| Il21r | 6 | 0 | 0.04339 (p < 0.05) | 8 | 0 | chr7 | 132,746,943-132,777,084 | 30,142 |
| Bcl2l11 | 6 | 0 | 0.04339 (p < 0.05) | 6 | 0 | chr2 | 152,606,404-152,657,418 | 51,015 |
| Dync 1h1 | 6 | 0 | 0.04339 (p < 0.05) | 6 | 0 | chr12 | 111,839,605-111,905,154 | 65,550 |

TABLE S2-continued

Number of hits within hotspots and in c-myc$^{25xI-SceI}$ WT and AID-/- HTGTS libraries

| Gene/ intergenic region | n of hits in hotspots[a] | | Binomial test | n of total hits[b] | | | Genomic sequence (mm9, UCSC browser) | Size |
|---|---|---|---|---|---|---|---|---|
| | WT | AID-/- | (p-value) | WT | AID-/- | Chr | | (bp) |
| Lrrc33 | 6 | 0 | 0.04339 (p < 0.05) | 6 | 0 | chr16 | 32,142,911-32,165,562 | 22,652 |
| Mef2c | 6 | 0 | 0.04339 (p < 0.05) | 6 | 0 | chr13 | 83,643,033-83,806,684 | 163,652 |
| Socs2 | 6 | 0 | 0.04339 (p < 0.05) | 6 | 0 | chr10 | 94,874,676-94,879,455* | 5368 |
| Tnfaip3 | 6 | 0 | 0.04339 (p < 0.05) | 6 | 0 | chr10 | 18,720,717-18,735,216* | 14,500 |
| Itpk1 | 1 | 6 | 0.0467 (p < 0.05) | 1 | 6 | chr12 | 103,806,793-103,943,079 | 136,287 |
| ≥3-fold enriched | | | | | | | | |
| Bcl11a | 9 | 2 | 0.134 | 9 | 2 | chr11 | 23,978,056-24,073,558* | 95,503 |
| Rapgef1 | 13 | 4 | 0.1448 | 13 | 4 | chr2 | 29,475,240-29,595,883* | 120,644 |
| Nup62-il4i1 | 8 | 2 | 0.2081 | 8 | 2 | chr7 | 52,071,740-52,096,173 | 24,434 |
| Grap | 6 | 1 | 0.2509 | 6 | 1 | chr11 | 61,466,823-61,486,279 | 19,457 |
| Traf1 | 6 | 1 | 0.2509 | 6 | 1 | chr2 | 34,798,778-34,817,292 | 18,515 |
| Sh3bp5 | 7 | 2 | 0.3192 | 7 | 2 | chr14 | 32,187,150-32,249,219 | 62,070 |
| Zfp608 | 7 | 2 | 0.3192 | 7 | 2 | chr18 | 55,047,702-55,149,567 | 102,136 |
| Pax5 | 9 | 3 | 0.3812 | 9 | 3 | chr4 | 44,544,378-44,723,312 | 178,935 |
| Hivep3 | 6 | 2 | 0.4811 | 8 | 2 | chr4 | 119,487,283-119,808,016 | 320,734 |
| Not Significant | | | | | | | | |
| Gucy2f | 8 | 3 | 0.3766 | 8 | 3 | chrX | 138,515,703-138,631,474 | 117,648 |
| Rad51l1 | 7 | 3 | 0.5348 | 7 | 3 | chr12 | 80,398,269-80,915,677 | 517,409 |
| Sfi1 | 8 | 8 | 0.6149 | 8 | 8 | chr11 | 3,031,853-3,093,466 | 61,614 |
| Ebf1 | 6 | 3 | 0.7425 | 8 | 5 | chr11 | 44,431,636-44,818,674 | 387,039 |
| miR-715 region | 18 | 13 | 1 | 18 | 13 | chr17 | 39,980,196-39,985,774 | 5,206 |
| I-SceI site | | | | | | | | |
| Mpdu1 | 2 | 6 | 0.07648 | 2 | 6 | chr11 | 69,470,206-69,476,144 | 5,939 |
| Mmp24 | 45 | 45 | 0.1355 | 45 | 45 | chr2 | 155,601,080-155,644,102 | 43,023 |
| Scd2 | 4 | 8 | 0.1403 | 4 | 8 | chr19 | 44,368,166-44,381,352 | 13,187 |
| Apbb1 | 19 | 21 | 0.2013 | 19 | 21 | chr7 | 112,706,998-112,730,049* | 23,052 |
| Fermt2 | 19 | 19 | 0.3288 | 19 | 19 | chr14 | 46,078,467-46,149,740 | 71,274 |
| Kirrel3 | 14 | 15 | 0.3477 | 14 | 15 | chr9 | 34,296,316-34,843,892 | 547,577 |
| chr1:31667457 | 10 | 10 | 0.5028 | 10 | 10 | chr1 | 31,667,457-31,668,744 | 1,287 |
| chr1:137751395 | 17 | 15 | 0.5952 | 17 | 15 | chr1 | 137,751,395-137,753,879 | 2,484 |
| 5-hit hotspots & special regions | | | | | | | | |
| Cxcr5 | 5 | 0 | 0.07848 | 5 | 0 | chr9 | 44,319,870-44,334,504 | 14,635 |
| Laptm5 | 5 | 0 | 0.07848 | 5 | 0 | chr4 | 130,469,249-130,492,063 | 22,815 |
| Mad1l1 | 5 | 0 | 0.07848 | 6 | 0 | chr5 | 140,484,643-140,797,506 | 312,864 |
| Man1a | 5 | 0 | 0.07848 | 5 | 0 | chr10 | 53,625,839-53,795,602 | 169,764 |
| Rab35 | 5 | 0 | 0.07848 | 5 | 0 | chr5 | 116,081,996-116,097,167 | 15,172 |

TABLE S2-continued

Number of hits within hotspots and in c-myc$^{25xI\text{-}SceI}$ WT and AID-/- HTGTS libraries

| Gene/intergenic region | n of hits in hotspots[a] WT | n of hits in hotspots[a] AID-/- | Binomial test (p-value) | n of total hits[b] WT | n of total hits[b] AID-/- | Chr | Genomic sequence (mm9, UCSC browser) | Size (bp) |
|---|---|---|---|---|---|---|---|---|
| Cd44 | 5 | 1 | 0.4115 | 5 | 1 | chr2 | 102,651,300-102,741,822* | 90,523 |
| Cflar | 5 | 1 | 0.4115 | 5 | 1 | chr1 | 58,770,130-58,815,726 | 45,597 |
| Dock10 | 5 | 1 | 0.4115 | 5 | 1 | chr1 | 80,497,648-80,755,128 | 257,481 |
| Plekha2 | 5 | 1 | 0.4115 | 5 | 1 | chr8 | 26,149,617-26,212,283 | 62,667 |
| Cdh4 | 5 | 2 | 0.7065 | 7 | 2 | chr2 | 179,177,183-179,634,080 | 456,898 |
| Itpkb | 5 | 2 | 0.7065 | 5 | 2 | chr1 | 182,260,607-182,353,790 | 93,184 |
| Prkca | 5 | 2 | 0.7065 | 6 | 4 | chr11 | 107,794,701-108,205,202 | 410,502 |
| Sept9 | 5 | 3 | 1 | 5 | 3 | chr11 | 117,060,975-117,223,639* | 162,665 |
| Fnbp1 | 5 | 3 | 1 | 5 | 3 | chr2 | 30,881,726-30,997,528** | 115,803 |
| Itpr1 | 1 | 5 | 0.08912 | 2 | 5 | chr6 | 108,163,090-108,501,108 | 338,019 |
| Sipa1l3 | 1 | 5 | 0.08912 | 2 | 5 | chr7 | 30,105,397-30,290,479 | 185,083 |
| Zmiz1 | 3 | 5 | 0.2936 | 3 | 5 | chr14 | 26,278,671-26,486,233 | 207,563 |
| 9130019P16Rik | 3 | 5 | 0.2936 | 3 | 5 | chr6 | 54,219,675-54,380,215 | 160,541 |
| Plcd3 | 4 | 5 | 0.506 | 4 | 5 | chr11 | 102,931,610-102,962,972 | 31,363 |
| Ig λ | 7 | 3 | 0.5348 | 7 | 3 | chr16 | 19,026,951-19,260,937 | 986 |
| V kappa | 2 | 0 | NA | 19 | 11 | chr6 | 67,505,630-70,672,513 | 3.1E+06 |

[a] Derived from 250 kb hotspot bins
[b] Total hits present
*variant 1 (the longest isoform)
**variant 3 (the longest isoform)

TABLE S3

Frequency of hits in genes in WT and AID-/- HTGTS libraries

| Chr | Chr size | Total Gene size | Expected rate | c-myc$^{25xI\text{-}SceI}$/WT (n = 5) Observed rate | c-myc$^{25xI\text{-}SceI}$/WT (n = 5) p value | c-myc$^{25xI\text{-}SceI}$/AID-/- (n = 4) Observed rate | c-myc$^{25xI\text{-}SceI}$/AID-/- (n = 4) p value |
|---|---|---|---|---|---|---|---|
| Chr1 | 197 | 70 | 0.36 | 0.41 ± 0.06 | 0.114 | 0.46 ± 0.08 | 0.075 |
| Chr2 | 182 | 73 | 0.40 | 0.62 ± 0.06 | 0.0019 | 0.57 ± 0.07 | 0.019 |
| Chr3 | 160 | 46 | 0.29 | 0.40 ± 0.06 | 0.012 | 0.49 ± 0.02 | 0.0003 |
| Chr4 | 156 | 55 | 0.35 | 0.49 ± 0.11 | 0.053 | 0.51 ± 0.03 | 0.001 |
| Chr5 | 153 | 61 | 0.40 | 0.60 ± 0.04 | 0.0006 | 0.58 ± 0.08 | 0.025 |
| Chr6 | 150 | 58 | 0.39 | 0.45 ± 0.07 | 0.142 | 0.46 ± 0.07 | 0.144 |
| Chr7 | 153 | 53 | 0.35 | 0.65 ± 0.05 | 0.0002 | 0.62 ± 0.05 | 0.001 |
| Chr8 | 132 | 45 | 0.35 | 0.51 ± 0.09 | 0.014 | 0.49 ± 0.07 | 0.021 |
| Chr9 | 124 | 51 | 0.41 | 0.52 ± 0.04 | 0.002 | 0.58 ± 0.09 | 0.040 |
| Chr10 | 130 | 49 | 0.38 | 0.53 ± 0.06 | 0.006 | 0.55 ± 0.08 | 0.026 |
| Chr11 | 122 | 53 | 0.43 | 0.60 ± 0.02 | 8.9985E−05 | 0.58 ± 0.01 | 0.0003 |
| Chr12 | 121 | 39 | 0.34 | 0.81 ± 0.04 | 1.3954E−05 | 0.39 ± 0.02 | 0.012 |
| Chr13 | 120 | 40 | 0.33 | 0.52 ± 0.08 | 0.006 | 0.48 ± 0.17 | 0.175 |
| Chr14 | 125 | 42 | 0.34 | 0.54 ± 0.10 | 0.010 | 0.64 ± 0.09 | 0.007 |
| Chr15 | 103 | 37 | 0.36 | 0.48 ± 0.05 | 0.006 | 0.51 ± 0.02 | 0.001 |
| Chr16 | 98 | 34 | 0.35 | 0.52 ± 0.03 | 0.0002 | 0.52 ± 0.06 | 0.011 |
| Chr17 | 95 | 36 | 0.38 | 0.54 ± 0.08 | 0.013 | 0.55 ± 0.06 | 0.012 |
| Chr18 | 91 | 31 | 0.40 | 0.53 ± 0.08 | 0.024 | 0.39 ± 0.08 | 0.6194 |
| Chr19 | 61 | 27 | 0.44 | 0.58 ± 0.04 | 0.001 | 0.71 ± 0.05 | 0.001 |
| ChrX | 167 | 42 | 0.25 | 0.36 ± 0.05 | 0.013 | 0.43 ± 0.08 | 0.024 |
| ChrY | 0.77 | 16 | 0.05 | NA | NA | NA | NA |

TABLE S4

Direct PCR assay for translocations between c-myc$^{25xI\text{-}SceI}$ and AID-dependent hotspots genes

| | WT | | | | AID-/- | | | |
|---|---|---|---|---|---|---|---|---|
| | # 247 | | # 311 | | # 409 | | # 494 | |
| | C | I | C | I | C | I | C | I |
| IL4ra | <0.17 | 0.83 | <0.17 | 0.5 | <0.17 | <0.17 | <0.17 | <0.17 |
| Il21r | <0.17 | 0.33 | <0.17 | 0.17 | <0.17 | <0.17 | <0.17 | <0.17 |
| Pim1 | 0.17 | 0.5 | <0.17 | 0.5 | <0.17 | <0.17 | <0.17 | <0.17 |
| CD83 | <0.17 | 0.67 | <0.17 | 0.17 | <0.17 | <0.17 | <0.17 | <0.17 |

Numbers of translocations/$10^5$ cells.

TABLE S5

Number of translocations to cryptic I-SceI sites (in a 4 kb region centered around each site) in each HTGTS library.

| | c-myc$^{25xI\text{-}Sce}$/WT | | | | | | | | c-myc$^{25xI\text{-}Sce}$/AID-/- | | | | | c-myc$^{1xI\text{-}Sce}$/WT | | | |
|---|---|---|---|---|---|---|---|---|---|---|---|---|---|---|---|---|---|
| | 248- | | | 484- | | | | | | | | | | | | | |
| mouse | 249 | 253 | 311 | 485 | 488 | 749 | 858 | TOT | 342 | 409 | 487 | 494 | TOT | 2 | 9 | 183 | TOT |
| chr1 (A) | 1 | 1 | 2 | 3 | 2 | 1 | 0 | 10 | 1 | 6 | 3 | 0 | 10 | 0 | 2 | 3 | 5 |
| chr1 (B) | 3 | 1 | 5 | 3 | 3 | 0 | 0 | 15 | 0 | 6 | 6 | 3 | 15 | 0 | 1 | 3 | 4 |
| chr11 | 0 | 0 | 1 | 0 | 1 | 0 | 0 | 2 | 2 | 2 | 2 | 0 | 6 | 0 | 1 | 5 | 6 |
| chr13 | 0 | 0 | 0 | 0 | 0 | 0 | 0 | 0 | 0 | 0 | 0 | 0 | 0 | 0 | 1 | 0 | 1 |
| chr14 | 2 | 1 | 8 | 2 | 4 | 0 | 0 | 17 | 0 | 7 | 6 | 4 | 17 | 0 | 2 | 9 | 11 |
| chr15 (A) | 1 | 0 | 0 | 1 | 1 | 0 | 0 | 3 | 0 | 1 | 1 | 0 | 2 | 0 | 0 | 1 | 1 |
| chr15 (B) | 2 | 2 | 12 | 5 | 5 | 0 | 0 | 26 | 2 | 11 | 7 | 1 | 21 | 1 | 5 | 5 | 11 |
| chr19 (A) | 0 | 0 | 0 | 0 | 0 | 1 | 0 | 1 | 0 | 2 | 3 | 3 | 8 | 0 | 1 | 1 | 2 |
| chr19 (B) | 2 | 0 | 0 | 0 | 1 | 0 | 0 | 3 | 0 | 0 | 0 | 0 | 0 | 0 | 3 | 1 | 4 |
| chr2 (A) | 0 | 0 | 1 | 2 | 1 | 0 | 0 | 4 | 1 | 0 | 0 | 0 | 1 | 0 | 1 | 0 | 1 |
| chr2 (B) | 1 | 0 | 0 | 0 | 1 | 1 | 0 | 3 | 0 | 4 | 1 | 2 | 7 | 0 | 0 | 1 | 1 |
| chr2 (C) | 2 | 5 | 12 | 4 | 13 | 3 | 2 | 41 | 3 | 19 | 12 | 6 | 40 | 0 | 5 | 4 | 9 |
| chr4 | 0 | 0 | 1 | 2 | 1 | 0 | 0 | 4 | 0 | 1 | 0 | 0 | 1 | 0 | 1 | 0 | 1 |
| chr6 | 0 | 0 | 0 | 0 | 1 | 0 | 0 | 1 | 0 | 2 | 0 | 0 | 2 | 0 | 1 | 0 | 1 |
| chr7 | 1 | 0 | 5 | 4 | 4 | 3 | 0 | 17 | 4 | 3 | 8 | 2 | 17 | 0 | 2 | 3 | 5 |
| chr8 | 0 | 0 | 1 | 0 | 1 | 0 | 0 | 2 | 0 | 1 | 1 | 0 | 2 | 0 | 0 | 1 | 1 |
| chr9 | 0 | 0 | 5 | 2 | 1 | 0 | 0 | 8 | 1 | 8 | 4 | 0 | 13 | 0 | 4 | 3 | 7 |
| chrX | 1 | 0 | 3 | 1 | 1 | 0 | 0 | 6 | 0 | 0 | 2 | 0 | 2 | 0 | 0 | 1 | 1 |

| | ΔSγ1$^{2xI\text{-}Sce}$/WT | | | | ΔSγ1$^{2xI\text{-}Sce}$/AID-/- | | |
|---|---|---|---|---|---|---|---|
| mouse | 186 | 188 | 958 | TOT | 165 | 278 | TOT |
| chr1 (A) | 0 | 0 | 0 | 0 | 0 | 0 | 0 |
| chr1 (B) | 0 | 0 | 0 | 0 | 1 | 0 | 1 |
| chr11 | 0 | 0 | 0 | 0 | 0 | 0 | 0 |
| chr13 | 0 | 0 | 0 | 0 | 0 | 0 | 0 |
| chr14 | 0 | 0 | 0 | 0 | 0 | 0 | 0 |
| chr15 (A) | 0 | 0 | 0 | 0 | 0 | 0 | 0 |
| chr15 (B) | 0 | 0 | 0 | 0 | 0 | 0 | 0 |
| chr19 (A) | 0 | 0 | 0 | 0 | 0 | 0 | 0 |
| chr19 (B) | 0 | 3 | 0 | 3 | 0 | 0 | 0 |
| chr2 (A) | 0 | 0 | 0 | 0 | 0 | 0 | 0 |
| chr2 (B) | 0 | 0 | 0 | 0 | 1 | 0 | 1 |
| chr2 (C) | 1 | 1 | 2 | 4 | 3 | 5 | 8 |
| chr4 | 0 | 0 | 0 | 0 | 0 | 0 | 0 |
| chr6 | 0 | 0 | 0 | 0 | 0 | 0 | 2 |
| chr7 | 0 | 0 | 0 | 0 | 0 | 0 | 0 |

TABLE S5-continued

Number of translocations to cryptic I-SceI sites (in a 4 kb region centered around each site) in each HTGTS library.

| chr8 | 0 | 0 | 0 | 0 | 0 | 0 | 0 |
|------|---|---|---|---|---|---|---|
| chr9 | 0 | 0 | 0 | 0 | 0 | 0 | 0 |
| chrX | 0 | 4 | 0 | 4 | 0 | 1 | 1 |

Note that no translocation to cryptic I-SceI sites was detected in c-myc$^{25xI\text{-}SceI}$/ROSA$^{I\text{-}SceI\text{-}GR}$ libraries, likely due to lower levels of cutting at both "bait" and "prey" loci achieved with inducibe I-SceI-GR as compared to retrovirally-expressed I-SceI.

Example 2

We also showed that our HTGTS system can be used successfully in combination with a so called Hi-C method (Zhang et al. Cell 148: 908-21, Mar. 2, 2012).

The extent to which the three dimensional organization of the genome contributes to chromosomal translocations is an important question in, e.g., cancer genomics. We now have generated a high resolution Hi-C spatial organization map of the G1-arrested mouse pro-B cell genome and mapped translocations from target DNA double strand breaks (DSBs) within it via high throughput genome-wide translocation sequencing. RAG endonuclease-cleaved antigen-receptor loci are dominant translocation partners for target DSBs regardless of genomic position, reflecting high frequency DSBs at these loci and their co-localization in a fraction of cells. To directly assess spatial proximity contributions, we normalized genomic DSBs via ionizing-radiation. Under these conditions, translocations were highly enriched in cis along single chromosomes containing target DSBs and within other chromosomes and sub-chromosomal domains in a manner directly related to pre-existing spatial proximity.

REFERENCES

The references cited herein and throughout the specification and examples are incorporated herein by reference in their entirety to the extent they are consistent with the description and examples.

Aguilera, A. (2002). The connection between transcription and genomic instability. The EMBO journal 21, 195-201.

Arnould, S., et al. (2011). The I-CreI meganuclease and its engineered derivatives: applications from cell modification to gene therapy. Protein Eng Des Sel 24, 27-31.

Chaudhuri, J., et al. (2007). Evolution of the immunoglobulin heavy chain class switch recombination mechanism. Adv Immunol 94, 157-214.

Christian, M., et al. (2010). Targeting DNA double-strand breaks with TAL effector nucleases. Genetics 186, 757-761.

Core, L. J., et al. (2008). Nascent RNA sequencing reveals widespread pausing and divergent initiation at human promoters. Science 322, 1845-1848.

Dimitrova, N., et al. (2008). 53BP1 promotes non-homologous end joining of telomeres by increasing chromatin mobility. Nature 456, 524-528.

Dudley, D. D., et al. (2002). Internal IgH class switch region deletions are position-independent and enhanced by AID expression. Proceedings of the National Academy of Sciences of the United States of America 99, 9984-9989.

Durkin, S. G., and Glover, T. W. (2007). Chromosome fragile sites. Annual review of genetics 41, 169-192.

Ferguson, D. O., et al. (2000). The nonhomologous end-joining pathway of DNA repair is required for genomic stability and the suppression of translocations. Proc Natl Acad Sci USA 97, 6630-6633.

Franco, S., et al. (2006). H2AX prevents DNA breaks from progressing to chromosome breaks and translocations. Molecular Cell 21, 201-214.

Giallourakis, C. C., et al. (2010). Elements between the IgH variable (V) and diversity (D) clusters influence antisense transcription and lineage-specific V(D)J recombination. Proceedings of the National Academy of Sciences of the United States of America 107, 22207-22212.

Gomez-Gonzalez, B., and Aguilera, A. (2007). Activation-induced cytidine deaminase action is strongly stimulated by mutations of the THO complex. Proceedings of the National Academy of Sciences of the United States of America 104, 8409-8414.

Gostissa, M., Alt, F. W., and Chiarle, R. (2011). Mechanisms that Promote and Suppress Chromosomal Translocations in Lymphocytes. Annu Rev Immunol.

Gostissa, M., et al. (2009). Chromosomal location targets different MYC family gene members for oncogenic translocations. Proc Natl Acad Sci USA 106, 2265-2270.

Haffner, M., et al. (2011). Transcription-induced DNA double strand breaks: both an oncogenic force and potential therapeutic target? Clinical cancer research: an official journal of the American Association for Cancer Research.

Handel, E. M., and Cathomen, T. (2011). Zinc-finger nuclease based genome surgery: it's all about specificity. Current gene therapy 11, 28-37.

Jasin, M. (1996). Genetic manipulation of genomes with rare-cutting endonucleases. Trends Genet 12, 224-228.

Kovalchuk, A. L., et al. (2007). AID-deficient Bcl-xL transgenic mice develop delayed atypical plasma cell tumors with unusual Ig/Myc chromosomal rearrangements. The Journal of experimental medicine 204, 2989-3001.

Kuppers, R., and Dalla-Favera, R. (2001). Mechanisms of chromosomal translocations in B cell lymphomas. Oncogene 20, 5580-5594.

Lieber, M. R. (2010). The mechanism of double-strand DNA break repair by the nonhomologous DNA end-joining pathway. Annual review of biochemistry 79, 181-211.

Lieberman-Aiden, E., et al. (2009). Comprehensive mapping of long-range interactions reveals folding principles of the human genome. Science 326, 289-293.

Lin, C., et al. (2009). Nuclear receptor-induced chromosomal proximity and DNA breaks underlie specific translocations in cancer. Cell 139, 1069-1083.

Liu, M., et al. (2008). Two levels of protection for the B cell genome during somatic hypermutation. Nature 451, 841-845.

Liu, M., and Schatz, D. G. (2009). Balancing AID and DNA repair during somatic hypermutation. Trends in immunology 30, 173-181.

Mahowald, G. K., et al. (2009). Aberrantly resolved RAG-mediated DNA breaks in Atm-deficient lymphocytes target chromosomal breakpoints in cis. Proc Natl Acad Sci USA 106, 18339-18344.

Meaburn, K. J., Misteli, T., and Soutoglou, E. (2007). Spatial genome organization in the formation of chromosomal translocations. Seminars in cancer biology 17, 80-90.

Misteli, T., and Soutoglou, E. (2009). The emerging role of nuclear architecture in DNA repair and genome maintenance. Nature reviews Molecular cell biology 10, 243-254.

Muramatsu, M., et al. (2000). Class switch recombination and hypermutation require activation-induced cytidine deaminase (AID), a potential RNA editing enzyme. Cell 102, 553-563.

Nussenzweig, A., and Nussenzweig, M. C. (2010). Origin of chromosomal translocations in lymphoid cancer. Cell 141, 27-38.

Pasqualucci, L., et al. (2001). Hypermutation of multiple proto-oncogenes in B-cell diffuse large-cell lymphomas. Nature 412, 341-346.

Pavri, R. Nussenzweig, M. C. (2011) AID targeting in Antibody Diversity. Adv Immunol In press.

Petek, L. M., Russell, D. W., and Miller, D. G. (2010). Frequent endonuclease cleavage at off-target locations in vivo. Molecular therapy: the journal of the American Society of Gene Therapy 18, 983-986.

Quinlan, A. R., et al. (2010). Genome-wide mapping and assembly of structural variant breakpoints in the mouse genome. Genome research 20, 623-635.

Ramiro, A. R., et al. (2006). Role of genomic instability and p53 in AID-induced c-myc-Igh translocations. Nature 440, 105-109.

Reynaud, S., et al. (2005). Interallelic class switch recombination contributes significantly to class switching in mouse B cells. Journal of immunology 174, 6176-6183.

Robbiani, D. F., et al. (2008). AID Is Required for the Chromosomal Breaks in c-myc that Lead to c-myc/IgH Translocations. Cell 135, 1028-1038.

Shaffer, D. R., and Pandolfi, P. P. (2006). Breaking the rules of cancer. Nature medicine 12, 14-15.

Siebert, P. D., et al. (1995). An improved PCR method for walking in uncloned genomic DNA. Nucleic acids research 23, 1087-1088.

Simsek, D., and Jasin, M. (2010). Alternative end-joining is suppressed by the canonical NHEJ component Xrcc4-ligase IV during chromosomal translocation formation. Nature structural & molecular biology 17, 410-416.

Stratton, M. R., Campbell, P. J., and Futreal, P. A. (2009). The cancer genome. Nature 458, 719-724.

Unniraman, S., Zhou, S., and Schatz, D. G. (2004). Identification of an AID-independent pathway for chromosomal translocations between the Igh switch region and Myc. Nature immunology 5, 1117-1123.

Wang, J. H., et al. (2009). Mechanisms promoting translocations in editing and switching peripheral B cells. Nature 460, 231-236.

Yamane, A., et al. (2011). Deep-sequencing identification of the genomic targets of the cytidine deaminase AID and its cofactor RPA in B lymphocytes. Nature immunology 12, 62-69.

Yan, C. T., et al. (2007). IgH class switching and translocations use a robust non-classical end-joining pathway. Nature 449, 478-482.

Zarrin, A. A., et al. (2007). Antibody class switching mediated by yeast endonuclease-generated DNA breaks. Science 315, 377-381.

Zhang, Y., et al. (2010). The role of mechanistic factors in promoting chromosomal translocations found in lymphoid and other cancers. Adv Immunol 106, 93-133.

Zhu, C., et al. (2002). Unrepaired DNA breaks in p53-deficient cells lead to oncogenic gene amplification subsequent to translocations. Cell 109, 811-821.

We claim:

1. A method for high throughput, genome-wide translocation sequencing (HTGTS) and detection of double-stranded DNA break (DSB) locations, the method comprising the steps of:
   a. exposing a cell to an agent known or suspected of being capable of producing at least one DSB;
   b. optionally allowing the cell to divide for at least 12 hours;
   c. extracting genomic DNA from the cells;
   d. producing a fragmented DNA sample by fragmenting the DNA of the cell with a frequently cutting restriction enzyme;
   e. producing a ligated DNA product by ligating an asymmetric adapter to the fragmented DNA sample, wherein the asymmetric adapter comprises a sequence that is designed to anneal to the DNA end generated by the frequently cutting restriction enzyme and contains a stretch of known DNA sequence that can be used to design a PCR primer for a nested PCR amplification;
   f. digesting the ligated DNA products with an enzyme to block amplification of germline or unrearranged targeted alleles;
   g. producing nested PCR products by performing nested-PCR with adapter- and locus-specific primers using the digested ligated DNA product thereby amplifying the nucleic acid sequences surrounding the junctions around the DSBs;
   h. producing sequenced nested PCR products by sequencing the nested PCR products; and
   i. aligning the sequenced nested PCR products against a reference sequence to identify chromosomal locations of the translocations and the chromosomal locations of the DSBs.

2. The method of claim 1, further comprising a step of inserting into a cell to be analyzed at least one target sequence for the agent that is known to be absent in the genome of the cell to be analyzed prior to step (a) of claim 1.

3. The method of claim 2, wherein the agent is a rare-cutting enzyme.

4. The method of claim 1, wherein the agent is a meganuclease, a transcription activator-like effector nuclease which are sequence specific nucleases made by fusing a transcription activator like effector DNA-binding domain to a catalytic domain of an endonuclease or a zinc-finger nuclease.

5. The method of claim 1, wherein the cells are allowed to divide for 1-5 days.

6. The method of claim 1, wherein the cells are allowed to divide for 2-4 days.

7. The method of claim 1, wherein the step of aligining is performed by a non-human machine.

8. The method of claim 7, wherein the non-human machine comprises a computer executable software.

9. The method of claim 8 further comprising a display module for displaying the results of the step of aligning.

10. The method of claim 1, wherein the cell is a mammalian cell.

11. The method of claim 1, wherein the cell is a plant cell.

* * * * *

UNITED STATES PATENT AND TRADEMARK OFFICE
CERTIFICATE OF CORRECTION

PATENT NO. : 9,518,293 B2
APPLICATION NO. : 14/131236
DATED : December 13, 2016
INVENTOR(S) : Alt et al.

It is certified that error appears in the above-identified patent and that said Letters Patent is hereby corrected as shown below:

In the Specification

At Column 1, Lines 17-20, please delete "This application was supported in part by Grant numbers 5P01CA92625; KO8 grant AI070837; and 5T32CA07008313 awarded by the National Institutes of Healt. Government has certain rights in the invention." and insert the following text: -- This invention was made with government support under grant numbers AI070837, CA092625, and CA070083 awarded by the National Institutes of Health. The Government has certain rights in the invention. --

Signed and Sealed this
Thirty-first Day of July, 2018

Andrei Iancu
*Director of the United States Patent and Trademark Office*

SEQUENCE LISTING

```
<160> NUMBER OF SEQ ID NOS: 76

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
accgccgcta attccgatca tattc                                              25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atagggctgt acggagtcgt agtc                                               24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
gctctgctgt tgctggtgat agaa                                              24

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccttcgagca gggacttagc c                                                 21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcagctgct agtccgacga                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agacgcccag gaatcgccat                                                   20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgagcgtcac tgatagtagg gagt                                              24

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctcaggttt gtctgtggg                                                    19

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
ggaatatatc gagaagcctg agg                                          23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctctacatgc ctgtgcttgt                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcctcgaggg acctaataac                                              20

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtaatacgac tcactatagg gcacgcgtgg tcgacggccc gggctggt               48

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taaccagccc                                                         10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgaccagccc                                                         10

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```
gtaatacgac tcactatagg gc                                               22

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
actatagggc acgcgtggt                                                   19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccctgcctcc cttaagcagg c                                                21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagacttgga gggagggagg g                                                21

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcaaagatgt ttggaggcca ctgc                                             24

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gctcatgcaa cactaccctg tgc                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tctgagagtc ttcccagtcc acc                                              23

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gggaagtgca cagcaaaccg g                                                21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aatcctggta ctggaatcgg                                                  20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agatggcaca ctgctaggac                                                  20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actgctctgc ctggtcacct tg                                               22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgcacgtgat tccagcactt gg                                               22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tccacactca ctacagccat ttcc                                             24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tctcttgttc ccctcatacc tcac                                          24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gacacactgc aaaagctgat cccc                                          24

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcctgccagt cacctcccat c                                             21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acaaggcacc acacaatggg tg                                            22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttaagggcac tgtctgaggg gg                                            22

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaccctcata ctctccagcc acc                                           23

```
<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttgctgccct atgagtcctg gg                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaggctcacc tttcagaggg cc                                              22

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaggcttccc ttatcgtggc acc                                             23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggcatcgcat ccaagtcaac ctc                                             23

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38 cctttttgagg gccacctgac tg                                             22

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttaaggtggt cttccctga ggc                                              23
```

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
aagaggctgt cagtgagccg ag                                              22

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
agtgagaaat gagcaccatg ggc                                             23

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gaggcacgaa gaggctactc ag                                              22

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
tgcttacgcc gctctgtttc t                                               21

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
tatgcagtgt cctggccaag                                                 20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gacctaccac tctgcagctg g                                               21

<210> SEQ ID NO 46

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggagttctag gccagccttg g                                              21

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atgtcctcct tcccacaatg ctg                                            23

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agcagtgctt aaggcagaaa gtctg                                          25

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcctgaactc gacggtagga ac                                             22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agaaccgatc tggcctgaaa cc                                             22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggtcactaac tcatgcccca cc                                             22

<210> SEQ ID NO 52
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gaggagacgg aagtgaagct ctg                                              23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tggccattaa gcacgtggag aag                                              23

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gattggggag aactggtgag tgag                                             24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aagggcacaa gttaggtggt agga                                             24

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agggtgtgag aggaaaatgg tgg                                              23

<210> SEQ ID NO 57
<211> LENGTH: 18
<212> TYPE: DNA
<213> ORGANISM: Mus musculus

<400> SEQUENCE: 57
attaccctgt tatccta                                                     18

<210> SEQ ID NO 58
<211> LENGTH: 18
<212> TYPE: DNA
<213> ORGANISM: Mus musculus

<400> SEQUENCE: 58
```

```
tctgccctgg tatccctg                                                   18

<210> SEQ ID NO 59
<211> LENGTH: 18
<212> TYPE: DNA
<213> ORGANISM: Mus musculus

<400> SEQUENCE: 59
tttagcctgg tatcccta                                                   18

<210> SEQ ID NO 60
<211> LENGTH: 18
<212> TYPE: DNA
<213> ORGANISM: Mus musculus

<400> SEQUENCE: 60
tctgccctgg tatccctg                                                   18

<210> SEQ ID NO 61
<211> LENGTH: 18
<212> TYPE: DNA
<213> ORGANISM: Mus musculus

<400> SEQUENCE: 61
actgccctgt tatcccaa                                                   18

<210> SEQ ID NO 62
<211> LENGTH: 19
<212> TYPE: DNA
<213> ORGANISM: Mus musculus

<400> SEQUENCE: 62
attacccctg ttatcccta                                                  19

<210> SEQ ID NO 63
<211> LENGTH: 18
<212> TYPE: DNA
<213> ORGANISM: Mus musculus

<400> SEQUENCE: 63
gctgccctgg tatcccta                                                   18

<210> SEQ ID NO 64
<211> LENGTH: 18
<212> TYPE: DNA
<213> ORGANISM: Mus musculus

<400> SEQUENCE: 64
actgccctgg catcccta                                                   18

<210> SEQ ID NO 65
<211> LENGTH: 18
<212> TYPE: DNA
<213> ORGANISM: Mus musculus

<400> SEQUENCE: 65
tttgccctgt catcccta                                                   18

<210> SEQ ID NO 66
<211> LENGTH: 19
<212> TYPE: DNA
<213> ORGANISM: Mus musculus
```

```
<400> SEQUENCE: 66
attggccctg ttatccta                                              19

<210> SEQ ID NO 67
<211> LENGTH: 18
<212> TYPE: DNA
<213> ORGANISM: Mus musculus

<400> SEQUENCE: 67
tgagccctgt tatccta                                               18

<210> SEQ ID NO 68
<211> LENGTH: 18
<212> TYPE: DNA
<213> ORGANISM: Mus musculus

<400> SEQUENCE: 68
ataaccctgt tatccctg                                              18

<210> SEQ ID NO 69
<211> LENGTH: 18
<212> TYPE: DNA
<213> ORGANISM: Mus musculus

<400> SEQUENCE: 69
atgaccctgt tatccta                                               18

<210> SEQ ID NO 70
<211> LENGTH: 18
<212> TYPE: DNA
<213> ORGANISM: Mus musculus

<400> SEQUENCE: 70
aataccctgt gatccta                                               18

<210> SEQ ID NO 71
<211> LENGTH: 18
<212> TYPE: DNA
<213> ORGANISM: Mus musculus

<400> SEQUENCE: 71
attaccctgg tatcccaa                                              18

<210> SEQ ID NO 72
<211> LENGTH: 18
<212> TYPE: DNA
<213> ORGANISM: Mus musculus

<400> SEQUENCE: 72
atgcccctgt tatccta                                               18

<210> SEQ ID NO 73
<211> LENGTH: 18
<212> TYPE: DNA
<213> ORGANISM: Mus musculus

<400> SEQUENCE: 73
atgaccctgg tatccta                                               18

<210> SEQ ID NO 74
<211> LENGTH: 18
<212> TYPE: DNA
<213> ORGANISM: Mus musculus
```

```
<400> SEQUENCE: 74
taagacctgg tatcccta                                                18

<210> SEQ ID NO 75
<211> LENGTH: 18
<212> TYPE: DNA
<213> ORGANISM: Mus musculus

<400> SEQUENCE: 75
attaccctgt tatccctt                                                18

<210> SEQ ID NO 76
<211> LENGTH: 9
<212> TYPE: PRT
<213> ORGANISM: Unknown
<220> FEATURE:
<223> OTHER INFORMATION: Description of Unknown: LAGLIDADG motif
      sequence

<400> SEQUENCE: 76

Leu Ala Gly Leu Ile Asp Ala Asp Gly
1               5
```